(12) United States Patent
Jarvius et al.

(10) Patent No.: US 12,241,113 B2
(45) Date of Patent: Mar. 4, 2025

(54) METHOD FOR DETERMINING THE CONCENTRATION OF INTACT MICROORGANISMS IN A SAMPLE

(71) Applicant: Q-LINEA AB, Uppsala (SE)

(72) Inventors: Jonas Jarvius, Uppsala (SE); Jan Grawe, Uppsala (SE); Markus Klintstedt, Uppsala (SE)

(73) Assignee: Q-LINEA AB, Uppsala (SE)

( * ) Notice: Subject to any disclaimer, the term of this patent is extended or adjusted under 35 U.S.C. 154(b) by 1277 days.

(21) Appl. No.: 16/753,549

(22) PCT Filed: Oct. 12, 2018

(86) PCT No.: PCT/EP2018/077852
§ 371 (c)(1),
(2) Date: Apr. 3, 2020

(87) PCT Pub. No.: WO2019/073025
PCT Pub. Date: Apr. 18, 2019

(65) Prior Publication Data
US 2020/0299748 A1    Sep. 24, 2020

(30) Foreign Application Priority Data

Oct. 13, 2017    (GB) .................................... 1716883

(51) Int. Cl.
| | | |
|---|---|---|
| *C12Q 1/06* | (2006.01) |
| *C12M 1/00* | (2006.01) |
| *C12M 1/26* | (2006.01) |
| *C12M 1/34* | (2006.01) |
| *C12M 1/36* | (2006.01) |
| *C12N 1/06* | (2006.01) |
| *C12Q 1/18* | (2006.01) |
| *G01N 1/30* | (2006.01) |
| *G01N 1/31* | (2006.01) |
| *G01N 1/38* | (2006.01) |
| *G01N 21/64* | (2006.01) |

(52) U.S. Cl.
CPC .............. *C12Q 1/06* (2013.01); *C12M 33/14* (2013.01); *C12M 41/06* (2013.01); *C12M 41/36* (2013.01); *C12M 41/48* (2013.01); *C12N 1/06* (2013.01); *C12Q 1/18* (2013.01); *G01N 1/31* (2013.01); *G01N 1/38* (2013.01); *G01N 21/6428* (2013.01); *G01N 21/6456* (2013.01); *G01N 2001/302* (2013.01); *G01N 2021/6441* (2013.01)

(58) Field of Classification Search
CPC ...................................................... C12Q 1/06
See application file for complete search history.

(56) References Cited

U.S. PATENT DOCUMENTS

| | | |
|---|---|---|
| 5,534,416 A | 7/1996 | Millard et al. |
| 5,658,751 A | 8/1997 | Yue et al. |
| 5,863,753 A | 1/1999 | Haugland et al. |
| 6,291,203 B1 | 9/2001 | Poot et al. |
| 6,403,378 B1 | 6/2002 | Phi-Wilson et al. |
| 7,547,526 B2 | 6/2009 | Ladisch et al. |
| 7,893,251 B2 | 2/2011 | Lorenz |
| 8,460,887 B2 | 6/2013 | Goldberg et al. |
| 8,481,265 B2 | 7/2013 | Peytavi et al. |
| 8,652,800 B2 | 2/2014 | Walsh et al. |
| 8,780,181 B2 | 7/2014 | Olesen et al. |
| 10,112,194 B2 | 10/2018 | Jarvius et al. |
| 10,829,797 B2 | 11/2020 | Jarvius et al. |
| 2003/0022270 A1 | 1/2003 | Seaver et al. |
| 2005/0202487 A1 | 9/2005 | Klepp et al. |
| 2008/0305514 A1 | 12/2008 | Alford et al. |
| 2009/0011458 A1 | 1/2009 | Johnson |
| 2010/0047774 A1 | 2/2010 | Van Haag et al. |
| 2010/0124763 A1 | 5/2010 | Walsh et al. |

(Continued)

FOREIGN PATENT DOCUMENTS

| | | |
|---|---|---|
| CN | 1816634 | 8/2006 |
| CN | 103946389 | 7/2014 |

(Continued)

OTHER PUBLICATIONS

Roume et al., "Sequential Isolation of Metabolites, RNA, DNA, and Proteins from the Same Unique Sample" in Methods in Enzymology, vol. 531, Chapter 11, pp. 219-236. (Year: 2013).*
Mansour et al., "Detection of *Escherichia coli* in Blood Using Flow Cytometry", Cytometry 6:186-190 (1985).*
Boardman et al., "Rapid Microbial Sample Preparation from Blood Using a Novel Concentration Device", PLOS One, 10(2): e116837, 2015, pp. 1-13.
Jernaes et al., "Staining and *Escherichia coli* for Flow Cytometry: Influx and Efflux of Ethidium Bromide", Cytometry, 1994, vol. 17, pp. 302-309.

(Continued)

*Primary Examiner* — Suzanne M Noakes
(74) *Attorney, Agent, or Firm* — Wenderoth, Lind & Ponack, L.L.P.

(57) ABSTRACT

The present invention relates to a method of determining the concentration of intact microorganisms in a sample comprising optionally diluting an aliquot of the sample to provide a diluted aliquot at a dilution value; contacting at least a portion of an aliquot or of a diluted aliquot of the sample with first and second stains capable of binding to DNA, wherein the first stain is a fluorescent stain, is cell-permeable, and has a first emission wavelength, and the second stain is cell-impermeable, and is capable of acting as an acceptor molecule in a FRET pair with the first stain acting as a donor molecule; imaging the aliquot-stain mixture at the first emission wavelength and determining an image analysis value for the number of objects corresponding to intact microorganisms in the imaged mixture; and comparing the image analysis value for said aliquot to a pre-determined calibration curve, as well as an apparatus, a consumable and a kit therefor.

12 Claims, 20 Drawing Sheets

(56) References Cited

U.S. PATENT DOCUMENTS

| | | |
|---|---|---|
| 2010/0184210 A1 | 7/2010 | Rossmanith et al. |
| 2012/0231446 A1 | 9/2012 | Heckel et al. |
| 2013/0171615 A1 | 7/2013 | Van Meerbergen et al. |
| 2014/0186832 A1 | 7/2014 | Fuchs et al. |
| 2014/0278136 A1 | 9/2014 | Shamsheyeva et al. |
| 2015/0118677 A1 | 4/2015 | Li et al. |
| 2015/0160245 A1 | 6/2015 | Lieberman et al. |
| 2019/0022649 A1 | 1/2019 | Jarvius et al. |

FOREIGN PATENT DOCUMENTS

| | | |
|---|---|---|
| CN | 104254597 | 12/2014 |
| CN | 104284984 | 1/2015 |
| CN | 106661606 | 5/2017 |
| EP | 0 008 826 | 3/1980 |
| EP | 0 149 165 | 7/1985 |
| EP | 1 256 624 | 11/2002 |
| EP | 2 201 009 | 6/2010 |
| EP | 2 684 947 | 1/2014 |
| EP | 3 118 201 | 1/2017 |
| JP | 10-14594 | 1/1998 |
| JP | 2011-191081 | 9/2011 |
| WO | 96/13552 | 5/1996 |
| WO | 97/17463 | 5/1997 |
| WO | 97/38128 | 10/1997 |
| WO | 2001/36661 | 5/2001 |
| WO | 02/08454 | 1/2002 |
| WO | 03/012199 | 2/2003 |
| WO | 2004/013627 | 2/2004 |
| WO | 2007/120860 | 10/2007 |
| WO | 2010/062350 | 6/2010 |
| WO | 2011/156249 | 12/2011 |
| WO | 2012/162133 | 11/2012 |
| WO | 2013/016211 | 1/2013 |
| WO | 2013/166336 | 11/2013 |
| WO | 2013/166337 | 11/2013 |
| WO | 2013/166338 | 11/2013 |
| WO | 2014/040088 | 3/2014 |
| WO | 2015/189390 | 12/2015 |
| WO | 2016/037051 | 3/2016 |
| WO | 2016/207065 | 12/2016 |
| WO | 2017/216312 | 12/2017 |
| WO | 2017/216314 | 12/2017 |

OTHER PUBLICATIONS

International Search Report and Written Opinion of the International Searching Authority issued Jan. 22, 2019 in International (PCT) Application No. PCT/EP2018/077852.

Search Report issued Jul. 17, 2018 in GB Patent Application No. 1716883.2.

Pitt et al., "Rapid Separation of Bacteria from Blood—Review and Outlook", Biotechnol Prog., Jul. 8, 2016, vol. 32, No. 4, pp. 823-839.

Walsh et al., "Rapid Intrinsic Fluorescence Method for Direct Identification of Pathogens in Blood Cultures", mBio, 2013, vol. 4, No. 6, e00865-13, pp. 1-9.

First Review Notice of Observations, issued Sep. 1, 2023 in corresponding Chinese Patent Application No. 201980009378. 9, with English translation.

Berney et al., "Assessment and Interpretation of Bacterial Viability by Using the LIVE/DEAD BacLight Kit in Combination with Cytometry", Applied and Environmental Microbiology, 2007, vol. 73, No. 10, pp. 3283-3290.

Broeren et al., "Antimicrobial susceptibility testing in 90 min by bacterial cell count monitoring", Clin. Microbiol. Infect., 2013, vol. 19, pp. 286-291.

Dahl et al., "Circle-to-circle amplification for precise and sensitive DNA analysis", PNAS, 2004, vol. 101, No. 13, pp. 4548-4553.

EUCAST Discussion Document E.Dis 5.1, "Determination of minimum inhibitory concentrations (MICs) of antibacterial agents by broth dilution", European Society of Clinical Microbiology and Infectious Diseases, 2003, 7 pages.

Fredborg et al., "Real-Time Optical Antimicrobial Susceptibility Testing", Journal of Clinical Microbiology, 2013, vol. 51, No. 7, pp. 2047-2053.

Grégori et al., "Resolution of Viable and Membrane-Compromised Bacteria in Freshwater and Marine Waters Based on Analytical Flow Cytometry and Nucleic Acid Double Staining", Applied and Environmental Microbiology, 2001, vol. 67, No. 10, pp. 4662-4670.

Thermofisher Scientific, "LIVE/DEAD BacLight Bacterial Viability Kits, Product Information", 2004, 8 pages.

Metzger et al., "Rapid simultaneous identification and quantification of *Staphylococcus aureus* and Pseudomonas aeruginosa directly from bronchoalveolar lavage specimens using automated microscopy", Diagnostic Microbiology and Infectious Disease, 2014, vol. 79, pp. 160-165.

Netuschil et al., "Confusion over live/dead stainings for the detection of vital microorganisms in oral biofilms-which statin is suitable?", BMC Oral Health, 2014, vol. 14, No. 2, 12 pages.

Pascaud et al., "A fluorescence-based assay for measuring the viable cell concentration of mixed microbial communities in soil", Journal of Microbiological Methods, 2009, vol. 76, pp. 81-87.

Price et al., "Rapid antibiotic susceptibility phenotypic characterization of *Staphylococcus aureus* using automated microscopy of small numbers of cells", Journal of Microbiological Methods, 2014, vol. 98, pp. 50-58.

Shi et al., "Limits of Propidium Iodide as a Cell Viability Indicator for Environmental Bacteria", Cytometry Part A, 2007, vol. 71, No. 8., 592-598.

Stiefel et al., "Critical aspects of using bacterial cell viability assays with the fluorophores SYTO9 and propidium iodide", BMC Microbiology, 2015, vol. 15, No. 36, 9 pages.

Sullivan et al., "Practical Aerobic Membrane Filtration Blood Culture Technique: Development of Procedure", Journal of Clinical Microbiology, 1975, vol. 1, No. 1, pp. 30-36.

Bacteria Counting Kit manual, Molecular Probes, Invitrogen Detection Technologies, 2007, 4 pages.

"SYTO Green-Fluorescent Nucleic Acid Stains" manual, Molecular Probes, Life Technologies, 2014, 8 pages.

Trevors, "Can dead bacterial cells be defines and are genes expressed after cell death?", Journal of Microbiological Methods, 2012, vol. 90, pp. 25-28.

Zierdt et al., "Development of a Lysis-Filtration Blood Culture Technique", Journal of Clinical Microbiology, 1977, vol. 5, No. 1, pp. 46-50.

International Search Report and Written Opinion of the International Searching Authority, issued Jan. 22, 2019 in corresponding International Patent Application No. PCT/EP2018/077852.

"CyQUANT Direct Cell Proliferation Assay Kit", Jul. 20, 2009, pp. 1-8. XP055073845, http://tools.invitrogen.com/content/sfs/manuals/mp35011.pdf.

Li et al., "A live-cell high-throughput screening assay for identification of fatty acid uptake inhibitors", Analytical Biochemistry, 336(1): 11-19 (2005).

Zierdt, Charles H. Simplified lysed-blood culture technique. Journal of Clinical Microbiology (1986) vol. 23, No. 3, pp. 452-455.

Sigma, Product Information for Polyoxyethylene 10 Oleoyl Ether, Sigma Product No. P6136, https://www.sigmaaldrich.com/deepweb/assets/sigmaaldrich/product/documents/263/219/p6136pis.pdf; accessed Oct. 16, 2023 (Year: 1996).

ThermoFisher Scientific; SYTO™ 13 Green Fluorescent Nucleic Acid Stain—5 mM Solution in DMSO, Catalog No. S7575, https://www.thermofisher.com/order/catalog/product/S7575; accessed Oct. 11, 2023 (Year: 2006).

Ullal, A.J et al. "Use of SYTO 13, a fluorescent dye binding nucleic acids, for the detection of microparticles in in vitro systems", Cytometry A (2010) 77(3):294-301.

Darynkiewicz; DNA staining for cell cycle, https://www.kumc.edu/documents/flow/DNA%20staining%20for%20cell%20cycle.pdf; accessed Oct. 16, 2023 (Year: 2014).

Kim, S-O et al . . . Mechanical properties of paraformaldehyde-treated individual cells investigated by atomic force microscopy and scanning ion conductance microscopy. Nano Converg. (2017) 4(1):5. 8 pages.

(56) References Cited

OTHER PUBLICATIONS

American Red Cross, Platelets and Thrombocytopenia; https://www.redcrossblood.org/donate-blood/dlp/platelet-information.html#:-:text=Platelets%2C%20or%20thrombocytes%2C%20are%20small,white%20blood%20cells%2C%20and%20platelets; accessed Oct. 11, 2023 (Year: 2023).

Blaxland, B. Humans are mammals; Australian Museum; https://australian.museum/learn/science/human-evolution/humans-are-mammals/; accessed Oct. 11, 2023 (Year: 2023).

Bio Rad; 10% Tween 20, Nonionic Detergent #1610781; https://www.bio-rad.com/en-us/sku/1610781-10-tween-20-nonionic-detergent?ID=1610781; accessed Oct. 11, 2023 (Year: 2023).

Jove; https://www.jove.com/v/10188/calibration-curves-principles-and-applications#:-:text=Use%20the%20line%20equation%20to,drink%20was%20diluted%201%3A1.; (Year: 2023).

Weber Scientific; Phosphate Buffers: Here's What You Need to Know; https://www.weberscientific.com/phosphate-buffers-here-s-what-you-need-to-know; accessed Oct. 16, 2023 (Year: 2023).

Ma, Qian et al. Three-dimensional fluorescent microscopy via simultaneous illumination and detection at multiple planes. Scientific Reports (2016) 6:31445. DOI: 10.1038/srep31445.

Chamgoulov, R. et al. Optical computed-tomographic microscope for three-dimensional quantitative histology. Cellular Oncology (2004) vol. 26, pp. 319-327.

Office Action issued Oct. 24, 2023 in related U.S. Appl. No. 16/962,980.

* cited by examiner

METHOD FOR DETERMINING THE CONCENTRATION OF INTACT MICROORGANISMS IN A SAMPLE

The present invention relates generally to the detection and characterisation of a microorganism in a sample. In particular, the present invention provides a rapid method for measuring the concentration of intact, microorganisms in a sample. In particular, the intact microorganisms may be viable.

Traditionally, microbial growth and the concentration of microorganisms in a sample have been determined by measuring an optical parameter of the sample, such as its turbidity. For example, McFarland standards are used in microbiology as a reference for the turbidity of a sample, so that the number of microorganisms (typically bacteria) within a sample will be within a given range of turbidity, and such standards can be used in a nephelometer to determine the concentration of microorganisms in a sample. Alternative techniques comprising spectrophotometry to determine the concentration of microorganisms in a sample may be used. However, although rapid and easily implemented, such techniques are only capable of approximating the number of microorganisms in a sample. The relationship between turbidity or the absorbance of a particular wavelength of light and the concentration of microorganisms in a sample also varies for different microorganism species, making it difficult to estimate the concentration of microorganisms when the identity of the microorganism in question is not known. Furthermore, such techniques are only capable of measuring the total turbidity or absorbance of a sample, and thus cannot distinguish between viable (i.e. live) and non-viable (i.e. dead) cells in a sample, or indeed between intact microorganisms or cellular or other debris in the sample. Turbidimetric measurement of the concentration of microorganisms in a sample also has low sensitivity, and a relatively high concentration of microorganisms is required in order to be able to measure the concentration of microorganisms in a sample. This prevents low concentrations being measured in this way, and may also require an extended culture step before a measurement can be made.

The number of viable microorganisms in a sample can also be estimated more quantitatively by plating a portion (or a diluted portion) of the sample on a solid growth medium, incubating the sample, and counting the number of colonies which are formed. However, the down-side of such techniques is that it requires a lengthy incubation step in order to allow sufficient time for microbial growth to take place. Such classical techniques are therefore useful for measuring the concentration of microorganisms in a sample at a particular point in time, but are of limited use where the concentration of viable microorganisms is required quickly, e.g. to perform a test or assay on the microorganism in that sample that requires prior knowledge of the number of microorganisms present in the sample.

It is well-known in the field of microorganism detection that viable (i.e. live) cells may also be differentiated from dead cells, and a number of techniques are available for this purpose. Methods known in the art focus on nucleic acid stains, membrane potential, redox indicators or reporter genes. Typically, these techniques rely on the fact that the membrane of a viable microorganism is intact, whilst that of a dead microorganism is disrupted and/or broken (Gregori et al. 2001. Appl. Environ. Microbiol. 67, 4662-4670).

A particular technique which allows dead cells to be differentiated from live cells is that of dead/live staining. By using a dye or stain which is non-membrane permeable, only cells which have a disrupted membrane are stained, whilst cells which have an intact membrane are not. The dye/stain thus acts as a marker for dead cells, as only those cells with a disrupted membrane (i.e. dead cells) are stained using such a dye. In this way, dead cells may be detected, and furthermore the proportion of the total cells which are dead can be calculated. Further advances in this field have led to the development of techniques using two separate stains: a first, which is cell-permeable and can enter both live and dead cells; and a second, which is cell-impermeable, and can only enter dead cells. Live and dead cells can therefore be differentially-labelled, and may thus be distinguished. An example of a kit for performing this technique is the LIVE/DEAD BacLight Bacterial Viability Kit (Invitrogen), which comprises the SYTO9 (cell permeable) stain and propidium iodide (PI) (cell impermeable) fluorescent dyes. By detecting microbial cells at the emission wavelengths of both first and second stains used in such kits, such techniques may be particularly useful in differentiating between live and dead microbial cells, thereby to determine the proportion of viable microorganisms present in a sample. A number of different detection techniques can be used to distinguish differentially stained live and microbial cells in a sample. For example, it is possible to directly count the number of microbial cells in a sample which are indicated as viable and non-viable, e.g. in a microscope field of view, and in this way determine the proportion of viable microorganisms present in a sample. However, such techniques are labour and time intensive, and do not allow the concentration of viable microorganisms to be accurately determined. Automated cell counting methods such flow cytometry may also be used to measure the proportion of viable microorganisms in a sample when combined with live/dead staining techniques (Berney et al. 2007. Applied and Environmental Microbiology 73, 3283-3290), however, complex and highly specialist instrumentation, and regular calibration (e.g. a separate calibration before measuring each sample) is required in flow cytometric methods. Such techniques therefore are typically not suitable for use in a robust detection method such as is required for routine clinical laboratory use, and automation of such techniques may be difficult. There is therefore a need for straightforward, rapid and robust methods and instruments for measuring the concentration of intact microorganisms in a sample, particularly for clinical use.

As discussed above, microorganisms which have an intact cell membrane can be stained differently to those which have a damaged or disrupted cell membrane when suitable dyes are used. Detecting viable cells by live/dead staining therefore typically comprises detecting cells having an intact cell membrane, and cells having an intact cell membrane are therefore considered to represent viable cells for the purposes of measuring the concentration of viable microbial cells in a sample. The correlation between a cell being intact and being viable is good, and thus utilising differential staining provides a straightforward and rapid way for the concentration of viable cells to be determined without requiring direct measurements of viability, which often comprise lengthy incubation steps, to be performed. It has in some cases been reported that whilst a proportion of microbial cells which are indicated as 'viable' in a live/dead staining assay may comprise an intact cell membrane, they may, as a matter of fact, be metabolically inactive or otherwise non-culturable (Trevors 2012. J Microbiol Meth 90, 25-8). Furthermore, during fast exponential growth in nutrient rich environments the membrane integrity of viable microbial cells may be reduced, thereby allowing the second fluorescent dye to enter the cells (Shi et al. 2007. Cytom Part A 71A, 592-298). Such cells would therefore emit light at the second emission wavelength, and due to the ability of the second fluorescent stain to quench the fluorescence of the first fluorescent stain, the fluorescence of such cells at the first emission wavelength may be reduced. Additionally, problems such as bleaching and higher than expected uptake of the first (cell permeable) fluorescent stain may affect the accuracy of such methods (Stiefel et al. 2015. BMC Microbiology 15:36). Nevertheless, these factors are not considered significantly to affect the results of methods to determine the amount or concentration of viable microorganisms in a sample, and detecting intact cells is considered to be an effective way for the amount or concentration of viable cells in a sample to be determined. Indeed, the present inventors have shown that such staining methods may be used, as further described below, to provide an indication of the concentration of viable microorganisms in a sample.

As noted above, in many instances in microbiology it is desirable to determine the concentration of microorganisms, and in particular viable microorganisms. This may be desirable to allow a suitable concentration or number of microorganisms to be provided for an assay to characterise a microorganism, so that said assay may be performed correctly, or indeed to ensure that a sample is suitable for use in a particular assay. Notably, this may include the preparation of standard (or standardised) cultures, or inocula for cultures. This includes particularly the preparation of standardised inocula for antibiotic susceptibility tests (ASTs), which for clinical purposes in the detection and identification of microbial infections require an inoculum which is of a known or predetermined, or standard, concentration. However, it may also be desirable to determine the concentration of microorganisms in a sample, or provide a standard culture for other assays discussed in greater detail below.

Numerous processes in biology and medicine require the accurate determination of the number of microorganisms (particularly viable microorganisms) in a sample, and the preparation of an inoculum based on said determination. These include, for example, water and food quality control analysis, monitoring of microorganisms in an environmental sample, biofilm formation in or on medical equipment or in a patient, and laboratory microbiological research. In particular, the accurate determination of the concentration of viable microbial cells in a sample, and the preparation of an inoculum containing a desired concentration of microorganisms therefrom may be of use in the diagnosis of a microbial infection.

Microbial infections represent a major class of human and animal disease with significant clinical and economic implications. Whilst various classes and types of antimicrobial agents are available to treat and/or prevent microbial infections, antimicrobial resistance is a large and growing problem in modern medicine. In the context of treatment of a microbial infection, it can therefore be desirable, and indeed important, to have information regarding the nature of the infecting microorganism and its antimicrobial susceptibility profile in order both to ensure effective treatment and also to reduce the use of unnecessary or ineffective antibiotics and thereby to help control the spread of antibiotic, or more generally antimicrobial, resistance. This is particularly so in the case of serious or life-threatening infections in which rapid effective treatment is vital.

Sepsis, a potentially fatal whole-body inflammation caused by severe infection is the most expensive condition and driver of hospital costs in the US, comprising 5% of the total national hospital cost. Mortality increases 7% for every hour for severe sepsis, if not treated properly, and the rising prevalence of antimicrobial-resistant sepsis causing strains makes predictions of the correct treatment for sepsis increasingly difficult. The current gold standard for diagnosis of the microorganisms causing sepsis or other infections is based on phenotypic and biochemical identification techniques which require the isolation and culture of pure cultures of the infecting microorganisms. It can take several days to perform the microbial identification (ID) and antibiotic susceptibility (AST) tests to identify the infection and determine the susceptibility profile of the microorganism, which may be resistant to one or more antibiotics. An AST assay provides a 'minimum inhibitory concentration' or 'MIC' value for each antimicrobial agent tested on a microorganism, and can thus provide information on which antimicrobial agents may be effective against the microorganism. The more quickly such information can be provided the better, and hence rapid AST methods are desirable and are being developed.

Generally speaking, results obtained for AST determinations in the clinical field should be comparable between different methods and/or different clinical laboratories. To this end it is customary to use prescribed and recognised conditions for AST testing. This may involve the use of prescribed medium (e.g. Muller-Hinton (MH) media) and culture conditions. In particular, it is also customary to use standardised microbial titres (i.e. a standardised (or standard) number or amount (e.g. concentration) of microbial cells) to set up the cultures which are performed (i.e. monitored for growth) in an AST test, such that the number or amount of bacteria in the cultures is at a set value. For example, McFarland standards are conventionally used as a reference to adjust the turbidity of microbial suspensions (especially bacterial suspensions) so that the number of microorganisms in the culture preparation used to set up the cultures will be within a given range to standardise AST testing. McFarland standards are set based on the turbidity of reference suspensions, and microbial suspensions are adjusted in concentration (or number of bacteria) to match the turbidity of a selected McFarland standard.

Conventionally (e.g. as described for the EUCAST standard method for determining MICs of antimicrobial agents (European Committee for Antimicrobial Susceptibility Testing (EUCAST) of the European Society of Clinical Microbiology and Infectious Diseases (ESCMID) (2003), Determination of minimum inhibitory concentrations (MICs) of antibacterial agents by broth dilution. Clinical Microbiology and Infection, 9: ix-xv.), microbial cells to be tested for AST (e.g. from a clinical sample culture) are plated and incubated to obtain isolated colonies. Colonies may then be collected and used to prepare a microbial cell suspension for use as the inoculum for use in the AST assay. Typically, and as described in the guidelines described above, the concentration of microorganisms in the suspension thus prepared is set to a standard and pre-defined level, e.g. 0.5 McFarland units, to allow a standard concentration of microorganisms to be used in an AST assay. The turbidity of the microbial suspension may be adjusted to 0.5 McFarland before use. Alternatively, the isolated individual colonies may be used to inoculate a culture medium which may be cultured to provide the inoculum. The culture may be allowed to grow to the desired (0.5 McFarland) standard and/or may be adjusted if necessary to this standard, before it is used as the inoculum. Thus before normalizing the concentration of bacteria before an AST, microbial cultures are typically allowed to grow until the growth reaches a turbidity equal to or greater than that of a 0.5 McFarland standard. If needed, the culture may be adjusted to give culture having a turbidity equivalent to the 0.5 McFarland standard. This may then be used as the inoculum that is used to set up an AST assay. The inoculum obtained at this point (i.e. the culture or suspension of approximately 0.5 McFarland units) is diluted in broth to give the desired standardised final cell number concentration used for an AST culture. By way of reference, a microbial culture/suspension of 0.5 McFarland units comprises a microbial concentration of approximately $1\times10^8$ CFU/ml. Such a microbial culture/suspension would typically be diluted in broth by a factor of ~200 when setting up an AST culture, i.e. each AST culture condition would typically comprise a starting microbial concentration of approximately $5\times10^5$ CFU/ml.

For certain microbial infections, such as sepsis, a blood sample is typically collected in a blood culture flask, and a microbial culture (i.e. a clinical sample culture) is allowed to grow until a positive culture result is obtained in a culture monitoring system. In automatic culture detection systems such as e.g. Bactec or Bact/Alert systems the concentration of bacteria needed to be indicated as positive is between $10^8$ to $10^9$ CFU/ml, corresponding to 0.5 to 3.5 McFarland units (if measured in a saline solution). The lowest McFarland value that is readily detectable (either by eye or by turbidimetric measurements) is around 0.5 McFarland units.

ID tests and AST determination may be performed using such a clinical sample culture, generally once a positive culture result has been obtained. For an AST test, it is typical to prepare a further culture from the clinical sample culture (e.g. a positive culture) to use as, or for preparing, an inoculum for the AST test cultures and to standardise such an inoculum to a pre-set microbial concentration or McFarland value (typically 0.5 McFarland units) before it is used to inoculate the AST test cultures. Thus inocula for AST are typically prepared using, or starting from, cultures or microbial suspensions which are at 0.5 McFarland units. This is typically done in the methods of the art by selecting colonies obtained by plating the clinical sample culture or microorganisms isolated therefrom as described above.

Techniques which require comparison with McFarland standards to determine the concentration of microorganism in a sample only provide an approximation for the concentration, and fail to provide information specifically on the concentration of viable microbial cells in a sample. Furthermore, such techniques rely on the concentration of microorganisms in the sample to be relatively high (e.g. 0.5 McFarland units) in order for the concentration to be measured.

There is therefore a particular need to improve the speed and sensitivity with which the concentration of microorganisms in a sample is determined, particularly in the context of setting up an AST assay. In particular, there is a need for a robust and simple method which allows the rapid, accurate and sensitive microorganism concentration determination to be performed without requiring complex instrumentation, such as methods which comprise flow cytometry. The present invention addresses this need by providing an improved method for determining the concentration of a microorganism, which may be used in the preparation of a microbial inoculum, and further to provide an improved workflow for performing an AST assay, and which allows the concentration of microorganisms in a sample, and more significantly the concentration of intact, or viable, microorganisms in a sample, to be accurately and rapidly determined. In particular, the concentration determination method of the present invention is of value in enabling a rapid AST assay to be performed. Thus, the present invention seeks to provide a rapid, accurate and precise method for determining the concentration of microorganism in a sample, and more significantly the concentration of intact microorganisms. As noted above, the concentration of intact microorganisms may be used as a reliable indicator of viable microorganisms, and in one embodiment the method may be used for determining the concentration of viable microorganisms.

In particular, the method of the present invention is based on staining intact microorganisms (based on live/dead staining principles) and imaging the sample, or a diluted aliquot of the sample, in order to determine a value for the number of objects corresponding to intact microorganisms in the sample, rather than directly counting microorganisms in a sample or estimating the concentration of microorganisms turbidimetrically with respect to a pre-determined standard, or counting the number of viable microorganisms present by counting cultured colonies. By using a predetermined standard curve, the determined values for the number of objects detected by imaging may be correlated to the concentration of microorganisms present in the sample.

Accordingly, in a first aspect, the present invention provides a method of determining the concentration of intact microorganisms in a sample, said method comprising:
 a. providing a sample containing microorganisms;
 b. optionally diluting an aliquot of said sample to provide a diluted aliquot at a dilution value;
 c. contacting at least a portion of an aliquot of the sample of step (a), or a diluted aliquot of the sample either during or after dilution step (b), with first and second stains capable of binding to DNA to provide a sample-stain mixture, wherein said first stain is a fluorescent stain, is cell-permeable, and has a first emission wavelength, and said second stain is cell-impermeable, and wherein the second stain is capable of acting as an acceptor molecule in a FRET pair with the first stain acting as a donor molecule;
 d. imaging the aliquot-stain mixture of step (c) at the first emission wavelength and determining an image analysis value for the number of objects corresponding to intact microorganisms in the imaged mixture; and
 e. comparing the image analysis value for said aliquot to a pre-determined calibration curve, thereby to determine the concentration of intact microorganisms in said sample.

By comparing the image analysis value for the number of objects detected by imaging in step (c) with a pre-determined calibration curve, a more accurate measure of the number of intact microorganisms in the sample may be obtained. Such a method allows the factors described above which can adversely affect the determination of the concentration of viable cells in a sample to be taken into account (i.e. 'factored in' to any such determination), thereby resulting in a more accurate measure of microbial viability. Thus, the concentration of intact microbial cells may be taken to represent, or to indicate or correspond to, or approximate, the concentration of viable microbial cells, as discussed above. Specifically, by comparing the image analysis value for the number of objects imaged in step (c) with a pre-determined calibration curve, factors such as incorrect staining of viable and non-viable microbial cells discussed above can be taken into account when attempting to calculate the concentration of intact, and more particularly viable, microorganisms present in a sample, thus allowing a more accurate determination of the concentration of intact or viable microorganisms in a sample to be made.

The present invention provides a rapid and sensitive method for determining the concentration of microorganisms in a sample. This may have a number of utilities and it can be advantageous to have a robust and simple method for determination of microbial concentration in a number of situations. As well as determining concentrations where needed in accurate detail, or as an absolute concentration, the method may also have utility in giving an indication of microbial load in sample, and thus may be of use in any method or context where it is desired to know or to estimate, or have an idea of, how many microbial cells are present. The context in which this method may be used is therefore not limited. Indeed, given the low limit of detection of this method, this method may be used to determine whether or not a sample contains microorganisms. Thus, in one aspect the present invention provides a method for determining the presence of a microorganism in a sample, said method comprising performing steps (a)-(e) of the concentration determination method of the present invention, and determining whether microorganisms are present in the sample.

The method may have utility in the context of different samples where it may be desirable to assess or determine microbial concentration. This may be clinical samples, as discussed further below, or any sample in which microorganisms may be present (food, environmental samples etc.). Thus the method may be used to determine if a sufficient or appropriate concentration of cells is present in the sample to enable further tests to be carried out. This is described further below in the context of an AST assay, but the method may be used as a preliminary step before any step of subsequent analysis of the microorganisms in the sample. For example the method may be used to determine or assess the concentration of intact (or viable) microorganisms in a sample before carrying out mass-spectroscopy tests, and/or nucleic acid based tests, and/or any other evaluation of the microorganism, e.g. growth-based studies.

Once the concentration of intact (or viable) microorganisms in a sample has been determined, this information may advantageously be used to accurately prepare an inoculum containing a known or desired number or concentration of microorganisms.

Accordingly, in a further aspect the invention provides a method of preparing a microbial inoculum (or, alternatively expressed, an inoculum for use in preparing a microbial culture), said method comprising determining the concentration of intact microorganisms in a microbial sample using the concentration determination method as defined herein, and then adjusting the concentration of microbial cells in at least an aliquot or portion of the sample to a desired concentration, thereby to provide an inoculum comprising a desired concentration of microorganisms.

The present invention also provides methods for characterising a microorganism in a sample once the concentration of microorganisms in said sample has been determined. Thus, the concentration determination method of the present invention may be used in conjunction with an assay for characterising a microorganism. In particular, this may be an assay which requires a known or pre-determined concentration or number of microorganisms.

Thus, in another aspect, the present invention provides a method for characterising a microorganism in a sample, said method comprising:
(i) providing a sample containing a microorganism;
(ii) performing steps (b)-(e) of the concentration determination method of the present invention as defined above and herein on said sample to determine the concentration of intact microbial cells in said sample;
(iii) adjusting the concentration of microbial cells in said sample, if necessary, to a desired or pre-determined concentration; and
(iv) characterising the microorganism in the sample.

The present invention therefore allows the concentration of microorganisms in a sample to be determined prior to performing an assay, particularly an assay which requires a particular concentration or number of microorganisms, to characterise said microorganism. This therefore allows it to be determined whether a sample is suitable for use in a given assay, and if not, allows the concentration of microorganisms to be adjusted appropriately.

In a further aspect the present invention provides a method for determining the antimicrobial susceptibility of a microorganism in a sample, said method comprising:
(i) providing a sample containing a microorganism;
(ii) performing steps (b)-(e) of the concentration determination method of the present invention as defined above and herein on said sample to determine the concentration of viable microbial cells in said sample;
(iii) inoculating a series of test microbial cultures for an antibiotic susceptibility test (AST) using the sample in step (i), wherein the series of test microbial cultures comprises at least two different growth conditions, wherein the different growth conditions comprise one or more different antimicrobial agents, and each antimicrobial agent is tested at two or more different concentrations; and
(iv) assessing the degree of microbial growth in each growth condition;
wherein the concentration of microbial cells in said sample or said test microbial cultures is adjusted if necessary to a desired or pre-determined concentration; and
wherein the degree of microbial growth in each growth condition is used to determine at least one MIC value for at least one antimicrobial agent, thereby to determine the antimicrobial susceptibility of said microorganism in said sample.

The present invention therefore provides a more accurate method for performing an AST assay, as it allows the concentration of microorganisms to be determined with greater accuracy than measuring turbidity of a sample (e.g. by a simple comparison of the turbidity of a sample with that of a McFarland standard).

As described above, a standard AST assay performed according to EUCAST guidelines typically requires periods of time for microorganisms to grow sufficiently to be used in the next step of setting up the AST assay. For example, in the protocol outlined above a period of incubation is required to allow the concentration of microorganisms in the clinical sample culture to increase to a point where the clinical sample culture is regarded as 'positive' (i.e. it reaches at least 0.5 McFarland units). Further incubation steps are required following plating of the clinical sample culture to allow individual colonies to grow, and optionally an additional further incubation step is required to allow a microbial suspension prepared as outlined above to reach 0.5 McFarland units before an AST assay can be prepared.

Furthermore, in the protocol outlined above for preparing an AST assay, typically only one or a small number of colonies (relative to the total number of microorganisms present in a clinical sample culture) are used to prepare an inoculum that is eventually used to set up an AST assay. Such a protocol therefore relies on the colony or colonies used being representative of the microorganisms causative for an infection. Where this is not the case, the results of the AST assay may not truly reflect the antimicrobial susceptibility of the microorganisms causative for an infection, and any clinical intervention based on such results may therefore fail to adequately treat the infection.

As described in greater detail below, it may be possible to use the concentration determination methods of the present invention to determine the concentration of microorganisms present in a sample containing microorganisms that have been recovered from another sample. This may be done significantly to reduce the time required to characterise a microorganism in a sample. In particular, it may be possible to use the concentration determination methods of the present invention in this way significantly to reduce the time required for an AST assay to be performed, and to improve the reliability of the results obtained therefrom. Put another way, the present invention allows an AST assay to be set up using a sample of microorganisms recovered directly from a sample, i.e. using a recovered microorganism sample.

Thus, the present invention provides a method for characterising a microorganism in a sample, said method comprising:
(i) recovering microorganisms from said sample to provide a recovered microorganism sample;
(ii) performing steps (b)-(e) of the concentration determination method of the present invention as defined above and herein to determine the concentration of intact microorganisms in the recovered microorganism sample;
(iii) adjusting the concentration of microbial cells in said recovered microorganism sample, if necessary, to a desired or pre-determined concentration; and
(iv) characterising the microorganism in the recovered microorganism sample.

In particular, the present invention provides a method for determining the antimicrobial susceptibility of a microorganism in a sample, said method comprising:
i) recovering microorganisms from a sample to provide a recovered microorganism sample;
ii) performing steps (b)-(e) of the concentration determination method of the present invention as defined above and herein to determine the concentration of intact microorganisms in the recovered microorganism sample;
iii) inoculating a series of test microbial cultures for an antimicrobial susceptibility test (AST) using the recovered microorganism sample in step (i), wherein the series of test microbial cultures comprises at least two different growth conditions, wherein the different growth conditions comprise one or more different antimicrobial agents, and each antimicrobial agent is tested at two or more different concentrations; and
iv) assessing the degree of microbial growth in each growth condition;
wherein the concentration of microorganisms in said recovered microorganism sample or said test microbial cultures is adjusted, if necessary, to a desired or pre-determined concentration; and
wherein the degree of microbial growth in each growth condition is used to determine at least one MIC value for at least one antimicrobial agent, thereby to determine the antimicrobial susceptibility of said microorganism in said sample.

The sample from which the microorganisms are recovered may be any sample which contains microorganisms, including pure cultures or suspensions of microorganisms, and clinical or biological or food, water or environmental or any other sample which it may be desired to test for microbial infection, contamination or colonisation and particularly cultures of such samples (notably cultures of clinical samples), as discussed further below. Thus, microorganisms may be isolated (or separated or purified) from a sample in the recovery step. Methods for selective isolation of microbial cells away from other (non-microbial) cells (e.g. mammalian cells) and/or other material present in the sample are described below.

Typically, methods for the recovery of microbial cells from a sample result in the formation of cell debris, e.g. the remains of lysed non-microbial cells in the selective lysis of non-microbial cells in a clinical sample. Advantageously, the method of the present invention allows intact (or viable) microorganisms to be identified and more importantly differentiated from non-microbial cell debris (and indeed non-intact or non-viable microbial cells) which may be present in the sample following recovery of microbial cells from the sample. Thus, the concentration of intact microorganisms recovered from a sample may be determined rapidly and accurately.

The microorganisms recovered from a sample may thus be used in a subsequent assay to allow them to be characterised. In one embodiment, therefore, the microorganisms recovered from the sample may thus be used to inoculate the test microbial cultures in an AST assay. In this way, not only may at least one incubation step be omitted when preparing the inoculum that is used to inoculate each test microbial culture (thereby reducing the time taken before an AST assay is set up), said inoculum will also contain a more complete (i.e. more representative) sample of the microorganisms present in the original clinical sample culture, i.e. the microorganisms causative of an infection in a subject. The present invention therefore provides a more rapid and more reliable method for determining the antimicrobial susceptibility of a microorganism in a sample.

More broadly, however, the present invention provides methods for rapidly and accurately determining the concentration of intact microorganisms in a sample in order to allow a suitable concentration or number of microbial cells to be used in a qualitative or quantitative assay to characterise said microorganism. Put another way, the concentration of intact microorganisms in a sample may be determined prior to any desirable method of characterising a microorganism, in order to allow a suitable concentration or number of microbial cells to be provided for a characterisation method. This therefore allows the characterisation of a microorganism using any such assay.

Assays for which it may be particularly advantageous to determine the concentration of intact microorganisms in a sample include, for example, mass spectrometry (including MALDI-TOF, ESI-MS and CyTOF), Raman spectroscopy, nucleic acid-based tests (including PCR, rolling circle amplification (RCA), ligase chain reaction (LCR), and nucleic acid sequence based amplification (NASBA), which may be of particular utility in identifying a microorganism and/or a marker for antimicrobial resistance therein). As described in greater detail elsewhere herein, it may be of particular benefit to determine the concentration of intact microorganisms in a sample prior to performing an AST assay.

As used herein, the terms "microbial cell" and "microorganism" are interchangeable and are considered to have equivalent meanings, namely a microscopic organism. The term is used broadly herein to include all categories of microorganism, whether unicellular or not, and includes bacteria, including archaea and mycobacteria, fungi, protists, including protozoa, and algae, as discussed in greater detail below. The identity of the microorganisms may be known or unknown when the method is carried out. Further the sample may contain one type or species of microorganism or more than one type or species, i.e. the sample may be of a single microorganism or may contain a mixture of microorganisms.

Furthermore, reference to "cell permeable" and "cell impermeable" stains is made in reference to microbial cells. In other words, the permeability of the first and second stains used in the methods of the present invention is the permeability of microorganisms to said stains.

The term "viable" in the context of the present invention refers to microorganisms that are able to grow and/or reproduce. In other words, the present invention allows the concentration of microorganisms in a sample which are capable of growth (e.g. in an AST assay) to be determined. The term "viability" refers to the ability of microbial cells to grow and/or reproduce. The concentration of viable microorganisms in a sample is determined indirectly, by determining the concentration of intact microorganisms in the sample by differential staining. The concentration of viable microorganisms is therefore derived from the concentration of intact cells in the sample, and the method of the invention provides an accurate and rapid way for the concentration of viable microorganisms in the sample. More particularly, when a sample containing viable microorganisms is used in step (a) the determination of the concentration of intact microorganisms according to the invention reflects, or provides an indication of the concentration of viable microorganisms.

The concentration of viable microorganisms may be proportional to the concentration of intact microorganisms, and the concentration of viable microorganisms in a sample may be determined based on knowledge of how a particular concentration of intact microorganisms correlates to a particular concentration of viable microorganisms. This relationship may be affected by factors such the nature of the sample and/or the microorganism and/or any steps for recovering a microorganism from a sample. This relationship may be determined straightforwardly in a manner akin to the preparation of pre-determined calibration curves as described hereinafter, i.e. by determining the relationship between the concentration of intact and viable cells in a known sample i.e. a sample for which the concentration of microorganisms is or has been determined by an alternative method microorganisms. By way of representative example, this may comprise plating a sample containing a known concentration of intact microorganisms (and thus a known number of intact microorganisms) and determining the resulting number of colonies (i.e. the number of colony forming units) which are formed therefrom. Determining the relationship between the concentration of intact and viable microorganisms may allow the concentration of viable microorganisms in a sample to be determined in the methods of the invention.

As described in greater detail below, a range of samples containing a range of possible microorganisms may be analysed in the methods of the present invention. Thus, available samples may contain a wide range of possible different concentrations of microorganisms, and it may not be possible for a single calibration curve or calibration curves to be prepared in order to allow such a range of concentrations to be accurately determined. It may, therefore, be beneficial to dilute an aliquot of the sample containing microorganisms during the course of performing the method of the present invention, such that the image analysis value for the number of objects determined in step (d) falls within the range of a pre-determined calibration curve.

Further, depending on the nature of the sample it may also be desirable to dilute the sample to allow the concentration determination to be performed, e.g. to dilute (or minimise or reduce the amount of) contaminants or components which may interfere in the concentration determination method. For example, certain media (e.g. Muller Hinton media) contain components which may interfere in fluorescence determinations, and if the sample is a culture sample containing such media, or if recovered microorganisms are resuspended in such a medium, then a dilution step may be desirable.

When a dilution is to be made, i.e. where an aliquot of the sample is diluted in step (b) to provide a diluted aliquot at a dilution value, contacting step (c) takes place either during or after dilution step (b). An aliquot of the sample may, therefore be diluted prior to being contacted with the first and second stains. In such a situation the dilution medium may be a buffer, or saline or water or other aqueous solution etc. However, in certain embodiments, dilution step (b) may comprise contacting an aliquot of the sample with first and second stains capable of binding to a DNA e.g. as a solution containing the first and second stains, and the resulting increase in volume of the aliquot of the sample resulting from contacting the aliquot with the first and second stains thus may be thought of a dilution step, or at least a part of a dilution step. Furthermore, contacting a portion of an aliquot of a sample with first and second stains may be performed before said aliquot is contacted with a further diluent (described below), thereby to provide a diluted aliquot of the sample, and such a procedure may be considered to fall within the definition of contacting a diluted aliquot of the sample with the first and second stains during dilution step (b).

Two or more aliquots may be prepared, such that each aliquot is diluted to different extents. In other words, each aliquot may be diluted at a different dilution factor or dilution value. In such an embodiment, a first aliquot (i.e. at a first dilution value) may be an aliquot of the sample, and a second aliquot (or subsequent) aliquot may be a diluted aliquot at a second (or subsequent) dilution value. Alternatively, two separate dilutions may be performed. One or more of the diluted aliquots may be diluted by serial dilution. Thus, a dilution series may be prepared, by a set of sequential, separate or simultaneous steps, as desired.

The dilutions may be prepared sequentially during steps (b) and/or (c) but prior to step (d), and/or they may be prepared sequentially during or after steps (d) and/or (e).

In certain embodiments of the invention, where two or more aliquots are prepared, each said aliquot may be prepared simultaneously (or substantially simultaneously, including by sequential or serial steps) before or during contacting step (c). In such an event, steps (d) and (e) may be performed on each aliquot simultaneously or sequentially. In other words, each aliquot may be imaged simultaneously (i.e. in parallel), or sequentially, and the respective image analysis values obtained from each aliquot may be compared to a pre-determined calibration curve. Steps (d) and (e) may alternatively be performed on a first aliquot, and if the image analysis value obtained from said aliquot falls within the range of a pre-determined standard calibration curve, steps (d) and (e) may be dispensed with for second or further aliquots.

In an alternative embodiment, however, a diluted aliquot (or second or further diluted aliquot) may only prepared once the steps of the method have been performed on a first aliquot (which may be an aliquot of the sample or a diluted aliquot). Such an embodiment may be desirable if, for example, the image analysis value does not fall within the range of a pre-determined calibration curve. In such an embodiment, it may be necessary for the method of the invention to be repeated on a second (or further) aliquot at a different dilution value. In such an event, it will be seen that each of the two (or further) aliquots are prepared sequentially, i.e. after steps (d) and/or (e) have been performed e.g. on a first aliquot.

Steps (d) and/or (e) may therefore be performed on one aliquot (which may be a diluted or non-diluted aliquot), even if more than one aliquot is prepared, or on two more aliquots (which may be diluted aliquots, or may include an undiluted aliquot).

The steps (c) and (d) may therefore be performed on each aliquot of two or more aliquots, thereby to determine an image analysis value for the number of objects corresponding to viable microorganisms in each aliquot. Where two or more image analysis values have been obtained for each of two or more aliquots, step (e) may comprise identifying an aliquot which comprises an image analysis value within the range of a pre-determined calibration curve, and comparing the image analysis value for said aliquot to a pre-determined calibration curve, thereby to determine the concentration of microorganisms in said sample. In such an event, steps (c) and (d) may be performed on each aliquot sequentially or simultaneously. As noted above, the aliquots may be diluted aliquots, or they may comprise an undiluted aliquot.

Dilution may comprise contacting an aliquot of the sample with a volume of a suitable sterile buffer or aqueous solution (e.g. saline or a salt solution) or indeed any suitable diluent. In other embodiments the diluent may include a solution containing one or both of the first and/or second stains. Different diluents may be used to prepare different diluted aliquots in a dilution series. In one embodiment one or more dilutions may be prepared using a non-stain containing diluent and further dilutions may be prepared using a stain-containing solution (i.e. during step (c)), and these latter diluted aliquots may be used in step (d). Thus, a non-stain containing diluent may be used simply to prepare intermediate diluted aliquots (in step (b)) which are then diluted further in step (c) for the subsequent steps of the method. Alternatively, dilution may take place solely in step (c) using one or more stain-containing solutions.

In certain embodiments, the first and second stains may be pre-mixed prior to contacting the at least portion of the aliquot of the sample. However, it is also envisaged that separate and sequential contact may be performed, and furthermore that this may be done in any order (e.g. the at least portion of the aliquot may be contacted with either the first or the second stain, followed by being contacted with the remaining stain).

The first and second stains used in the methods of the present invention are each capable of binding to DNA, and are each required to have particular properties which make them suitable for use such methods. Specifically, the first stain is a fluorescent stain, and is required to be cell permeable, such that it may cross the (intact) membrane of intact (e.g. viable) microorganisms, thereby to bind to DNA situated within intact (e.g. viable) microbial cells, whereas the second stain is required to be cell impermeable. In this way, only the first stain is anticipated to enter intact microbial cells, whilst the second stain is unable to enter intact microbial cells, thereby ensuring that intact microbial cells are only stained with the first stain. By contrast, both the first and second stains are capable of entering non-intact microbial cells (i.e. microbial cells having damaged or disrupted cell membranes), and thus non-intact (e.g. non-viable) microbial cells may be distinguished from intact (e.g. viable) cells.

Further discrimination between intact and non-intact microbial cells in the methods of the present invention is achieved through the use of a first fluorescent stain, the fluorescence of which is quenched by the second stain. In other words, the second stain is capable of acting as an acceptor molecule in a Förster resonance energy transfer (FRET) (also known as fluorescence resonance energy transfer) pair, with the first fluorescent stain acting as a donor molecule. In other words, the first and second stains are selected such that the emission spectrum of the first (fluorescent) stain (i.e. the FRET donor) overlaps at least partly with the absorption spectrum of the second stain (i.e. the FRET acceptor).

In this way, any cells which are stained with both the first and second stains will have a reduced fluorescence signal intensity at the first emission wavelength, as at least a portion of any signal arising from the first stain will be quenched by the second stain by FRET. The result of this is that not only are non-intact microbial cells differentially stained with the second fluorescent stain, said cells also have a reduced degree of fluorescence at the emission wavelength of the first stain. In certain embodiments of the invention, this may allow only the first stain to be detected in order to determine the concentration of intact microorganisms in a sample.

In a preferred embodiment, yet further discrimination between intact and non-intact microbial cells is made possible by providing first and second stains wherein the first stain has a lower DNA binding affinity than the second stain. In this way, in any (non-intact) cell which is stained by both the first and second stains, the second stain will be able to displace the first stain from DNA within the cell, further weakening the fluorescence intensity of said cell at the first emission wavelength. Thus, the second stain may preferably have a higher DNA binding affinity than the first stain, such that the second stain is able to displace the first stain from DNA.

Certain stains capable of binding to DNA are also known to have enhanced fluorescence when bound to DNA compared to when present freely in solution. It is preferable that the first and/or second fluorescent stains are selected based on displaying this property. In other words, in a preferred embodiment, the fluorescence intensity of the stain is enhanced when the stain is bound to DNA. It is particularly preferred that the fluorescence intensity of the first fluorescent stain is enhanced in this way. Selection of a first (and optionally second) stain having this property may help reduce the level of background signal generated during detection at the first (and optionally second) emission wavelengths. In particular, a stain may be selected which has low fluorescence when unbound to DNA (i.e. when free in solution). For example, when free in solution the stain may exhibit less than 50%, or more preferably less than 40, 30, 20 or 10% of the fluorescence, or more preferably less than 10%, e.g. less than 9%, 8%, 7%, 6%, 5%, 4%, 3%, 2%, or 1% of the fluorescence which it exhibits when bound to DNA, or less than 0.9%, 0.8%, 0.7%, 0.6%, 0.5%, 0.4%, 0.3%, 0.2% or 0.1% of the fluorescence.

It is preferred that the first stain has excitation and emission wavelengths in the wavelength 350-700 nm. A range of suitable fluorescent stains having emission wavelengths within this range are commonly known in the art, and exemplary fluorescent stains are described below. Preferably in the methods of the present invention the first fluorescent stain is a green-fluorescent stain, i.e. having a peak fluorescence emission intensity at or around light having a wavelength of 510 nm.

Particularly preferred first stains, having all of the desirable properties described above include SYTO green fluorescent nucleic acid stains (Molecular Probes). SYTO stains are examples of unsymmetrical cyanine dyes, and unsymmetrical cyanine dyes may therefore preferably be used as first stains in the methods of the present invention. Structures of SYTO dyes which are available are provided in U.S. Pat. Nos. 5,658,751, 6,291,203, 5,863,753, 5,534,416 and 5,658,751. A number of different SYTO stains are available, including SYTO9, SYTO 11, SYTO 12, SYTO 13, SYTO 14, SYTO 16, SYTO 21 and SYTO 24, and may be of use in the methods of the present invention, Particularly preferred are SYTO9 and/or SYTO13, or SYTO BC, which is a mixture of dyes. The SYTO BC stain mixture has an excitation wavelength at 473-491 nm and an emission wavelength at 502-561 nm.

The second stain may preferably have an absorbance wavelength in the wavelengths 350-700 nm. Where the second stain is a fluorescent stain, the excitation wavelength of the second stain may be within this range. However, as noted above, the absorbance spectrum of the second strain is required to at least partially overlap with the emission spectrum of the first stain, and thus the excitation wavelength of the second stain will be close to the emission wavelength of the first stain.

The second stain may in certain embodiments also be a fluorescent stain. In other words, in certain embodiments, both the first and second stains may be fluorescent stains, and step (a) of the methods of the present invention comprises contacting at least a portion of an aliquot of a sample with first and second fluorescent stains. Preferably, when the second stain is a fluorescent stain, the emission wavelength of the second stain is also in the wavelengths 350-700 nm.

Where the first and second stains are fluorescent stains, the respective stain will have different emission wavelengths, in order to allow each stain to be distinguished and detected separately. Thus, first and second emission wavelengths are different. Typically, where both the first and second stains are fluorescent stains, the emission wavelength of the second stain will be at a longer wavelength of light than that of the first stain, due to the fact that the respective stains are capable of acting as FRET donors/acceptors as described above.

In a preferred embodiment, the second fluorescent stain is a red-fluorescent stain, i.e. having a peak fluorescence emission intensity at or around light having a wavelength of 650 nm. A preferred red-fluorescent stain suitable for use in the methods of present invention as a second fluorescent stain is propidium iodide (PI).

A preferred combination of fluorescent stains which have been shown to be surprisingly effective at distinguishing viable microbial cells from non-viable microbial cells comprises a SYTO stain, for example SYTO 9 or BC, as a first fluorescent stain, with PI as a second fluorescent stain.

In certain embodiments, however, the second stain may be a non-fluorescent stain, i.e. a stain which does not emit light in response to excitation with light at a particular wavelength. Nonfluorescent acceptors such as dabcyl and QSY dyes have the advantage of eliminating the potential problem of background fluorescence resulting from direct acceptor excitation, e.g. particularly within non-intact cells.

The aliquot may be contacted with stains at temperatures which are not harmful to microorganisms therein, which allow the stains to permeate intact and non-intact microorganisms as appropriate, and which allow staining to take place. A suitable temperature may be selected, for example, based on the nature of the sample or the identity of a microorganism therein. However, typically temperatures of 37° C. or less are used, in order to avoid damaging microorganisms in a sample. Thus, temperatures of 35° C., 30° C. or 25° or less may be used. It is also preferred that temperatures of 4° C. or greater are used, for example 5° C., 10° C. or 15° C. or greater. In a preferred embodiment, the sample is contacted with the stains at 20-30° C., more particularly at 20° C.-25° C. In certain embodiments, the sample may thus be contacted with the stains at room temperature.

Optionally, an aliquot may be treated prior to (i.e. pre-treated) or during contacting step (c), e.g. to enhance the staining process, e.g. to inactivate or modify the microorganisms before staining. Such a treatment step may comprise contacting the aliquot with an alcohol, for example with ethanol, prior to or during contacting step (c). This may take place before, simultaneously with or after the aliquot is diluted in step (b), and/or contacting the aliquot with an alcohol may comprise at least a part of the dilution step (b). In a particular embodiment, this may take place during step (c) of contacting the aliquot with the stains. Optionally the alcohol may be removed before performing step (d), however, removal of the alcohol is not required, and thus step (d) may be performed on an alcohol/aliquot/stain mixture. Such alcohol treatment therefore may improve staining of microorganisms. In certain embodiments, the aliquot may be contacted with ethanol to provide a mixture comprising 20-50% v/v ethanol, e.g. 25-50% v/v ethanol or 30-45% v/v ethanol. In a particular embodiment, the aliquot is contacted with ethanol to provide a mixture comprising 45% v/v ethanol.

An object is identified as corresponding to an intact microorganism by detecting a fluorescent signal at the first emission wavelength. Owing to the respective properties of the stains used, fluorescent signals at the first emission wavelength arise from intact microorganisms whilst other items in a sample (e.g. non-intact microorganisms, cell debris or other particles present in a sample) are not fluorescent at said wavelength, or are fluorescent to a lesser extent than intact microbial cells. Thus, objects corresponding to intact microbial cells have different fluorescence properties to other objects in the sample, and may be distinguished from other objects in the sample, thereby to allow the number of objects corresponding to intact microbial cells to be determined.

Imaging of the aliquot-stain mixture is performed by visual detection means. A magnified image of the aliquot-stain mixture is obtained and analysed to detect objects which correspond to intact microorganisms.

Whilst an object which corresponds to an intact microorganism may be an intact microbial cell, it may also be a cluster of two or more cells, e.g. a clone growing as a cluster and/or an aggregate of non-clonal cells. Thus, an object may be a microbial cell or cell cluster. Different microorganisms may grow in different ways, e.g. clustering or non-clustering, or with different patterns or morphologies, and for a given microorganism this may also vary depending on the growth conditions, for example the presence or amount of an anti-microbial agent. By analysing the images and counting objects and then correlating the number of objects to a microbial concentration, such different growth patterns and/or morphologies etc., may be taken into account. Thus, the images may be analysed by counting the number of objects and adjusting the number based, for example, on the size and/or intensity of the objects (e.g. to account for clusters or aggregates of cells), to provide an image analysis value for the number of objects, which may then be correlated to the concentration of intact microorganisms using a calibration curve. This is discussed further below.

Imaging the aliquot-stain mixture may take place at temperatures which are not harmful to microorganisms. Typically this will take place at room temperature, or 20-25° C., although other temperatures, e.g. from at least 4° C. up to 37° C. (i.e. 37° C. or less) may also be used Imaging is performed at least at the emission wavelength of the first stain, i.e. to detect objects which are stained by the first fluorescent stain. As described above, this may provide sufficient information to allow objects corresponding to intact microorganisms to be distinguished from other objects which might be present in the sample.

In certain embodiments, imaging may only comprise imagining the aliquot-stain mixture at the first emission wavelength, and thus optionally step (d) does not comprise detecting the second stain. However, in some embodiments it may be beneficial to detect the signals arising from both the first and second stains, and thus imaging may be performed at the first emission wavelength, and may also comprise detecting the second stain. In certain embodiments, imaging may therefore be performed at a wavelength corresponding to the emission wavelength of a second fluorescent stain in addition to that of the first fluorescent stain, or put another way, may comprise detecting the second emission wavelength).

Where the method comprises detecting both the first and second stains, detection of each stain may be performed either separately, e.g. sequentially, or simultaneously. Step (c) may therefore comprise imaging the aliquot-stain mixture separately to detect the first stain (i.e. at the first emission wavelength), or may comprise simultaneously imaging the aliquot-stain mixture to detect the first and second stains.

Imaging may comprise the use of microscopy, including brightfield, oblique field, darkfield, dispersion staining, phase contrast, differential interference contrast, fluorescence, confocal microscopy, single-plane illumination, light sheet and wide field multiphoton microscopy.

Microorganisms may be allowed to contact, bind, associate with or adsorb onto a detection surface for imaging. However, in a preferred embodiment, imaging may be performed on a suspension of microorganisms, i.e. microorganisms which are in a suitable medium or buffer, rather than microorganisms which are immobilised on or at a surface. In other words, a volume of the stain-aliquot mixture may be imaged. Where imaging is performed on a suspension of microorganisms, an image may be obtained at one or more focal planes through the suspension. It may be preferred for an image to be obtained at two or more (different) focal planes through the suspension (e.g. at different depths or cross-sections through the aliquot-stain mixture). In other words, separate sub-volumes of the volume to be imaged may be imaged (i.e. images may be obtained of separate sub-volumes of the stain-aliquot mixture volume). Thus, multiple (i.e. two or more) non-overlapping images may be obtained. Such multiple images may include at least 5, 10, 20, 30, 40, 50, 60, 70, 80, 90 or 100, or more, images. The images are analysed to detect and/or identify objects corresponding to intact microorganisms. An image analysis value for the number of objects is thereby obtained. Objects detected in all images obtained of the sample may provide the total number of objects in the sample.

To perform the imaging step, the stain-aliquot mixture from step (c), or a portion or aliquot thereof is provided in (e.g. transferred to) a vessel or container in which imaging can take place, for example the well of a plate, or a compartment of a carrier suitable for imaging. Such a well or compartment will have an optical viewing area or space, i.e. a viewing (or viewable) area or space which is accessible to a microscope (or more particularly the objective thereof) and is of optical quality to allow microscopic viewing and imaging. The geometry of the well/compartment may give a viewable area of a defined or desired size (e.g. at least 2 mm by 2 mm), with a suitable or desired liquid height to allow a volume to be imaged (e.g. at least 2 mm liquid height). The objective may be focused on a plane inside the well or compartment, for example parallel to the bottom, removed at a distance from the bottom (e.g. about 0.1-0.5, e.g. 0.2 mm from the bottom), and the microscope may be configured to move the focal plane continuously through the liquid during the time of imaging, for example for a total of 1-3 mm (e.g. 1.5 mm) during the image acquisition time (e.g. 10-60, or 20-30 seconds).

In a particularly preferred embodiment, imaging may comprise obtaining a series of 2-D images along an optical axis, wherein each image is obtained at a different position along the optical axis through a volume of the suspension. In certain embodiments, each image may be aligned perpendicularly to the optical axis (here termed xy-aligned). A specific area of the aliquot-sample mixture is covered in a single xy-aligned image the size of which is dependent on the optical properties of the imaging apparatus. For each position in xy-space, one or more 2D images can be collected at different intervals along the optical or z axis. Thus, a series, or stack, of 2D images can be generated, which can, in one embodiment, be used to provide 3D information of a sample volume. Alternatively, multiple individual images providing 2D information can be used. An alternative method of extracting 3D information from a sample is that employed by Unisensor (see e.g. U.S. Pat. No. 8,780,181), where the optical axis is tilted with respect to the xy-plane, and the sample or detector is moved along either the x or y plane. Here, a series of images with an extension into z space, in addition to xy space, is acquired. Through a subsequent transformation of the image data, stacks of 2D images aligned perpendicularly to the xy plane can be achieved also with this method. In this way, each of the series of images is an image of a separate area (separate cross-section), or may alternatively be considered to be a separate volume (a cross section has a defined volume in a z direction, thus a volume comprising the xy space with a depth z may be provided for each image).

Once extracted, the 3D information inherent in the 2D image stacks can be utilized to identify objects corresponding to intact microorganisms in the sample. In one embodiment, 2-D images may be generated from 3-D information by e.g. projections of z-stacks into one 2-D image (a projected 2-D image). Analysis may then be performed using the resulting 2-D image. Alternatively, analysis may be performed on each image obtained through the volume of the suspension, and the results of the analysis may be integrated across all of the 2-D images obtained of the sample. As yet a further alternative, analysis may be performed separately on each of the respective 2-D images obtained (i.e. objects may be determined separately in each 2-D image), and the information gathered therefrom may be combined. Objects may be determined as points or areas of fluorescence intensity indicating an intact microorganism in the field of view under investigation, e.g. in the image or projected 2D image. Analysis may be performed for fluorescent images, and many alternative algorithms for this exist, e.g. in Cellprofiler, and also in most commercial image analysis systems.

In another embodiment, intensity variation in the z space stretching over each position in xy space is registered, indicating microbial mass in a specific position. Integrated over the entire xy space, this gives a measure of total microbial volume. Algorithms for this procedure also exist in commonly available image analysis software, e.g. in the freeware Cellprofiler.

Once objects corresponding to intact microorganisms (i.e. detected at the first emission wavelength) have been detected by imaging, the information thus obtained may be used to generate an image analysis value for the aliquot. Images may be analysed for fluorescence intensity and/or size of an (e.g. each) object, and optionally the morphology of an (e.g. each) object. Factors such as the circularity of an object, evenness of fluorescence intensity in an object or maximum fluorescence intensity (e.g. maximum intensity of pixels therein), modal fluorescence intensity, median or mean fluorescence intensity in an object, and/or area of each object detected by imaging may be determined. In certain embodiments, only those objects having one or more of these parameters within a given range may be included in the analysis (e.g. counted or enumerated), thereby to generate an image analysis value. The image analysis value may be a combined value for the objects identified, in the sense of being representative of, or corresponding to, the number of objects, i.e. a count. Object area may be determined on the basis of the number of contiguous pixels contained in each object, and only those objects containing at least or over a certain number of pixels may be included in the analysis. In certain embodiments, objects may be identified and detected on the basis of a derived value for the object area x intensity, and only those objects having properties falling within a particular range of parameters may be counted or enumerated, thereby to generate an image analysis value. In other words, the image analysis value represents the number of objects corresponding to intact microorganisms having characteristics falling within a particular range of parameters, or in other words a corrected (or adjusted) number of objects corresponding to intact microorganisms.

Factors determined for each object (e.g. any of the factors described above) or derived values such as object area x intensity for all of the objects may also be combined to provide information on the population of imaged objects, i.e. on the totality of objects. In this way, for example, maximum, modal or median fluorescence intensity of the imaged objects (or more particularly of a set, or group, of imaged objects) may be determined. Alternatively, the distribution of the fluorescence intensity of the imaged objects, or a derived value such as object area x intensity for the imaged objects may be determined. Thus, each object may have a value assigned to it (e.g. area, maximum fluorescence intensity, total, median or mean intensity), and the median or mean, or variance or standard deviation of one or more of said factors may be established for the population of imaged objects. As described in greater detail below, such information may indicate properties of microorganisms in the sample, and may be used in the selection of a suitable calibration curve for use in determining the concentration of intact microorganisms therein. Furthermore, such information may provide information on the efficiency of labelling of microorganisms in the sample, and may be used to determine the proportion of microorganisms having a fluorescence intensity below a detection limit.

A background subtraction or normalisation step may optionally be performed for the images as an initial step, i.e. prior to any subsequent image analysis steps described herein. This may be performed using any convenient known standard methods, e.g. rolling ball subtraction.

The image analysis value may be determined after thresholding has been performed. In other words a threshold may be set for determining whether or not an object has been detected. Thresholding may be performed to set a lower limit in the intensity of the signal obtained for an image of the sample, below which objects are not considered. Within the context of the method of the present invention, thresholding allows objects with a low fluorescence intensity at the first emission wavelength (i.e. objects which are not intensely stained with the first stain) to be discarded from any future analysis. Thresholds may be set at one or more levels and objects may be counted at different thresholds.

In certain embodiments global thresholding may be performed, i.e. a single threshold value may be set for the whole of an image (or the set of images). In alternative embodiments, however, local thresholding may be performed (e.g. if illumination and/or background signal is not uniform across an image. Local thresholding estimates a threshold value for a given pixel according to the greyscale information of neighbouring pixels.

Further, other image analysis operations may be performed, according to techniques known in the art, prior to determining the image analysis value, for example to convert the image to grayscale (wherein fluorescence intensity may be read as a grayscale level), and/or to subtract background (e.g. using the rolling ball method) etc.

A sample may be characterised based on information obtained from imaging, for example, whether the microorganisms are clustering or non-clustering microorganisms. Advantageously, selection of a suitable calibration curve for this process may be based only on the appearance of the objects in the sample, for example whether a particular proportion of the objects detected in the sample have a particular area and/or maximum intensity, and may not require the identity of the microorganism in said sample to be known before the concentration of intact microorganisms can be determined by the method of the present invention. A calibration curve may therefore be selected which is predetermined for clustering or non-clustering microorganisms.

The relationship between the concentration of intact microorganisms in a sample and the image analysis value may depend on a number of parameters regarding the microorganism in said sample, e.g. the size and morphology of a microorganism, and/or the tendency of a microorganism to form clusters or biofilms. The number of objects in a sample is therefore not used directly to determine the concentration of intact microorganisms in the sample, as each object may correspond to two or more microorganisms. Furthermore, a microorganism or a cluster of microorganisms may appear in two separate images if taken at different focal planes in embodiments of the invention where imaging is performed at two or more focal planes, and thus may be detected as two separate objects. Thus, the identity of a microorganism in a sample may affect the relationship between the concentration of microorganisms in a sample and the number of objects which are imaged in step (c) of the methods of the present invention.

Factors such as these, and those previously identified in the art as affecting the accuracy of methods of determining the concentration of viable microorganisms in a sample (e.g. through imperfect staining of viable and non-viable microorganisms), may be overcome in the methods of the present invention through the use of calibration curves.

A calibration curve may be prepared by performing steps (c) and (d) of the concentration determination method of the present invention on a series of samples which contain known concentrations of microorganisms, i.e. samples for which the concentration of microorganisms is or has been determined by an alternative method. Thus, the number of objects corresponding to intact microorganisms may be determined for each of the samples containing different concentrations of microorganisms, and thus the relationship between the number of said objects and a concentration of microorganisms may be established.

A calibration curve is pre-determined, in the sense that it is prepared prior to performing the concentration determination method of the present invention. A calibration curve may, therefore, be prepared separately before determining the concentration of microorganisms in a given (i.e. every) sample. However, it is preferred that a calibration curve may be prepared and used to determine the concentration of intact microorganisms in multiple samples, or put another way, the concentration of intact microorganisms in multiple samples may be determined using the same calibration curve. In other words, it is not necessary for the method to comprise the generation of a calibration curve; a pre-prepared calibration curve can be used, and a separate calibration curve does not need to be generated for each sample. A new or fresh calibration curve may be prepared periodically, e.g. daily, weekly or monthly, or may be prepared batch-wise, e.g. before a new batch of stain is used, and said new calibration curve may be used to determine the concentration of intact microorganisms until it is required that a new calibration curve is to be prepared.

However, a calibration curve that is suitable for determining the concentration of a given microorganism, or type of microorganism may be provided when performing the methods of the present invention, and it may therefore be preferred that separate calibration curves are prepared for different microorganisms or microorganism types having different characteristics, e.g. different growth patterns. Thus, this need not necessarily be at the level of a particular genus or species of microorganism but may depend, for example, on the morphology and/or growth pattern of the microorganism.

The suitability of a calibration curve for use in determining the concentration of intact microorganisms in a sample may in some cases depend on the identity of said microorganism, and will determine how accurately the calibration curve allows the concentration of intact microorganisms to be determined from an image analysis value. It may be possible, for example, that a single calibration curve generated using a particular microorganism may suitable for determining the concentration of a range of different microorganisms, e.g. microorganisms within a single family or genus, and in this way it may only be necessary to prepare a single calibration curve for use in the methods of the present invention. Alternatively, a calibration curve for this purpose may be prepared using imaging data obtained from microorganisms from different families, genera, species or strains, and/or different microorganisms having similar characteristics and/or morphologies, and data obtained therefrom may be combined to provide a single calibration curve.

For example, it may be possible to collect data from different species of non-clustering Gram-negative bacteria, thereby to prepare a calibration curve. A calibration curve thus prepared may therefore be used in determining the concentration of many different (suitable) microorganisms, i.e. microorganisms for which it proves a satisfactory (i.e. representative) correlation between the number of imaged objects and the concentration of microorganisms in a sample.

Alternatively, if a specific microorganism exhibits irregular or unusual properties, it may be necessary to generate separate calibration curve for that particular microorganism in order to determine the concentration of that microorganism in a sample.

A number of different calibration curves, each suitable for use in the determination of the concentration of a different selection of microorganisms, may therefore be provided (i.e. prepared prior to performing the concentration determination method of the present invention). Thus, for example, separate calibration curves may be provided for non-clustering Gram-negative bacteria, non-clustering Gram-positive bacteria, clustering Gram-negative bacteria or yeast. A suitable calibration curve may therefore be selected in order to determine the concentration of a particular microorganism in a sample. Thus, 2, 3, 4, 5 or 6 or more different calibration curves may be prepared, and a suitable calibration curve selected therefrom once imaging of the microorganisms in the sample has been performed.

In a preferred embodiment of the invention, information obtained in imaging step (d) may inform the selection of which calibration curve is to be used in order to determine the concentration of viable microorganisms in a particular sample. One or more of the parameters of objects described above (i.e. maximum intensity, modal intensity and/or area or a derived value of the objects as described above) may be determined for the objects detected in step (d), optionally after background subtraction and/or thresholding steps, and such information may be used to select a suitable calibration curve for that sample. Preferably, a calibration curve is used which is predetermined for clustering or non-clustering microorganisms.

Factors such as the nature of a sample, the medium in which the microorganisms are provided, and the conditions under which the sample is stored or incubated may also all affect the relationship between the concentration of microorganisms in a sample and the number of objects imaged in step (c) of the present method, and thus a calibration curve is preferably prepared under similar or the same conditions as those under which a the aliquot-stain mixture is imaged.

As noted above, the sample may be any sample containing or suspected of containing microbial cells, and may comprise further components (which components may prevent accurate testing of microbial cells present in the sample) that it may be desirable to remove from the sample. A sample may typically be, or may comprise, a biological sample or alternatively expressed a sample may comprise biological material. In particular, the sample may comprise biologically-derived non-microbial (e.g. cellular) material. The sample may thus be an environmental sample, such as a water sample (e.g. waste water), sewerage effluent, soil sample or suspension, food sample (such as fruit or vegetable juice, meat, fruit, vegetables or dairy products) or homogenate thereof, or a medical or clinical sample.

The microorganism may be any microorganism (e.g. any bacterial or fungal microorganism, or protozoa, as discussed further below), in particular any pathogenic microorganism or any microorganism causing an infection in the body, and thus the method of the invention may in particular be used to determine the concentration of microorganisms in the context of detecting or diagnosing a microbial infection in or on any part of the body of a test subject (i.e. any microbial infection).

Thus, in a preferred embodiment, the sample is or comprises a clinical sample. A clinical sample may be any sample that may be obtained from a test subject, which generally will be a human patient but may be any human or animal, generally mammalian, subject. It may thus be any sample of body tissue, cells or fluid, or any sample derived from the body, e.g. a swab, washing, aspirate or rinsate etc. Suitable clinical samples include, but are not limited to, blood, serum, plasma, blood fractions, joint fluid, urine, semen, saliva, faeces, cerebrospinal fluid, gastric contents, vaginal secretions, mucus, a tissue biopsy sample, tissue homogenates, bone marrow aspirates, bone homogenates, sputum, aspirates, respiratory samples, wound exudate, swabs and swab rinsates e.g. a nasopharyngeal swab, other bodily fluids and the like. In a preferred embodiment, the clinical sample is sample is blood or a blood-derived sample, e.g. serum or plasma or a blood fraction.

The nature of the clinical sample may be determined according to the presentation of symptoms of the infection or suspected infection, or the general clinical condition of the subject. Although any microbial infection is encompassed, the method of the invention has particular utility in the course of detection or diagnosis of sepsis (or more generally management of sepsis), or where sepsis is suspected. Thus the clinical sample may be from a subject having, or suspected of having, or at risk of, sepsis. In such a case the sample will generally be blood or a blood-derived sample. Typically, for sepsis the sample will be, or will comprise, blood, but it is not precluded that other types of sample, such as those listed above.

The clinical sample may be introduced to a culture vessel comprising culture medium. This is a standard step which may be carried out according to standard procedures well known in the art and widely described in the literature. The clinical sample may thus be subjected to culture and thus the sample used in the method may a clinical sample culture, or, as described in more detail below, it may be a sample comprising microorganisms recovered, or isolated, from clinical sample culture.

A clinical sample may be collected in a vessel containing culture medium suitable for culturing microbial cells. In one aspect of the present invention, a clinical sample (e.g. a blood sample) may be collected in a culture flask containing culture medium, and optionally cultured prior to recovery of the microbial cells. It may in some embodiments be desirable to introduce a clinical sample into a culture flask and immediately or after only a short period of culture to remove an aliquot of the clinical sample/culture medium mixture from the flask for testing (e.g. for microbial ID), whilst subjecting the culture flask to continued culture, before further testing (e.g. AST testing). Such a method is described in our co-pending application WO 2015/189390.

A culture vessel can include any vessel or container suitable for the culture of microbial cells, e.g. a plate, well, tube, bottle, flask etc. Conveniently, where the clinical sample is blood or a blood derived sample the culture vessel is a blood culture flask, for example a BacT/ALERT (Biomerieux) blood culture flask, a Bactec blood culture flask (Becton Dickinson) or VersaTrek blood culture flask (Thermo Fisher), or indeed any tube, flask or bottle known for the sampling of blood, particularly for the purpose of culture to detect microorganisms. The sample may, therefore, be a blood culture sample.

Conveniently the culture vessel may be provided with the culture medium already contained therein. However, the culture medium may be separately provided and introduced into the culture vessel, either prior to, simultaneously with, or after the clinical sample has been added.

The culture medium may be any suitable medium and may be selected according to the nature of the clinical sample and/or the suspected microorganism, and/or clinical condition of the subject etc. Many different microbial culture media suitable for such use are known. Typically the culture medium may contain sufficient nutrients to promote rapid growth of microorganisms, as is known in the art. In many cases appropriate media are complex growth media comprising media such as Muller-Hinton (MH) media, MH—fastidious (MHF), Muller-Hinton supplemented with lysed horse blood, Lysogeny broth (LB), 2X YT Media, tryptic soy broth, Columbia broth, brain heart infusion broth, Brucella broth, as well as general purpose growth media known in the art, and may include the addition of particular growth factors or supplements. The culture may or may not be agitated. Culture media are available in various forms, including liquid, solid, and suspensions etc. and any of these may be used, but conveniently the medium will be a liquid medium. Where the culture vessel is a ready to use blood culture flask, as described above, these vessels may contain specified media especially modified to allow a wide range of microorganisms to grow. Typically medium supplied in a blood culture flask by a manufacturer will contain an agent or additive to neutralise the presence of any antibiotics present in a clinical sample taken from a test subject. Flasks containing or not containing such neutralising agents may be used, and neutralising agents may be added to the culture vessel if desired.

In a particular aspect of the present invention, the clinical sample is blood or a blood-derived sample, and is collected in a blood culture flask (BCF). Examples of blood culture flasks include a BacT/ALERT (Biomerieux) blood culture flask, a Bactec blood culture flask (Becton Dickinson) or VersaTrek blood culture flask (Thermo Fisher), or indeed any tube, flask or bottle known for the sampling of blood, particularly for the purpose of culture to detect microorganisms.

A sample according to the invention may accordingly comprise a clinical sample in a culture medium. Further the sample may be a clinical sample culture (i.e. a clinical sample which has been cultured for a period of time). It will be seen in this respect that the sample which is subjected to the method of the invention may be a portion of a complex sample which is collected or prepared. Thus the sample of the method of the invention may in one embodiment be an aliquot (e.g. a test aliquot) taken or removed from the sample e.g. from the contents of a culture vessel (flask) containing a clinical or other sample, whether before, during or after a period of culture (i.e. incubation). Furthermore, as described in greater detail below, the concentration determination method of the present invention may be used to determine the concentration of microorganisms in a preparation (e.g. a suspension) of microorganisms recovered from said clinical sample or clinical sample culture. Thus, the sample may be a sample containing recovered microorganisms. In one particular embodiment the present invention comprises the recovery of microbial cells from a clinical sample culture, e.g. a blood culture flask, preferably wherein a clinical sample has been cultured for a period of time in a blood culture flask, and thus provides a method of determining the concentration of microbial cells in a sample recovered from such a clinical sample culture.

In one embodiment, therefore, the sample used in step (a) may be a culture of a clinical sample which has been designated as positive for microbial growth (e.g. in a clinical sample culture system). Thus it may be a positive blood culture flask. However, it is not necessary according to the methods of the present invention for the clinical sample culture to be designated as positive and such a clinical culture sample may be used at a stage before it has been designated as positive, e.g. when it has been cultured for a period of time less than that necessary for it be indicated as positive. Thus the sample may be a non-positive blood culture flask (e.g. a blood culture flask which contains fewer microbial cells than is required for the flask to be designated as positive, or which has been cultured for a shorter period of time). Indeed, in the case of some clinical samples, a sample of the clinical sample culture may be withdrawn and used in the methods of the invention before any culture has taken place (e.g. when the clinical sample culture is set up). Advantageously, however, rather than using such a positive or non-positive clinical sample culture directly in the concentration determination method, the sample used in step (a) is a sample containing microorganisms recovered, or isolated, from such a clinical sample culture, e.g. a suspension or preparation comprising such recovered microorganisms.

In an alternative embodiment, a sample may be prepared as per the EUCAST standard method for determining MICs of antimicrobial agents mentioned above. In particular such a sample may be as prepared for use in a conventional AST method, but may be used in the AST method of the present invention as described herein. Microbial cells (e.g. from a clinical sample culture) may be plated to obtain isolated colonies, and the resulting colonies may be collected and used to prepare a microbial cell suspension for use to prepare an inoculum for the AST test microbial cultures. Such a suspension may be the sample used in step (a). Alternatively, the isolated individual colonies may be used to inoculate a culture medium which may be cultured to provide the inoculum. Such a culture may be the sample used in step (a).

As noted above, the concentration determination method of the present invention may be performed to determine the concentration of microorganisms in a sample containing microorganisms recovered from a sample as defined herein (i.e. microorganisms recovered from any sample mentioned above, but in particular a clinical sample or clinical sample culture). In other words, the 'sample' of the invention may be a recovered microorganism sample. Samples mentioned above may contain components which may interfere in some way with the preparation, handling and culture of microbial cells, e.g. by preventing the concentration of intact microorganisms in a sample to be accurately determined, affecting microbial viability or inhibiting microbial growth. It may, therefore, be advantageous to recover microorganism within such a sample, in order to separate the microorganisms from any such components. Once the microorganism has been recovered, the concentration of microorganisms in the recovered microorganism sample may be determined. In a particular embodiment, the recovered microorganism sample may be used to provide microorganisms for an AST assay described herein. The concentration determination method, and the AST method described herein may therefore be performed on, and using, a recovered microorganism sample.

The recovery of microorganisms from a sample may be particularly advantageous when the sample is a clinical sample, or clinical sample/culture medium mixture. Microbial cells may be recovered from a clinical sample/culture medium mixture before, during or after a period of culture. Culture medium provided in a culture flask, e.g. a blood culture flask may contain components which neutralise the effects of antimicrobial compounds, e.g. by adsorption to reduce their efficacy and/or concentration in the sample, and/or compounds such as Sodium Polyanethole Sulfonate (SPS) which inhibit the antimicrobial activity of components of a subject's innate immune system (e.g. complement or other factors) that might be present in the sample. Recovery of microbial cells from culture medium containing compounds such as these may therefore be desirable.

The recovery of microorganisms from a sample may be performed by the selective isolation of microbial cells from, or enrichment of microbial cells in, a sample. "Enrichment" means any method of increasing the concentration of microbial cells within a sample, or removing or otherwise reducing the concentration of any non-microbial components (e.g. non-microbial cells) from the sample. In the present context, enrichment may comprise both the removal of cells which derive from the subject under test (e.g. mammalian cells) from a sample, and isolation of the microbial cells therefrom. Thus, microbial cells may be separated from a sample, e.g. from a clinical sample culture (or more particularly from an aliquot thereof), and may be subjected to a concentration determination step according to the present invention, particularly in the context of an AST assay to determine antimicrobial susceptibility.

Suitable methods for recovering microorganisms from a sample may include selectively lysing any non-microbial cells present, and/or selectively recovering microbial cells (i.e. positive or negative selection of microbial cells in the sample). Procedures and reagents for lysis of non-microbial cells and the isolation of microbial cells from mixtures comprising non-microbial cells are commercially available, for example from Molzym or Biocartis. Other lysis conditions and methods are widely described in the art, for instance, in Sullivan et al. 1975, J Clin Microbiol 1, 30-36; Zierdt et al. 1977 J Clin Microbiol 5, 46-50.

Recovery may therefore comprise the removal from the sample of any non-microbial eukaryotic cells. This may, for example, comprise the removal of any cells which derive from a subject under test, where the sample is a clinical sample. This may be done under any conditions which lyse non-microbial eukaryotic cells, preferably mammalian cells, but which do not lyse microbial cells, and preferably which maintain the viability of the microbial cells. For example, an appropriate lysis reagent, e.g. a lysis buffer, may be added to the sample to achieve selective lysis of undesired cells. The selective lysis of non-microbial cells allows the microbial cells to be separated from other components that may be present in the sample. The lysis reagent thus is capable of selectively lysing cells (e.g. mammalian cells) e.g. by solubilising cell membranes. The lysis reagent may comprise one or more detergents, one or more chaotropes, one or more enzymes, or any combination thereof. Different components of the selective lysis reagent may be contacted with the sample as a single lysis reagent, or different components (e.g. a detergent containing lysis buffer and one or more enzymes) may be contacted with the sample separately, sequentially or simultaneously. Such contacting may be by adding the sample to the reagent/reagent components or vice versa.

The term "lysing" means breaking down of a cell. In particular, the cell is broken down to release cell contents., This may be achieved by any means, as vast number of which are known in the art, for example by viral, enzymatic, mechanical, electrical, chemical, heat, cold or osmotic mechanisms that compromise cell integrity leading to the partial or full release of cellular components into surrounding solution.

The term "selectively lysing" or "selective lysis" means lysing of a particular subset of the cells present in a sample. In the present case it is desirable to selectively lyse only the non-microbial cells, or more particularly the cells which derive from the subject under test (e.g. mammalian cells) that are present in a clinical sample, without substantially lysing the microbial cells present in a clinical sample. In addition, it is desirable according to certain methods of the present invention that the microbial cells obtained from the sample are able to grow and reproduce (growth is required in order to determine antimicrobial susceptibility), and thus it is desirable that the ability of the microbial cells to grow and/or reproduce (viability) is not affected by the selective lysis of the non-microbial or test subject-derived cells that are present in a sample.

Preferably all (i.e. 100%), or substantially all of the microbial cells recovered from a sample may be viable following any such treatment, and it is preferred that at least 99%, 98%, 97%, 96%, 95%, 94% 93%, 92%, 91% or 90% or microbial cells recovered from a sample are viable following the selective lysis step.

However, as the methods of the present invention require the concentration of intact or viable microorganisms in the recovered microorganism sample to be determined, antibiotic susceptibility may still be assessed in the event that at least 80%, 70%, 60%, 50%, 40%, 30%, 20% or 10% of the recovered microbial cells are intact or viable. Thus, such methods are not limited to any particular level of microbial viability or recovery.

Methods for selectively lysing non-microbial cells for selectively enriching microorganisms in a sample, which are not dependent on knowing the identity of the microorganisms, are described for example in US 2013/0171615, US 2012/0231446, US 2010/0184210, U.S. Pat. Nos. 7,893,251 and 8,481,265, and methods for selectively removing eukaryotic cells from a sample are described in US 2005/0202487.

Useful detergents may include one or more non-denaturing lytic detergents, such as Triton X100-R, Triton X-114, NP-40, Genapol C-100, Genapol X-100, Igepal CA 630, Aslasolve 200, Brij 96/97, CHAPS, octyl β-D-glucopyranoside, saponin and nonaethylene glycol monododecyl ether (C12E9, polidocenol). Optionally, denaturing lytic detergents can be included, such as sodium dodecyl sulphate (SDS), N-laurylsarcosine, dodium deoxycholate, bile salts, hexadecyltrimethylammonium bromide, SB3-10, SB3-12, amidosulphobetaine-14 and C7BzO. Optionally solubilisers can also be included, such as Brij 98, Brij 58, Brij 35, Tween 80, Tween 20, Pluronic L64, Pluronic P84, non-detergent sulphobetaines (NDSB 201), aphipols (PMAL-C8), and methyl-β-cyclodextrin. In one embodiment polyoxyethylene detergent detergents may be preferred. The polyoxyethylene detergent can comprise the structure $C_{12-18}/E_{9-10}$, wherein C12-18 denotes a carbon chain length of 12 to 18 carbon atoms and E9-10 denotes from 9 to 10 oxyethylene hydrophilic head groups. For example, the polyoxyethylene detergent can be selected from the group consisting of Brij 97, Brij 96V, Genapol C-100, Genapol X-100, nonaethylene glycol monododecyl ether (polidocanol), or a combination thereof and ethylene-diaminetetraacetic acid (EDTA).

The lysis solution may also comprise one or more enzymes. Enzymes that can be used in the lysis solutions include, without limitation, enzymes that digest nucleic acids and other membrane-fouling materials (e.g. proteinase XXIII, DNase, neuraminidase, polysaccharide, Glucanex and Pectinex, Proteinase K, Micrococcal nuclease, pepsin or trypsin).

Suitable chaotropes or chaotropic agents may include urea, guanidinium hydrochloride, butanol, ethanol, lithium perchlorate, lithium acetate, phenol, propanol or thiourea.

In another embodiment, one or more additional agents can be used, including for example reducing agents such as 2-mercaptoethanol or dithriothreitol (DTT), stabilising agents such as magnesium, pyruvate and humectants, and/or chelating agents such as ethylenediaminetetraacetic acid (EDTA).

The lysis reagent can be buffered at any pH that is suitable to lyse the desired cells, and will depend on multiple factors, including without limitation, the type of sample, the cells to be lysed, and the detergent used. In some embodiments, the pH can be in a range from 2-13, e.g. 6-13, 8-13, or 10-13. Suitable pH buffers include any buffer capable of maintaining a pH in the desired range, e.g. about 0.05 M to about 1.0 M CAPS.

Additionally, the lysis reagent may comprise any suitable salts, including NaCl, KCl, $MgCl_2$, $Na_2HPO_4$, $NaH_2PO_4$ which might aid lysis, or the subsequent handling of the microbial cells. Salts may, if present, be present at any suitable concentration, e.g. at least 0.01M, 0.02M, 0.05M, 0.1M, 0.2M, 0.5M, 1M, 2M or 5M, depending on the factors such as the volume of buffer and sample used.

Alternatively, rather than selectively removing non-microbial cells, microbial cells may positively be selected from the test aliquot. For example if the identity of the microorganism is known microbial cells may be selected by binding to immobilised or immobilised double ligands (affinity binding partners) capable of specifically or selectively binding to the microbial cells.

Following the removal (e.g. lysis) of the non-microbial cells from a test aliquot, the microbial cells may be recovered from the resulting mixture (e.g. lysate). Although in one embodiment the separation and recovery steps may be seen as one and the same (e.g. the method may be performed in such a way that microbial cells are selectively separated from the test aliquot, or recovery is performed by lysis of non-microbial cells), in a preferred embodiment microbial cells are recovered from the lysate as a separate step, i.e. they are physically recovered from the sample after the lysis step. This may be done in any convenient way, e.g. by filtration or centrifugation.

Thus, following recovery of the microbial cells from the sample the recovered cells are resuspended, thereby to provide a recovered microbial sample. Resuspension may be performed using a culture medium, suitable for microbial cell growth, or alternatively may be performed using a buffer or any other suitable medium.

In a preferred embodiment of the present invention, the microbial cells are recovered from the sample by filtration, and are resuspended from the filter directly using culture medium. Advantageously recovery may be performed by filtration using a filter comprising a suitable pore size to capture any microbial cells whilst allowing the flow-through of any other components of the sample e.g. culture medium and/or lysed mammalian cell debris and fragments. Following filtration the microbial cells recovered on the filter may optionally be washed using culture medium or any suitable wash buffer comprising one or more components as defined above for the lysis buffer, e.g. a detergent. The cells may be resuspended from the filter by repeated pipetting to resuspend the cells from the surface of the filter. In a preferred embodiment of the invention liquid (e.g. culture medium or buffer) may be back-flushed through the filter (i.e. in the opposite direction to which the filtrate was filtered) in order to resuspend the microbial cells. Alternatively microbial cells may be retrieved by using the entire filter, e.g. either by adding culture media to the filter or contacting the filter with culture medium in a culture vessel.

Alternatively, recovery of the microbial cells following the removal of non-microbial cells may be performed by centrifugation i.e. to sediment the intact microbial cells from a suspension to form a pellet. The resulting supernatant may then be discarded. The microbial pellet may be resuspended in a suitable wash buffer, as defined above, and centrifuged a further time to form a pellet. Accordingly, in an embodiment, the sample in step (a) may be obtained by resuspending a pellet of microbial cells obtained by centrifugation. An alternative format is to recover microbial cells by using hollow fibres such as in US 7547526.

When culture medium is used to resuspend the microbial cells, the culture medium is generally speaking a culture medium which is approved or recognised for use in AST tests. Preferably, the culture medium is a liquid medium. Accordingly in one embodiment it is a Muller-Hinton (MH) medium or a Muller-Hinton Fastidious (MHF) medium or cation-adjusted Mueller Hinton medium (CAMHB). For non-standard AST any other medium commonly known may be used with the invention. MIC values obtained by performing an AST assay using a 'non-standard' culture medium may be adjusted (correlated) to give standard AST results.

Once the microbial cells have been recovered, e.g. following removal of the non-microbial cells from the sample, and the recovered microorganism sample has been obtained, the concentration of microbial cells present in the recovered microorganism sample is determined according to the methods of the present invention. In one particular embodiment, as noted above, this may be in particular with a view to performing an AST assay, i.e. the concentration of microorganisms may be determined before an AST assay is performed.

Advantageously, performing an AST assay using a recovered microorganism sample may allow a more rapid AST assay to be performed. In particular, by recovering microbial cells directly from a clinical sample or clinical sample culture, thereby to obtain a recovered microorganism sample, a homogeneous sample lacking any contaminants.

Certain samples, e.g. food or environmental sample in particular, may comprise particulate matter which it may be desirable to remove prior to determining the concentration of viable microorganisms in a sample. Additionally, certain commercially available culture vessels (e.g. blood culture flasks) are provided with resin beads, which resin neutralise the effect of any antimicrobial agents which are present in the clinical sample (i.e. which had been administered to the subject under test) in order to facilitate the growth of the microbial cells in culture. In a preferred embodiment, therefore, the sample may be filtered in order to remove any large particles that may be present in the sample. Preferably, this step of filtration will utilise a filter having a pore size which does not substantially remove any cellular matter from the test aliquot, but which can remove the particles, e.g. at least 100, 200 or 300 µm but could be up to 1000 µm.

The method of the invention may be used determining concentration of any microorganism. Generally speaking clinically relevant microorganisms are concerned, but the microorganism may be pathogenic or non-pathogenic. As used herein, the term microorganism encompasses any organism which may fall under the category of "microorganism". Although not necessarily so, microorganisms may be unicellular, or may have a unicellular life stage. The microorganism may be prokaryotic or eukaryotic and generally will include bacteria, archaea, fungi, algae, and protists, including notably protozoa. Of particular interest are bacteria, which may be Gram-positive or Gram-negative or Gram-indeterminate or Gram-non-responsive, and fungi, e.g. yeast.

The bacteria may aerobic or anaerobic, although in a particular embodiment, especially where the AST method of the invention is concerned, the bacteria are aerobic. The bacteria may be, or may include, mycobacteria.

Particularly, clinically relevant genera of bacteria include *Staphylococcus* (including Coagulase-negative *Staphylococcus*), *Clostridium*, *Escherichia*, *Salmonella*, *Pseudomonas*, *Propionibacterium*, *Bacillus*, *Lactobacillus*, *Legionella*, *Mycobacterium*, *Micrococcus*, *Fusobacterium*, *Moraxella*, *Proteus*, *Escherichia*, *Klebsiella*, *Acinetobacter*, *Burkholderia*, *Entercoccus*, *Enterobacter*, *Citrobacter*, *Haemophilus*, *Neisseria*, *Serratia*, *Streptococcus* (including Alpha-hemolytic and Beta-hemolytic Streptococci), *Bacteriodes*, *Yersinia*, and *Stenotrophomas*, and indeed any other enteric or coliform bacteria. Beta-hemolytic *Streptococci* would include Group A, Group B, Group C, Group D, Group E, Group F, Group G and Group H Streptococci.

Non-limiting examples of Gram-positive bacteria include *Staphylococcus aureus*, *Staphylococcus haemolyticus*, *Staphylococcus epidermidis*, *Staphylococcus saprophyticus*, *Staphylococcus lugdunensis*, *Staphylococcus schleiferi*, *Staphylococcus caprae*, *Staphylococcus pneumoniae*, *Staphylococcus agalactiae* *Staphylococcus pyogenes*, *Staphylococcus salivarius*, *Staphylococcus sanguinis*, *Staphylococcus anginosus*, *Streptococcus pneumoniae*, *Streptococcus pyogenes*, *Streptococcus mitis*, *Streptococcus agalactiae*, *Streptococcus anginosus*, *Streptococcus equinus*, *Streptococcus bovis*, *Clostridium perfringens*, *Enterococcus faecalis*, and *Enterococcus faecium*. Non-limiting examples of Gram-negative bacteria include *Escherichia coli*, *Salmonella bongori*, *Salmonella enterica*, *Citrobacter koseri*, *Citrobacter freundii*, *Klebsiella pneumoniae*, *Klebsiella oxytoca*, *Pseudomonas aeruginosa*, *Haemophilus influenzae*, *Neisseria meningitidis*, *Enterobacter cloacae*, *Enterobacter aerogenes*, *Serratia marcescens*, *Stenotrophomonas maltophilia*, *Morganella morganii*, *Bacteriodes fragilis*, *Acinetobacter baumannii* and *Proteus mirabilis*.

Clinically relevant fungi may include yeasts, particularly of the genus *Candida*, and fungi in the genera *Aspergillus*, *Fusarium*, *Penicilium*, *Pneumocystis*, *Cryptococcus*, *Coccidiodes*, *Malassezia*, *Trichosporon*, *Acremonium*, *Rhizopus*, *Mucor* and *Absidia*. Of particular interest are *Candida* and *Aspergillus*. Non-limiting examples of fungi include *Aspergillus fumigatus*, *Candida albicans*, *Candida tropicalis*, *Candida glabrata*, *Candida dubliensis*, *Candida parapsilosis*, and *Candida krusei*.

Non-limiting examples of clinically relevant protozoa include *Entamoeba histolytica*, *Giardia lamblia*, *Trypanosoma brucei*, *Besnoitia besnoiti*, *Besnoitia bennetti*, *Besnoitia tarandi*, *Isospora canis*, *Eimeria tenella*, *Cryptospotidium parvum*, *Hammondia heydorni*, *Toxoplasmosis gondii*, *Neospora caninum*, *Hepatozoon canis*, *Plasmodium falciparum*, *Plasmodium vivax*, *Plasmodium ovale*, *Plasmodium malariae* and *Plasmodium knowlesi*.

As noted above, the concentration determination method of the present invention has particular utility in determining the concentration of intact (and therefore viable) microorganisms in a sample in the context of performing an AST assay, and in particular in the context of determining the concentration of microorganisms in an inoculum therefor. The present invention therefore provides a method for determining the antimicrobial susceptibility of a microorganism, said method comprising determining the concentration of viable microorganisms in a sample as outlined above, and performing an AST assay.

Advantageously, the invention may provide a method which starts from a clinical sample or clinical sample culture, and which comprises the recovery (or isolation) of viable microorganisms from a clinical sample or clinical sample culture, the determination of the concentration of intact (and hence indicative of viable) microorganisms in a suspension of the recovered microorganisms, and optionally the preparation of an inoculum from the suspension (which may comprise the adjustment of the concentration of microorganisms in the suspension or a portion or aliquot thereof). The suspension of recovered microorganisms or an inoculum prepared therefrom may be used as the inoculum for the AST microbial test cultures which are prepared in the AST assay.

The AST assay may, as described further below, be performed in any convenient or desired way. Accordingly, microbial growth may be assessed (or determined) in the presence of different antimicrobial agents (e.g. antibiotics) and/or amounts or concentrations of antimicrobial agent (e.g. antibiotic). Growth may be assessed directly or by assessing (determining) markers of growth.

Generally speaking, an AST assay is performed by monitoring the effect of an antimicrobial agent on microbial growth. A sample containing microorganisms is used to inoculate culture medium in a series of at least two culture vessels (i.e. to set up at least two AST microbial test cultures), each comprising a different concentration of an antimicrobial agent, and the microorganisms are cultured for a period of time. In this way, a series of at least two different concentrations of an antimicrobial agent is tested in order to determine the minimum inhibitory concentration (MIC) that is required in order to prevent microbial growth. The MIC value obtained thus provides an indication of whether a microorganism is resistant or susceptible to an individual antimicrobial agent.

In addition to inoculating at least two AST microbial test cultures comprising different concentrations of antimicrobial agents, an AST assay will have a positive control condition (culture medium that does not comprise an antimicrobial agent) in order to confirm that the microorganism is viable and is capable of growth in the growth medium provided for the AST assay, and a negative control condition (culture medium which has not been inoculated with a microbial culture and which does not comprise an antimicrobial agent) in order to confirm that the growth medium is not contaminated with a microorganism that is not obtained from the clinical sample. Thus, step (iii) of the method for determining the antimicrobial susceptibility of a microorganism in a sample may generally will include setting up suitable positive and negative control conditions, in addition to the at least two different growth conditions.

The positive control sample may be seen in some embodiments as providing a first concentration of an antimicrobial agent (i.e. a concentration of 0 M), and only a second condition comprising an antimicrobial agent may be set up. In such an embodiment, the growth in the positive control condition and the condition comprising an antimicrobial agent may be assessed in order to determine antimicrobial susceptibility. Thus "at least two different growth conditions, wherein . . . each antimicrobial agent is tested at two or more different concentrations" may be seen to encompass an embodiment in which an antimicrobial agent is added to only a single growth condition, and the positive control condition represents a second concentration of the antimicrobial agent.

In a preferred aspect, more than one (i.e. two or more) different antimicrobial agent is tested, thus providing two or more different MIC values, one for each different antimicrobial agent. The combination of different MIC values provides the antimicrobial susceptibility profile of a given microorganism, i.e. which of a panel of antimicrobial agents a microorganism is resistant to, and which of a panel of antimicrobial agents a microorganism is susceptible to. Separate positive and negative control conditions may be set up for each separate antimicrobial agent that is tested, if required, however a single positive and a single negative control condition will suffice where multiple different antimicrobial agents are tested.

Microbial growth in the AST method may be assessed by any desired or suitable means, including by any means known in the art. More particularly, microbial growth may be assessed by determining the amount and/or number and/or size of microorganisms and/or microbial colonies or aggregates. As will be discussed in more detail below, in certain preferred embodiments, microbial growth is assessed (determined) by imaging, or alternatively expressed, by visualising the microorganisms. Thus microbial cells, which may include aggregates or clumps (clusters) of cells, or microbial colonies, may be visualised or imaged as a means of determining (or assessing or monitoring) growth. This may include counting of cells or colonies, but is not limited to such methods and includes any means of visually assessing the amount of microbial growth by assessing (or determining) the size, area, shape, morphology and/or number of microbial cells, colonies or aggregates (the term "aggregate" includes any collection of cells in physical proximity e.g. a clump or cluster; this may include non-clonal clumps/clusters of cells which have aggregated or stuck together (e.g. neighbouring cells which have become aggregated) as well as clonal colonies). The parameter used to measure microbial growth may, but need not, vary according to the identity of the microbe and the antimicrobial agents used. Indeed, depending on the organism and the antimicrobial agents used, the morphology or growth pattern of the cells may be affected, and this may be altered or changed from the "normal" or "typical" morphology or growth pattern, e.g. in the absence of the antimicrobial agent. Whilst some AST growth monitoring methods may depend on detecting such changes, it is not essential according to the present invention to take such changes into account and the amount (e.g. area) of microbial growth or biomass may be determined irrespective of morphology and/or growth pattern. Thus the same growth monitoring method may be used regardless of the microbial cell and/or antimicrobial agents used. Methods for performing the AST assay are described further below.

The present invention provides a method of determining the concentration of intact, or viable, microorganisms in a sample, and this information can be used to accurately provide a particular concentration of microbial cells in the test microbial cultures. For instance, the concentration of microorganisms in at least a portion of the sample may be adjusted once the concentration has been determined, in order to provide an inoculum for inoculating the test microbial cultures in step (iii). Thus, the concentration of microbial cells in the sample may optionally, or if necessary, be adjusted, e.g. to fall within a range suitable for use in an AST assay. This adjustment may not be required in every instance, i.e. the sample may be used directly to inoculate the series of test microbial cultures that are set up in step (iii) (i.e. the sample may be used directly, i.e. without any further adjustment). Alternatively, the sample (or an aliquot thereof) maybe adjusted to a desired or pre-determined concentration. Still further alternatively the sample may be used directly (i.e. without adjustment) to inoculate the series of test microbial cultures, and the concentration of microorganisms in the test microbial cultures may be adjusted, if necessary, to a desired or pre-determined concentration. Any such adjustment will be based on the concentration of viable microorganisms determined in the concentration determination method (i.e. based on the concentration of microorganisms in the sample).

Thus, the concentration of microbial cells in the sample or portion thereof and/or in the test microbial cultures may be adjusted. More particularly the concentration may be adjusted to increase or to decrease the number, or concentration, of microbial cells.

In one embodiment, the microorganism concentration may be adjusted in at least a portion of the sample, to provide an inoculum for inoculating the test microbial cultures in step (iii). Thus for example the concentration of microbial cells in the inoculum may be increased e.g. by culturing the sample for a period of time to allow the microbial cells to grow, or decreased e.g. by dilution prior to inoculating the test microbial cultures, or in the course of inoculating the test microbial cultures e.g. by selecting an appropriate amount (e.g. volume) to be used to set up the test cultures, either by adding to solid (e.g. freeze-dried antibiotics) or by dilution when a portion or aliquot of the inoculum is added to a volume of antibiotic and/or culture medium for the AST test. Accordingly the test microbial cultures may be inoculated with the sample (or aliquot thereof) or with an adjusted (e.g. diluted) inoculum therefrom.

In one embodiment, wherein the sample comprises a microbial concentration that is too high to be used in an AST assay, the microbial culture may be diluted using an appropriate buffer or culture medium (e.g. liquid culture medium) in order to reduce the cell density to a suitable level for an AST to be performed. Preferably the dilution is performed using the culture medium which is to be used to perform the AST assay. In one embodiment this may be performed using a Muller Hinton (MH) broth. Adjusting the concentration may, for example, comprise a dilution based on the concentration determined in step (ii) of the AST method.

In an alternative embodiment, wherein the sample comprises a microbial concentration that is too low to be used in an AST assay, the sample may be cultured (or further cultured) for a period of time in order to allow the microorganisms present therein to grow and increase in number. The concentration of microbial cells present in the sample may be monitored either continuously or at a series of individual time points until the concentration of microorganisms reaches a sufficiently high cell density that an AST assay may be performed (i.e. that step (iii)). Growth of the microbial culture at this stage may be monitored by any of the methods described herein for monitoring growth in the AST assay itself, e.g. imaging or counting of cells or colonies, and/or the concentration determination method of the present invention may be performed following a period of growth.

Thus, in one embodiment the present invention utilises an inoculum (e.g. sample or diluted sample) having a standard microbial concentration (e.g. 0.5 McFarland units or $10^8$ CFU/ml), or a concentration in the region thereof, in order to inoculate the test cultures used in an AST assay. The concentration of microbial cells present in the sample may optionally, or if necessary be adjusted, that is increased or decreased depending on the number of cells present in the sample, in order to obtain a sample having a standard concentration. Alternatively, the concentration of microbial cells present in the sample may lie within a standard range, without the need for an adjustment step to be performed. Regardless, the concentration of microbial cells present in the sample is determined by the method of the present invention, and may be adjusted as and if required to obtain a sample having a standard concentration. Alternatively, the sample may be used without adjustment and the concentration of microbial cells in the test microbial cultures may be adjusted (e.g. by selecting an appropriate dilution factor for setting up the test culture or an appropriate volume), based on the concentration of microorganisms determined in the sample.

AST assays typically utilise microbial cultures having set (or standard or standardised) cell densities or microbial concentrations in order to allow results obtained from one sample or in one location to be compared with those obtained elsewhere, as the response of microorganisms to antimicrobial agents is known to vary with the concentration of microorganisms in a sample, as well as the type and concentration of the antimicrobial agent itself. Factors influencing clinical outcomes such as the dosage of an antimicrobial agent and the treatment regime prescribed to a patient are based on results obtained from AST assays performed according to set standard criteria.

The results obtained in an AST assay performed using a 'non-standard' (or "non-standardised") microbial culture (the antimicrobial susceptibility profile of a microorganism, or a set of MIC values) may differ from the results obtained in an AST assay performed according to standard criteria, e.g. using a 'standard' microbial culture. However, the degree to which a MIC value obtained using a non-standard microbial culture varies from a MIC value obtained using a standard microbial culture may be determined, if the concentration of microbial cells in the sample or inoculum used to inoculate the AST test cultures is known. It is thereby possible to calculate a theoretical 'standard' MIC value from an MIC value obtained using a non-standard microbial culture.

The degree to which the MIC value obtained using a non-standard microbial culture varies from a 'standard' MIC value may vary depending on the nature of the microorganism and the antimicrobial agent, and can be determined separately, e.g. for each different antimicrobial agent that is tested and for microbial cultures comprising different concentrations of microbial cells.

The present invention thus provides a method to determine the antimicrobial susceptibility profile of a microorganism using an inoculum comprising a non-standard concentration of microbial cells, wherein the concentration of microbial cells in the test microbial cultures is measured (indirectly, by measuring the concentration of microbial cells in the sample used to inoculate said test microbial cultures or to prepare the inoculum) before the AST assay is performed (i.e. the concentration of microbial cells in the sample is determined, and the MIC value obtained in the AST assay may be adjusted based on the concentration of microbial cells in the test microbial cultures prepared therefrom to give a standard MIC value.

As described above, the standard inoculum used to set up an AST test assay in the methods of the prior art typically is approximately 0.5 McFarland units. As mentioned above, this corresponds to approximately $10^8$ CFU/ml. This is typically diluted in a 1:200 dilution to provide test microbial cultures comprising approximately $5\times10^5$ CFU/ml. However, whilst the methods of the present invention may use these standard values, and it is generally preferred for the concentration of microorganisms in the inoculated microbial test cultures in the AST test to be in the range of $4.5\times10^5\pm80\%$ or $5\times10^5\pm60\%$, it is possible in the methods of the present invention for the inoculum (e.g. the sample and the inoculum prepared therefrom) and/or the test microbial cultures to comprise any defined or pre-determined concentration of microbial cells, provided the concentration of microbial cells in the test microbial cultures that are used to obtain an AST value is known. Thus, in other embodiments the concentration of microorganisms in the inoculated microbial test cultures in the AST test may be in the range of $1\times10^5\pm80\%$ or $5\times10^4\pm80\%$, or $5\times10^4\pm60\%$, etc.

The concentration of microbial cells in the sample may therefore be any desired or pre-determined concentration that is suitable for setting up a microbial test culture in an AST method. It may therefore be at least 10, $10^2$, $10^3$, $10^4$, $10^5$, $10^6$, $10^7$, $10^8$, $10^9$, $10^{10}$, $5\times10^{10}$ or $10^{11}$ CFU/ml. Preferably the concentration of microbial cells in the sample will be $10$-$10^{11}$, $10^2$-$10^{11}$, $10^3$-$10^{11}$, $10^4$-$10^{11}$ CFU/ml, $10^5$-$10^{11}$ CFU/ml, $10^6$-$10^{11}$ CFU/ml, $10^7$-$10^{11}$ CFU/ml, $5\times10^6$-$10^{11}$ CFU/ml, $2\times10^6$-$10^{11}$ CFU/ml, $10^6$-$10^{11}$ CFU/ml, $5\times10^6$-$5\times10^{10}$ CFU/ml, $2\times10^6$-$5\times10^{10}$ CFU/ml, or $10^6$-$5\times10^{10}$ CFU/ml.

The statistical reliability of an AST assay performed using an inoculum having a low concentration of microorganisms may be worse than in embodiments where the inoculum contains a higher concentration of microorganisms. Thus, in certain embodiments, if a particularly low concentration of microorganisms is determined in the sample, it may be desirable or advantageous not to continue with the AST assay at that stage. Thus, in certain embodiments, where the concentration of microorganisms in the sample is below $1\times10^3$ CFU/ml, or more preferably below $1\times10^4$, $1\times10^5$ or $1\times10^6$ CFU/ml, the AST assay may not be performed with the sample (i.e. the AST method is not performed beyond step (ii)). Optionally, the concentration of microorganisms in the sample may be allowed to increase before the concentration determination method is repeated (e.g. following a period of culture), and if the sample contains a sufficiently high concentration of microorganisms at this later stage, it may be possible to then proceed with the AST assay.

The AST method of the invention, which allows non-standard concentrations to be used in the AST test, has particular utility if the concentration of microbial cells in the sample is below the standard concentration, as it may bypass the need to incubate said sample for a period of time in order to allow the concentration of microbial cells in the sample to increase, e.g. to a level above that of the standard concentration.

The AST method presented herein may be viewed as a method to determine the 'standard' antimicrobial susceptibility profile of a microorganism by adjusting the MIC values obtained by performing an AST assay using a non-standard microbial culture. Viewed another way, this provides a theoretical way to adjust the concentration of microbial cells that is used to inoculate the test cultures used in an AST assay, thereby to calculate the antimicrobial susceptibility of a microorganism.

Whilst it is possible to use a non-standard sample to inoculate the test cultures used in the present invention, in an alternative embodiment the present invention provides methods to physically adjust the concentration of microbial cells present in a sample and/or test microbial cultures so that the concentration of microbial cells in the test microbial cultures corresponds to a standard or standardised concentration, (e.g. about $5\times10^5$ CFU/ml) in order that a standard AST assay may be performed.

The sample, or an inoculum prepared therefrom, is used to inoculate the test microbial cultures. As discussed above, the sample may be added to culture medium, i.e. the sample may be diluted, or diluted further, at the stage of setting up the test microbial cultures (step (iii) of the AST method). Thus, the test microbial cultures may be adjusted at this point to comprise any desired or pre-determined concentration. Thus, the test microbial cultures will comprise an initial concentration of microbial cells of at least 10, $10^1$, $10^2$, $10^3$, $10^4$, $10^5$, $10^6$, $10^7$, $10^8$ or $10^9$ CFU/ml, preferably $10^2$-$10^8$, $10^3$-$10^7$ or $10^4$-$10^6$ CFU/ml. As noted above, the test microbial cultures may, therefore, be set up to a final concentration of $5\times10^4\pm80\%$, $1\times10^4\pm80\%$, $4\times10^5\pm80\%$, $4.5\times10^5\pm80\%$ or $5\times10^5\pm80\%$.

It is noted however that what constitutes a 'standard' sample may vary depending on the identity of the microorganism, i.e. the concentration of microbial cells present in the sample may depend on the identity of the microorganism. Preferably the concentration of microbial cells in the sample will be $10$-$10^{11}$, $10$-$10^{10}$, $10$-$10^9$, $10^2$-$10^9$, $10^3$-$10^9$, $10^4$-$10^9$ CFU/ml, $10^5$-$10^9$ CFU/ml, $10^6$-$10^9$ CFU/ml, $10^7$-$10^9$ CFU/ml.

Recognised and prescribed conditions for AST assaying exist, and may be followed in order that readily comparable results may be obtained which are comparable to, or may be compared with, tests performed in other laboratories.

This may involve for example the use of a prescribed medium and culture conditions. In certain embodiments, medium for microbial culture may be a liquid medium, i.e. the culture medium may be a liquid.

In certain embodiments it may be advantageous or desirable to set up test microbial cultures in parallel having different media for the growth of different microorganisms. This may be useful, for example, if the identity of the microorganisms in the sample is not known, or if their growth patterns or requirements have not been fully characterised. Thus for example, parallel microbial test cultures in the AST method may be set up which contain, or do not contain fastidious supplements in the growth medium, or in other words, parallel test microbial cultures in fastidious or non-fastidious media. Fastidious media are well known in the art and both pre-prepared fastidious media and fastidious supplements are widely and commercially available. Fastidious supplements included for example lysed blood preparations (e.g. lysed horse blood), serum, various vitamins and/or minerals, cofactors, etc., e.g. beta-nicotinamide. Conveniently, fastidious supplements may be added to culture media as part of a dilution protocol. Further, whether or not fastidious media or supplements are used may depend on the concentration of microbial cells which is determined for the sample. For example, if the concentration is low, e.g. if there is less than $2\times10^6$ CFU/ml microbial cells in the sample, the use of microbial test cultures with fastidious media/supplements may be omitted from the AST method.

In certain embodiments, it may also be advantageous to set up test microbial cultures in parallel having different media optimised for testing susceptibility to particular antimicrobial agents. Additives necessary for specific antibiotics may be included in test microbial cultures. For example, polysorbate 80 may be included, and/or an increased calcium concentration may be provided in certain test microbial cultures.

Microorganisms may be grown in the presence of a variety of antimicrobial agents to determine their susceptibility to a given antimicrobial agent. The antimicrobial agents may be selected based on the identity of the microorganism, if known, and preferably also on the nature of any genetic antimicrobial resistance markers identified within the microorganism. The antimicrobial agents, and the amounts to be used, may also be selected according to current clinical practice, e.g. according to which antimicrobial agents are currently used in practice to treat the identified microorganism, in order that the susceptibility of the microorganism to the currently accepted or recognised antimicrobial treatment of choice can be assessed.

Thus antimicrobial agents can be selected based on those known to be effective against the identified microorganism, or those currently used in practice to treat the microorganism, and excluding any agents to which resistance might be expected based on the presence of resistance markers, or such agents might be included and the amounts used might be selected to allow the determination of an amount or concentration of the antimicrobial agent that may be effective, despite the presence of the resistance marker. Antimicrobial agents are added to culture medium to a range of final concentrations or amounts. In one embodiment of the present invention a dilution of the antimicrobial agent may be performed. In a preferred format of the invention antimicrobial agents in pre-determined amounts, to yield pre-determined concentrations after being dissolved, are pre-deposited in wells where culture media with bacteria are added before the AST. The pre-deposited antimicrobial agents are preferably freeze-dried formulations.

The step of growing, or culturing, the sample/microorganisms therefrom in the AST assay may take place by any known or convenient means. Solid or liquid phase cultures may be used.

Thus for example, in one preferred embodiment, the microorganisms may be cultured on or in a plate or other solid medium, or in a vessel (e.g. a well of a plate) containing a liquid medium, containing the antimicrobial agent and microbial growth may be determined by visualising (e.g. imaging) the microorganisms (i.e. imaging the plate etc.) Thus, the culture is visualised or imaged directly as a means of monitoring or assessing growth. Accordingly in one preferred embodiment the cultures are analysed directly to monitor/assess growth. For example, the cultures may be grown in the wells of a plate, or compartments of a carrier substrate and the wells/compartments may be imaged.

Alternatively, samples (or aliquots) may be removed (or taken) from the AST test cultures, at intervals, or at different time points and the removed samples (aliquots) may be analysed for microbial growth. This may be done by any means, including for example by means of molecular tests, e.g. nucleic acid based tests, Thus detection probes and/or primers may be used which bind to the microbial cells or to components released or separated from microbial cells. This may include for example nucleic acid probes or primers which may hybridise to microbial DNA. In other embodiments, microbial cells may be detected directly, e.g. by staining, as described in more detail below.

Each antimicrobial agent is used at at least two concentrations, in addition to a positive control in which the microorganism is allowed to grow in the absence of any antimicrobial agent as well as at least one negative control that are cultured in absence of added test aliquot. For example, 2, 3, 4, 5, 6, 7, or 8 or more concentrations of an antimicrobial agent are used. The concentrations used in a dilution series may differ two-fold between respective concentrations.

The term antimicrobial agent includes any agent that kills microorganisms or inhibits their growth. Antimicrobial agents of the present invention may particularly include antibiotics and antifungals. Antimicrobial agents may be microbicidal or microbiostatic. Various different classes of antibiotic are known, including antibiotics active against fungi, or particularly groups of fungi and any or all of these may be used. Antibiotics may include beta lactam antibiotics, cephalosporins, polymyxins, rifamycins, lipiarmycins, quinolones, sulphonamides, macrolides, lincosamides, tetracyclines, aminoglycosides, cyclic lipopeptides, glycylcyclines, oxazolidinones, lipiarmycins or carbapenems. Preferred antifungals of the present invention may include polyenes, imidazoles, triazoles and thiazoles, allylamines or echinocandins. Antimicrobial agents are continuously being developed and it is understood that also future antimicrobials will be possible to analyse with the current invention.

Preferably, at least one of the test microbial cultures comprises fastidious medium. More preferably, at least two of the test microbial cultures, e.g. at least two different growth conditions comprising the same antimicrobial agent at a different concentration, may comprise fastidious medium, such that the antimicrobial susceptibility of a microorganism to a particular antimicrobial agent under fastidious growth conditions.

Antimicrobial susceptibility may be determined by culturing the microorganisms from the sample, and analysing the AST cultures over a range of time points.

The AST cultures may be analysed at multiple time points to monitor microbial growth. For example, cultures may be analysed at time points 0, 1, 2, 3, 4, 5, 6, 7, 8, 9, 10, 11, 12, 13, 14, 15, 16, 17, 18, 19, 20, 21, 22, 23 or 24 hours after the initiation of culture. A culture may be analysed immediately after the initiation of culture, where t=0. Cultures may also be analysed at time periods beyond 24 hours after the initiation of culture. Typically cultures might be analysed at 0, 1, 2, 3, 4, 6 and 24 hours after the initiation of culture. However, results obtained and reported in the Examples below show that short incubation times can be sufficient for detecting differential microbial growth e.g. 4 hours. Accordingly, shorter total incubation time of up to 8, 7, 6, 5, 4, 3 or 2 hours may also be used, e.g. analysing every hour or every 2 hours or 90 minutes. As noted above, cultures are generally analysed at two or more time points, e.g. at two or more time points up to 4, 5 or 6 hours of culture. In certain embodiments, the AST cultures may be analysed at more frequent time points. A culture may be analysed at t=0, and may subsequently be analysed at intervals of 1, 2, 3, 4, 5, 10, 15, 20, 25 or 30 minutes. Accordingly, the total incubation time required when such short analysis intervals are used may also advantageously be reduced, and thus a shorter incubation time of up to 10, 15, 20, 25, 30 or 60 minutes may be used.

The monitoring or assessing of microbial growth in the AST assay may take place by monitoring growth continuously or at intervals over a time period (e.g. up to 10, 15, 20, 25 or 30 minutes or up to 1, 2, 3, 4, 5, 6, 7 or 8 hours), or by comparing the amount of microbial cell matter at the time the AST growth culture (test microbial culture) is initiated (t0) with the amount of microbial cell matter at a later time point (e.g. at up to 10, 15, 20, 25 or 30 minutes or up to 1, 2, 3, 4, 5, 6, 7 or 8 hours), i.e. the growth that has taken place in the intervening time. Alternatively, the amount of microbial cell matter may be determined at two or more different time points (e.g. measuring the first time point after 1, 2, 3, 4, 5, 10, 15, 20, 25 or 30 minutes or 1, 2, 3 or 4 hours, and measuring a second time point 1, 2, 3, 4, 5, 10, 15, 20, 25 or 30 minutes or 1, 2, 3, 4, 5, 6 or 7 hours after the first time point, or 2, 3, 4, 5, 6, 7, 8, 9, 10, 15, 20, 25, 30, 35, 40, 45, 50 or 55 minutes, or 2, 3, 4, 5, 6, 7 or 8 hours after the initiation of culture) and the amount of growth may thereby be determined. In preferred embodiments, the degree of microbial growth may be determined at more than one time point, i.e. at at least two time points.

In another embodiment, growth is assessed in a test microbial culture grown in the presence of an antimicrobial agent with a test microbial culture grown in absence of antibiotics (e.g. a positive control) at only one time point, e.g. at 1, 2, 3, 4, 5, 6, 7 or 8 hours. Monitoring growth at a time point (or two or more time points) after the initiation of the AST growth culture may advantageously allow a more accurate result to be achieved by avoiding measuring growth during the lag phase of microbial growth, as any differences between microbial growth under different conditions during this period of time will be small and difficult to detect. A first measurement may be taken according this method after 30 minutes or 1, 2, 3 or 4 hours, and a second measurement may be taken 1, 2, 3, 4, 5, 6, 7 or 8 hours after the first time point).

It will be apparent, however, that for certain microorganisms, e.g. certain anaerobes, mycobacteria or fungi, microbial growth may be less rapid, and thus an AST assay may need to be performed for a longer period of time. Thus, according to certain embodiments of the present invention, it may be necessary or desirable to perform the AST assay by measuring microbial growth for 8, 9, 10, 11 or 12 hours or more, e.g. 12, 18 or 24 hours. Suitable measurements at one or more time points may be taken accordingly.

In a preferred embodiment, growth may be measured in at least two growth conditions (e.g. each growth condition), relative to the initial number (amount or concentration) of microbial cells in each growth condition.

Culture of the test microbial cultures may take place at any temperature that promotes microbial growth, e.g. between about 20° C. and 40° C., or 20 to 37° C., preferably between about 25° C. and 37° C., more preferably between about 30° C. and 37° C. or 30 to 35° C. In one embodiment the AST cultures may be cultured at about 35° C.

Many methods for monitoring or assessing microbial growth are known and are used in AST assays, for example including turbimetric measurement, colorimetric determination, light detection, light scattering, pH measurement, spectroscopic measurements, fluorometric detection measuring of degradation products of antibiotics or microbial, measuring nucleic acid content or measuring production of gas, e.g. $CO_2$. Any of these may be used. However, according to a preferred embodiment of the present invention growth may be detected and assessed by determining or assessing the number and/or amount and/or size and/or area of microbial cells by imaging methods. As noted above, the microbial cells can include cells in colonies and/or aggregates. This may be achieved by assessing or determining the number or amount of microorganisms present before and/or after growth in presence of antimicrobial agents by any of the methods known to measure or detect microorganisms. Such a determination may involve determining the number and/or size of microbial cells, aggregates and/or colonies. Again, techniques for this are known and available. Thus, growth may be measured by monitoring the number and/or amount and/or size of microorganisms and/or microbial cells and/or colonies and/or aggregates over time. This may be measured directly or indirectly. The number or amount of microorganisms may be measured directly by haemocytometry, flow cytometry, or automated microscopy. Microorganisms may be fixed and/or permeabilised prior to detection. Alternatively, microorganisms may be detected under in vivo conditions.

Methods for AST assaying by bacterial cell count monitoring using flow cytometry are described in Broeren et al., 2013, Clin. Microbiol. Infect. 19. 286-291. Methods for performing AST assays in which bacteria are grown and enumerated by automated microscopy in multi-channel fluidic cassettes are described by Price et al. 2014, J. Microbiol. Met. 98, 50-58 and by Metzger et al., 2014. J. Microbiol. Met. 79, 160-165, and by Accelerate Diagnostics (see for example WO 2014/040088 A1, US 2014/0278136 A1 and U.S. Pat. No. 8,460,887 B2). In these methods, bacteria are immobilised and grown on a surface, and individual bacteria and/or colonies are assessed for viability and/or growth (including measuring colony growth) by imaging the surface at two or more time points. Such methods may be used according to the present invention. Other methods known are as described by Fredborg et al, J Clin Microbiol. 2013 July; 51(7):2047-53, and by Unisensor (U.S. Pat. No. 8,780, 181) where bacteria are imaged in solution using bright-field microscopy by taking a series of stacked images (object planes) of the solution, and counting the bacteria present in the sample.

Whilst any of the methods based on using imaging to monitor microbial growth may be used, the methods of the invention in the AST test step (step (iv) of the AST method) preferably do not rely on counting individual cells or on monitoring the growth of individual cells or colonies (e.g. on monitoring an increase in size of an individual cell or colony e.g. according to the methods of Accelerate Diagnostics Inc.) Thus, the present invention is not limited to (and in preferred embodiments does not involve) using a fixed position for imaging an AST culture or AST culture sample. Rather, it is preferred according to the present invention to monitor the bulk growth of cells in the AST culture, e.g. by imaging bulk cells in the field of view. The amount (e.g. area) of microbial cell matter (biomass) in the field of view may be determined by imaging. The cells/microbial biomass may be detected directly (e.g. by the microscope or camera etc.) e.g. using bright field microscopy or the microbial cells may be stained for detection, e.g. by adding stain to the AST culture or culture sample after the predetermined or required time period of growth.

Thus in the step (iv) of assessing the growth in the microbial test cultures, this is preferably done by imaging the test cultures over a large (significant or substantial) part of the culture available for imaging. Furthermore, in step (iv) the imaging may be done without pre-selecting a population or part of the test culture for imaging. Time-lapsed images of the liquid (broth) culture may be generated.

In a further particular embodiment, the AST cultures may be imaged or visualised directly without immobilising the microbial cells or without driving or actively transporting them to a surface, e.g. without applying a force, such as electrophoresis, to localise the cells to a detection location or surface for imaging.

In such imaging methods, algorithms may be applied to determine a value for the amount of microbial growth from the images according to methods and principles well known in the art. Thus, statistical methods may be applied to the images of microbial cells, based on the number, size, and/or area of microbial cell matter/biomass in the images (e.g. the amount of all the microbial cell matter in the image/field of view, for example total cell matter imaged). Algorithms may be written to take account of different growth patterns and/or morphologies, based on the identity of the microorganism and the antimicrobial agent present in the culture. An exemplary image analysis algorithm for use in measuring the amount of microbial biomass in a sample, and hence microbial growth, which combines thresholding and texture filtering, is described in our co-pending application WO 2017/216312, and such methods may be used to assess microbial growth in the AST methods of the present invention. Such counting or imaging methods allow a digital phenotypic analysis of the microorganism in the AST assay. Data has been obtained which shows that such digital phenotypic determinations deliver a MIC value similar to that of reference techniques (e.g. microbroth dilution).

A particular advantage of using such methods is that antimicrobial susceptibility testing may be performed on test microbial cultures comprising a wide range of concentrations or amounts of microorganisms, and it is not necessary to use a standardised microbial titer prior to perform the antimicrobial susceptibility testing. A useful feature of the present invention is the ability to use different concentrations of microorganisms. A test microbial culture or sample comprising at least $10^3$ CFU/ml may be used in the methods of the invention, for example samples (AST test samples) comprising at least $10^3$, $10^4$, $10^5$, $10^6$, $10^7$, $10^8$, $10^9$, $10^{10}$ or $10^{11}$ CFU/ml may be used. Alternatively a test microbial culture or sample comprising less than $10^3$ CFU/ml may be used, for example at least $10^2$ CFU/ml. A test microbial culture or sample comprising less than $10^2$ CFU/ml may also be used in the methods of the present invention.

Although bright field imaging represents one format for assaying the concentration of microbial cells in a test microbial culture, in one embodiment of the present invention, microorganisms may be detected by adding a marker that stains microorganisms (i.e. a stain or dye) prior to determining the number or amount of microorganisms the AST test cultures or by methods which utilize an intrinsic property of the microorganism such as e.g. phase contrast or any other method known in the art for quantifying the number of bacteria in the sample. Suitable stains might include coloured or fluorescent dyes, for example Gram staining or other staining for peptidoglycan or DNA staining, as a means of visualising the microorganism. In one particular embodiment of the present invention, DNA within a microorganism may be stained using Vybrant® Dye-Cycle™. Other DNA stains are well known and available. Indeed the number of stains available in the art for staining bacteria is vast and large numbers of such stains have been documented, including in standard reference texts, and are commercially available, e.g. from Life Technologies. Direct labelling of microorganisms by staining is easy to perform, convenient and cost-effective, and therefore represents a preferred embodiment.

Thus for example, the microorganisms may be grown for the AST assay in wells of a microtiter plate (i.e. each test microbial culture may be in a well of a plate), and the end of the growth periods the dye or stain may be added and the plate wells may be imaged and the number or amount of microorganisms or microbial cell matter may be assessed, by determining the number and/or size of microbial cells, aggregates or colonies e.g. by counting or imaging. Alternatively, microorganisms may be enumerated using a flow cytometer or similar type of instrument, for example the Aquila 400 instrument from Q-linea AB (Sweden), e.g. as described in U.S. patent application No. 61/979,319.

Algorithms for image analysis are well known and available in the art, to be able to analyse the image and derive or obtain a value for the amount of microbial biomass etc. As mentioned above, one such image analysis technique is described in WO 2017/216312 and this represents a preferred means of assessing and determining microbial growth in the AST test.

Further algorithms may be used to derive a MIC value for one or more antibiotics for the microorganism in the sample. In this regard, whilst an identification of the microorganism may assist in setting up the AST test, it is not a prerequisite of the method and microbial ID does not need to be known when the method is performed or set up. Thus, in terms of speed of test result, the AST method may be started when the identity (ID) of the microorganisms in the sample is unknown, but the ID may be used in the interpretation of the results, for example when the AST microbial test cultures are imaged, and/or when the results of the imaging are analysed. An MIC value may be obtained without microbial ID, but ID information is important in determining or interpreting SIR (susceptible/intermediate/resistant) information on the microorganism. Data processing techniques to derive or obtain MIC and/or SIR information from the growth data obtained from the imaging analysis are well known and available to the person skilled in the art.

In an alternative embodiment a microorganism may be specifically labelled via a biological feature within or on the microorganism. A "biological feature" may for example be a molecule in or on the microorganism e.g. a protein or other biomolecule expressed or located on the cell surface. For example a label, e.g. a coloured or fluorescent label, may be coupled to a protein or other affinity binding molecule that binds specifically to a particular biological feature. In one embodiment the protein may be a lectin, affibody or antibody, or antibody fragment. The microorganisms labelled in this way may be detected e.g. enumerated as previously described.

In a further embodiment proximity probes may be used to detect a specific biological feature within or on a microorganism.

In a further alternative embodiment of the present invention the microorganisms in the test microbial cultures may be detected and enumerated using a padlock probe and RCA-based amplified single molecule detection (ASMD) method. Such methods enable single microbial cells to be detected and counted. Thus, the microorganism may be detected by binding of the padlock probe and the number of microorganisms may be measured indirectly by an amplified signal generated via RCA of the circularised padlock probe. Each RCA product (blob) may be indicative of a single microorganism. Microorganisms may be lysed and padlock probes may be used which are designed to hybridise to one or more nucleotide sequences of the microorganisms. This may include a step of separating DNA, and preferably of selectively separating, or enriching for, microbial DNA. Since in the AST assay the test microbial cultures are usually less complex than in initial sample, a simplified protocol for separating or enriching microbial DNA may be used, involving for example filtration to separate microorganisms and microbial cell lysis or simply direct microbial cell lysis.

Alternatively, affinity binding molecules may be used which bind to one or more molecules present on a microorganism or within a lysed microorganism, such an affinity probe being provided with an nucleic acid label or tag to which a padlock probe may hybridise i.e. akin to an immunoRCA detection procedure. Similarly proximity probes may be used to bind to a target in or on a microorganism and the nucleic acid domains of the proximity probes may be used to template the ligation of a padlock probe and optionally also prime its amplification by RCA. Procedures for this are widely known and described in the literature. Circle-to-circle amplification (C2CA) as described for example in in Dahl et al, 2004, PNAS USA, 101, 4548-4553 and WO 03/012199 Dahl et al, 2004, PNAS USA, 101, 4548-4553 and WO 03/012199 may be used for signal amplification. The number of microorganisms in a sample can therefore be estimated by counting the number of blobs, which may be labelled e.g. fluorescently-labelled as described above 'blobs' within a sample. This thus provides another convenient means of obtaining a digital phenotypic susceptibility readout.

It is generally speaking advantageous in performing an AST assay for the microbial culture under test to be pure, i.e. for there to be a single microorganism. However, this is not an essential feature, and it is possible to use microbial detection methods based on visualisation or imaging to perform AST assays, for example methods as provided by Accelerate Diagnostics which use imaging of bacteria on a surface and not in solution, or indeed methods in which labelled microorganisms are detected in fluidic systems e.g. the automated microscopy fluidic cassette-based systems of Price et al. 2014, J. Microbiol. Met. 98, 50-58 and by Metzger et al., 2014. J. Microbiol. Met. 79, 160-165, discussed above. Any cell-by-cell detection, or shape recognition and/or identification methods may be used for AST assaying of samples which contain more than one microorganism. It is further known that different microorganisms may be affected differently by the same antibiotic and therefore the appearance of an organism upon treatment with a specific antibiotic may be used for identification and AST determination for each microorganism in co-cultures.

Conveniently the methods of the invention may be automated. Any one of more of the steps may be automated, preferably any or all of steps (a) to (e). Various specific or preferred steps discussed above lend themselves well to automation, for example contacting an aliquot with dyes and/or diluting an aliquot of the sample, and/or imaging an aliquot/stain mixture in the concentration determination methods of the present invention, as well as AST assaying and recovery of microorganisms from a sample. Automatic culturing methods have already been developed, including for blood culture methods, and these can be combined, for example, with automated concentration determination and/or AST assaying for use according to the present invention. Automation would provide the advantage of speed and ease of operation, as well as multiplexing ability, which are of importance in clinical laboratory setting and especially important in the diagnosis of sepsis.

The present invention also extends to apparatuses for carrying out the methods described herein. Thus, according to a further aspect, the present invention provides an apparatus for determining the concentration of intact microorganisms in a sample, said apparatus comprising:

a. a container for receiving a sample containing microorganisms;
b. a sample aliquoting device for withdrawing a sample aliquot from the sample;
c. a stain reservoir containing a first stain and a second stain, or a first stain reservoir containing a first stain and a second stain reservoir containing a second stain, wherein said first stain is a fluorescent stain, is cell-permeable, and has a first emission wavelength, and said second stain is cell-impermeable, and is capable of acting as an acceptor molecule in a FRET pair with the first stain acting as a donor molecule;
d. an first imaging device operable to image a mixture of the sample aliquot and first and second stains at the first emission wavelength; and
e. a processor operable to determine an image analysis value for the number of objects corresponding to intact microorganisms in the imaged mixture, and to compare the image analysis value to a pre-determined calibration curve, thereby to determine the concentration of intact microorganisms in said sample.

The apparatus described above may be configured to carry out the methods described herein as aspects of the invention, optionally including some or all of the preferred features of those methods. The apparatus may have features as described in connection with the above-described methods, and these features may be for the purpose described above and provide similar advantages.

The apparatus may comprise a diluent reservoir containing a diluent, and a diluent aliquoting device for withdrawing a diluent aliquot from the diluent reservoir. The apparatus may be configured to contact the sample aliquot with the diluent aliquot to provide a diluted aliquot at a dilution value, and preferably the device comprises a container for receiving the diluted aliquot, and contacting the sample aliquot with the diluent aliquot may optionally be performed in such a container.

The apparatus may be configured to provide two or more diluted aliquots from the sample at different dilution values. In certain embodiments, the device may, therefore, comprise two more containers for receiving each of two or more diluted aliquots. The apparatus may further be configured to provide a diluted aliquot from the sample at a first dilution value in a first container, and to contact an aliquot of said diluted aliquot with a further diluent aliquot in a second container, thereby to prepare a second diluted aliquot at a second dilution value.

Optionally, the apparatus may be configured to introduce first and second stains into a container for receiving a diluted aliquot prior to, simultaneously with, or following preparing a diluted aliquot.

The processor is preferably configured to determine whether the image analysis value falls within the range of a pre-determined calibration curve.

Preferably, the second stain has a second emission wavelength and the first imaging device is operable to image the mixture of the aliquot and first and second stains at the second emission wavelength, optionally simultaneously with imaging at the first emission wavelength.

The sample may comprise microorganisms contained in a growth medium.

In a preferred embodiment, the second stain has a higher DNA binding affinity than the first stain, such that the second stain is able to displace the first stain from DNA. The second stain may be a fluorescent stain, optionally a red-fluorescent stain, and preferably is propidium iodide.

The fluorescence intensity of the first fluorescent stain at said first emission wavelength is preferably enhanced when the stain is bound to nucleic acid.

The first fluorescent stain may have excitation and emission wavelengths in the wavelength range 350-700 nm. The first fluorescent stain may be a green-fluorescent stain. The first fluorescent stain may be an unsymmetrical cyanine dye.

The first imaging device may be a microscope. The microscope may be configured to make use of one or more microscopy techniques including: brightfield, oblique field, darkfield, dispersion staining, phase contrast, differential interference contrast, fluorescence, confocal, single-plane illumination, light sheet and wide field multiphoton microscopy.

Preferably, the apparatus comprises a well for imaging, wherein the well is for containing at least a portion of a mixture of a sample aliquot and first and second stains, or of a diluted aliquot and first and second stains. The imaging device is preferably configured to obtain images at one or more focal planes through the depth of the well. The imaging device may be configured to obtain a series of 2-D images along an optical axis of the imaging device, wherein each image is obtained at a different position along the optical axis.

Preferably, the processor is operable to analyse the images to detect objects corresponding to intact microorganisms, or clusters thereof. The processor may be configured to determine an area of each object by counting the number of contiguous pixels contained in each object, and optionally is configured to discount objects with an area below a predetermined area threshold. The processer may be configured to determine the morphology of each object, e.g. the circularity of each object and/or the evenness of fluorescence intensity in an object. The processor may further be configured to determine the maximum fluorescence intensity and/or mean, modal or median fluorescence intensity in each object, and optionally is configured to discount objects with a maximum fluorescence intensity below a predetermined maximum fluorescence intensity threshold or objects with a modal or median fluorescence intensity below a predetermined threshold. The processor may be configured to determine an object analysis value for each object, the object analysis value corresponding to the product of the object area and either the maximum fluorescence intensity or modal fluorescence intensity of the object, and is configured to calculate an image analysis value corresponding to the sum of the object analysis values for the objects.

In certain embodiments, the processor is operable to determine parameters for the population of imaged objects for any one or all of the factors outlined above. Thus, the processor may be configured to assign a value for a factor to each imaged object, and to determine a median or mean value for said factor for a population of objects, and/or the variance or standard deviation of one or more of said factors for the population of imaged objects.

In a preferred embodiment, the processor is operable to determine, preferably based on an analysis of the images, whether the microorganisms are clustering or non-clustering and based on this determination, is operable to use (i.e. select) a pre-determined calibration curve which is suitable for clustering or non-clustering microorganisms, as appropriate.

The apparatuses described above may be for use in antibiotic susceptibility testing (AST) to determine at least one minimum inhibitory concentration (MIC) value for at least one antimicrobial agent.

The apparatus may comprise a plurality of wells for test microbial cultures. In that case, the apparatus is preferably configured to inoculate a series of test microbial cultures in said wells using the sample, wherein the series of test microbial cultures may comprise at least two different growth conditions, wherein the different growth conditions may comprise one or more different antimicrobial agents, and two or more different concentrations of the antimicrobial agent(s), optionally wherein the plurality of wells comprises the said at least two different growth conditions.

The apparatus preferably comprises an imaging device for assessing the degree of microbial growth in each growth condition. In one embodiment, the imaging device is a line camera.

The processor is preferably configured to determine at least one MIC value from at least one antimicrobial agent, based on the degree of microbial growth in each growth condition.

The apparatus may be configured to adjust the concentration of at least a portion of the sample, to inoculate the series of test microbial cultures, based on the determined concentration of intact microorganisms in the sample. Preferably, the apparatus is configured to adjust the concentration of at least a portion of the sample by diluting at least a portion of the sample, or by culturing or further culturing the sample.

In some embodiments, at least one of the test microbial cultures comprises fastidious medium.

The apparatus may comprise one or more consumables. For example, the apparatus may comprise a first consumable in which the stain reservoir(s) is/are provided. The mixture of the sample aliquot and first and second stains may be imaged in the first consumable. Alternatively, the mixture of the sample aliquot and first and second stains may be imaged in a second consumable.

The above-described plurality of wells for the test microbial cultures may be provided in the first consumable, or in a or the second consumable, or in a third consumable.

The apparatus is preferably configured to recover microorganisms from a sample, thereby to provide a recovered microorganism sample. In that case, the apparatus may comprise a lysis buffer reservoir containing a buffer for the selective lysis of non-microbial cells in a sample and recovery means for recovering intact microorganisms from the sample. The lysis buffer reservoir and recovery means may be provided in the first consumable. The recovery means is preferably a filter.

The apparatus is preferably automated.

The invention also extends to use of the apparatus (i.e. the apparatus of the preceding aspect, optionally incorporating some or all of the optional features described above) to determine the concentration of intact microorganisms in a sample for use in antibiotic susceptibility testing (AST) to determine at least one minimum inhibitory concentration (MIC) value for at least one antimicrobial agent.

In a further aspect, the invention provides a concentration determination consumable comprising: a stain reservoir containing a first stain and a second stain, or a first stain reservoir containing a first stain and a second stain reservoir containing a second stain, wherein said first stain is a fluorescent stain, is cell-permeable, and has a first emission wavelength, and said second stain is cell-impermeable, and is capable of acting as an acceptor molecule in a FRET pair with the first stain acting as a donor molecule; and a well for imaging, wherein the well is for containing at least a portion of a mixture of a sample aliquot and first and second stains, or of a diluted aliquot and first and second stains.

The concentration determination consumable may comprise a lysis buffer reservoir containing a buffer for the selective lysis of non-microbial cells in a sample.

The concentration determination consumable may comprise a recovery means for recovering intact microorganisms from the sample, wherein the recovery means is preferably a filter.

The concentration determination consumable may alternatively or additionally comprise a diluent reservoir containing a diluent. The concentration determination consumable preferably further comprises one or more containers for receiving diluted aliquot(s) of the sample.

In a final aspect, the invention provides a concentration determination kit, comprising: a first consumable comprising a stain reservoir containing a first stain and a second stain, or a first stain reservoir containing a first stain and a second stain reservoir containing a second stain, wherein said first stain is a fluorescent stain, is cell-permeable, and has a first emission wavelength, and said second stain is cell-impermeable, and is capable of acting as an acceptor molecule in a FRET pair with the first stain acting as a donor molecule; and a second consumable comprising a well for imaging, wherein the well is for containing at least a portion of a mixture of a sample aliquot and first and second stains, or of a diluted aliquot and first and second stains.

The first consumable may further comprise a lysis buffer reservoir containing a buffer for the selective lysis of non-microbial cells in a sample; and/or a recovery means for recovering intact microorganisms from the sample, wherein the recovery means is preferably a filter; and/or a diluent reservoir containing a diluent, and preferably a container for receiving a diluted aliquot of the sample.

FIG. 1 shows the number of intact microorganisms measured in a *H. influenzae* (A) or *P. aeruginosa* (B) sample recovered from a blood culture, incubated with a stain solution at 4° C., room temperature, and 35° C.

FIG. 2 shows the combined data for the relationship between the concentration of intact microorganisms in a sample, and the object number determined by imaging, for a range of different microorganisms. The data show good linearity, with a spread of approximately an order or magnitude between the different microorganisms. Additionally, *S. aureus* (a clustering microorganism) deviates from the main data.

FIG. 3 shows the combined data from FIG. 2 (axes reversed) for all non-clustering microorganisms, with a regression line adapted to minimise the number of experimental points falling outside ±60% boundaries from the best-fit line, per EUCAST recommendations.

FIG. 4 shows the data from FIG. 3 for individual microorganisms. (A—*K. pneumonia*; B—*H. influenza*; C—*P. aeruginosa*; D—*P. mirabilis*; E—*E. faecalis*; F—*S. pneumonia*). The same calibration curve was found to be suitable for all non-clustering microorganisms tested.

Figure 6:
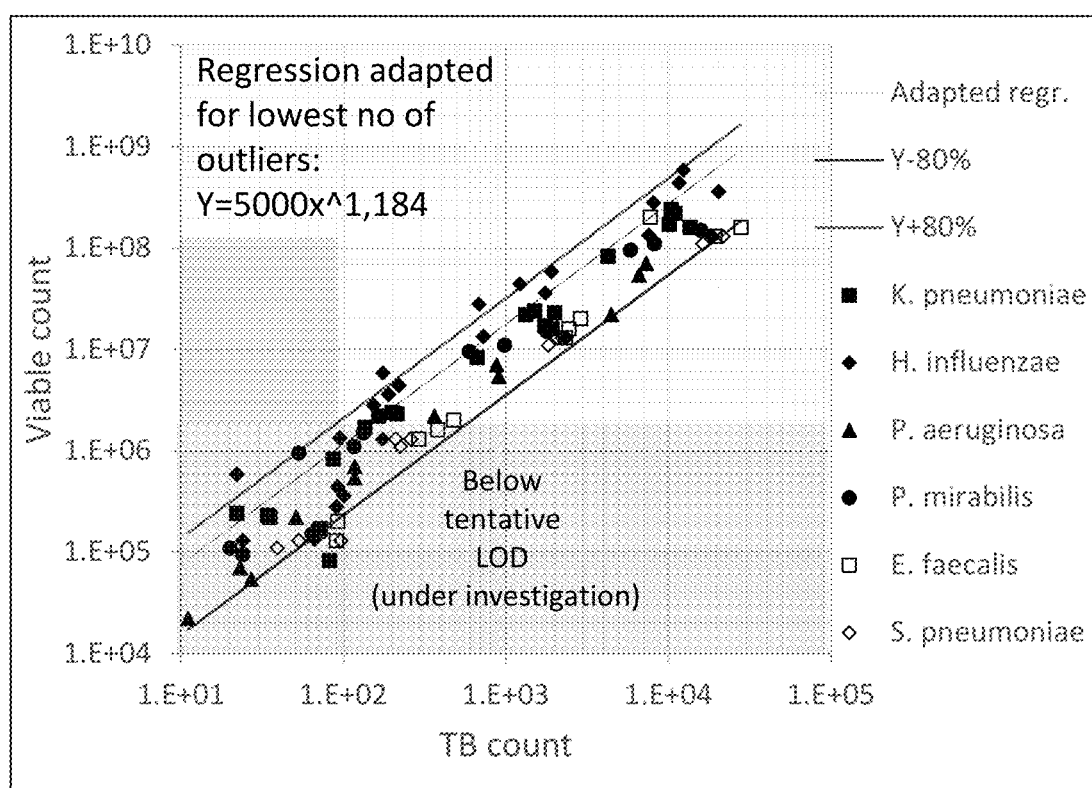
FIG. 6 shows the combined data from FIG. 2 (axes reversed) for all non-clustering microorganisms, with a regression line adapted to minimise the number of experimental points falling outside ±80% boundaries from the best fit line. With the exception of *H. influenzae*, all data points above the LOD fell within these boundaries.
Figure 7:
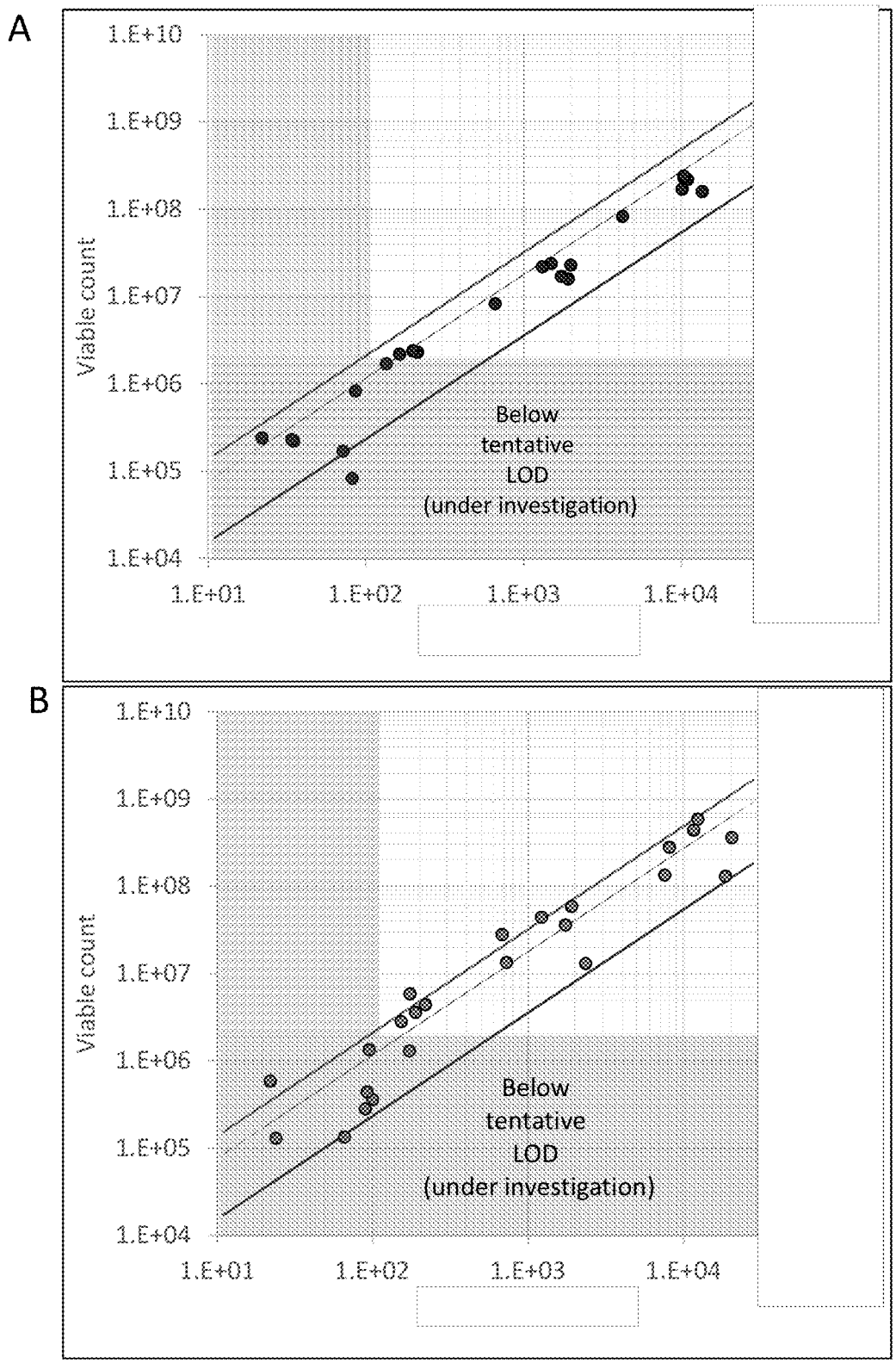
Figure 7:
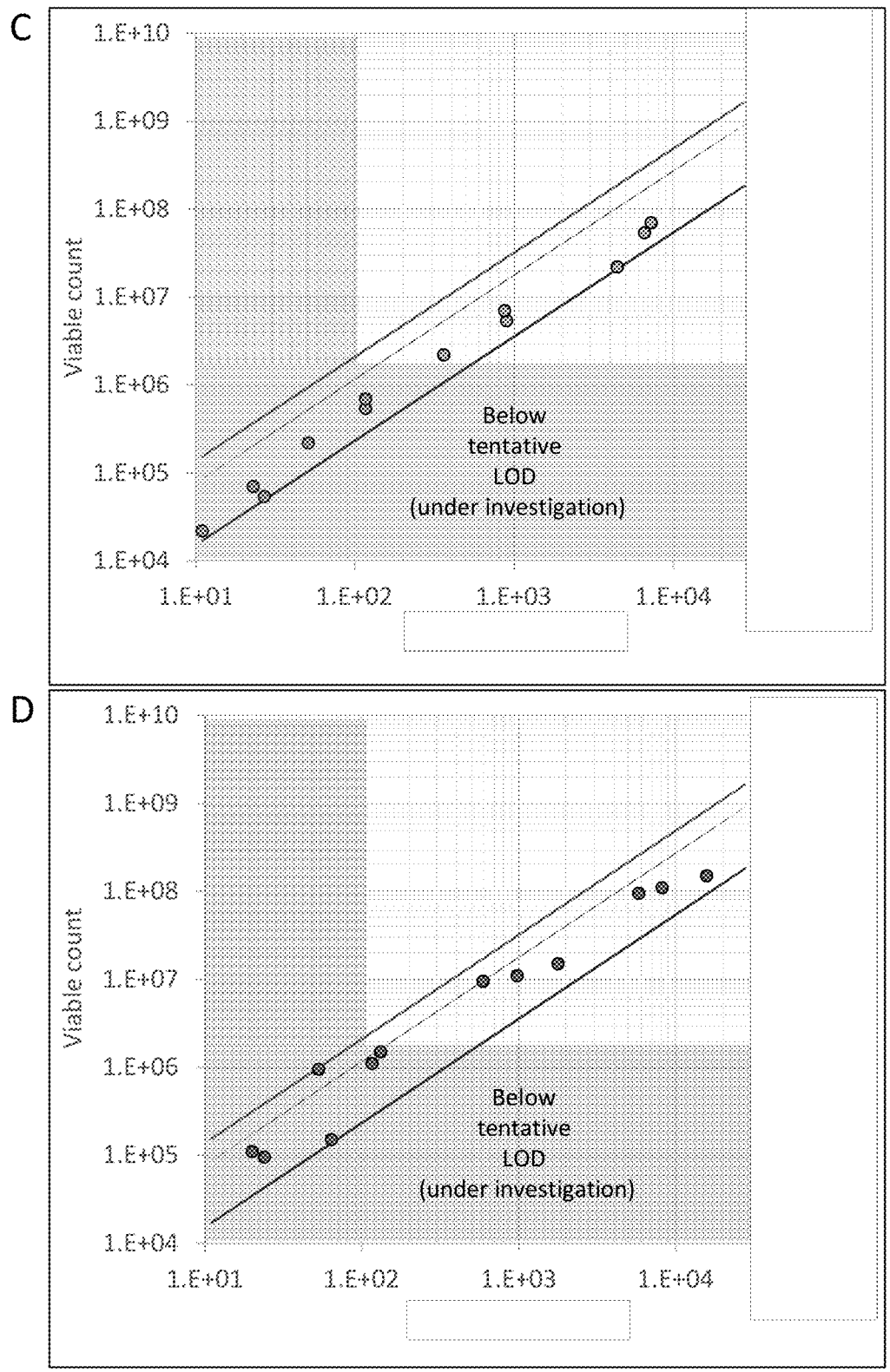
Figure 7:
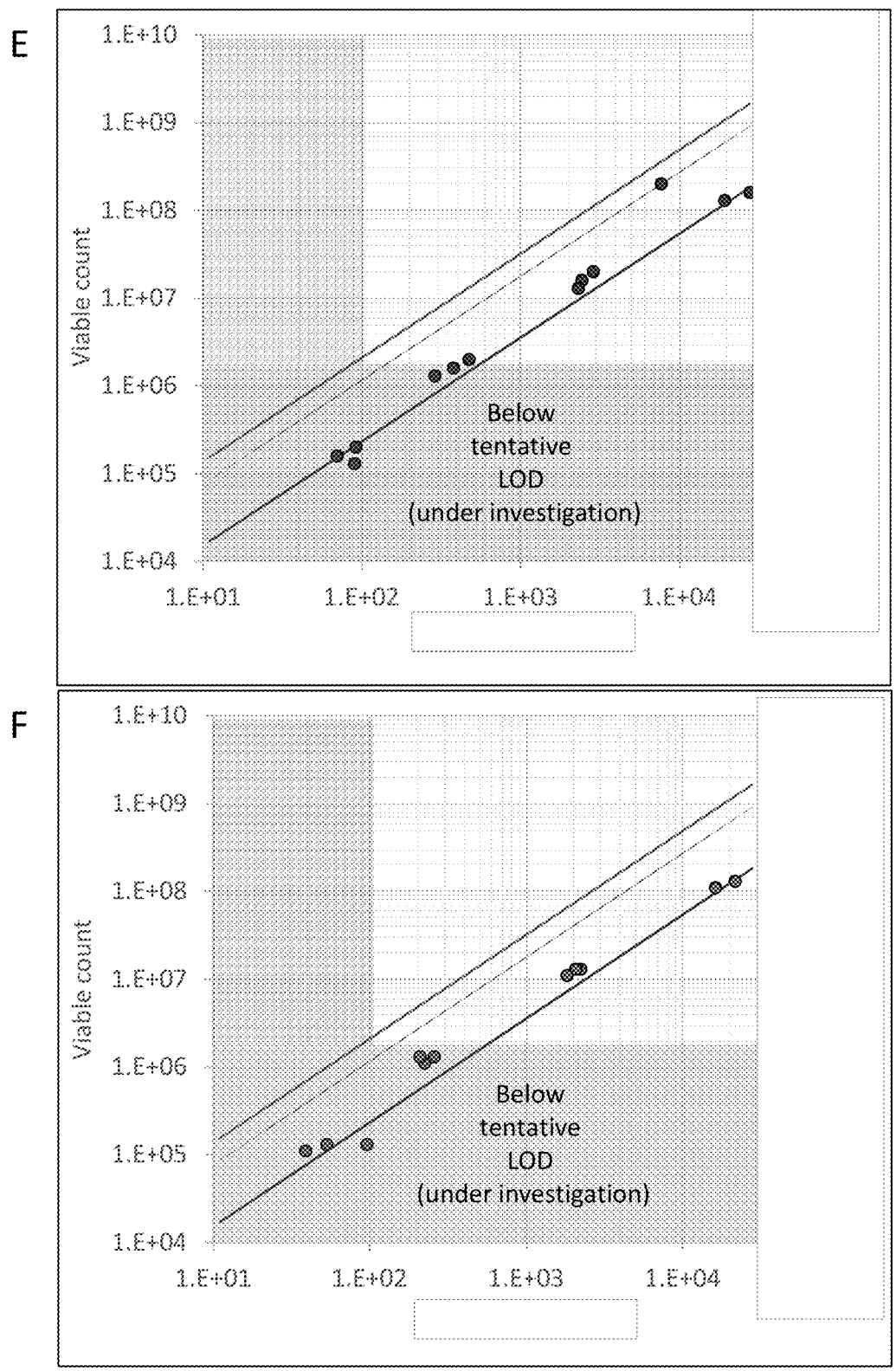

FIG. 7 shows the data from FIG. 6 for individual microorganisms A—*K. pneumonia*; B—*H. influenza*; C—*P. aeruginosa*; D—*P. mirabilis*; E—*E. faecalis*; F—*S. pneumonia*) using a ±80% boundary. The best fit curve was adjusted accordingly. The same calibration curve was found to be suitable for all non-clustering microorganisms tested.

Figure 8:
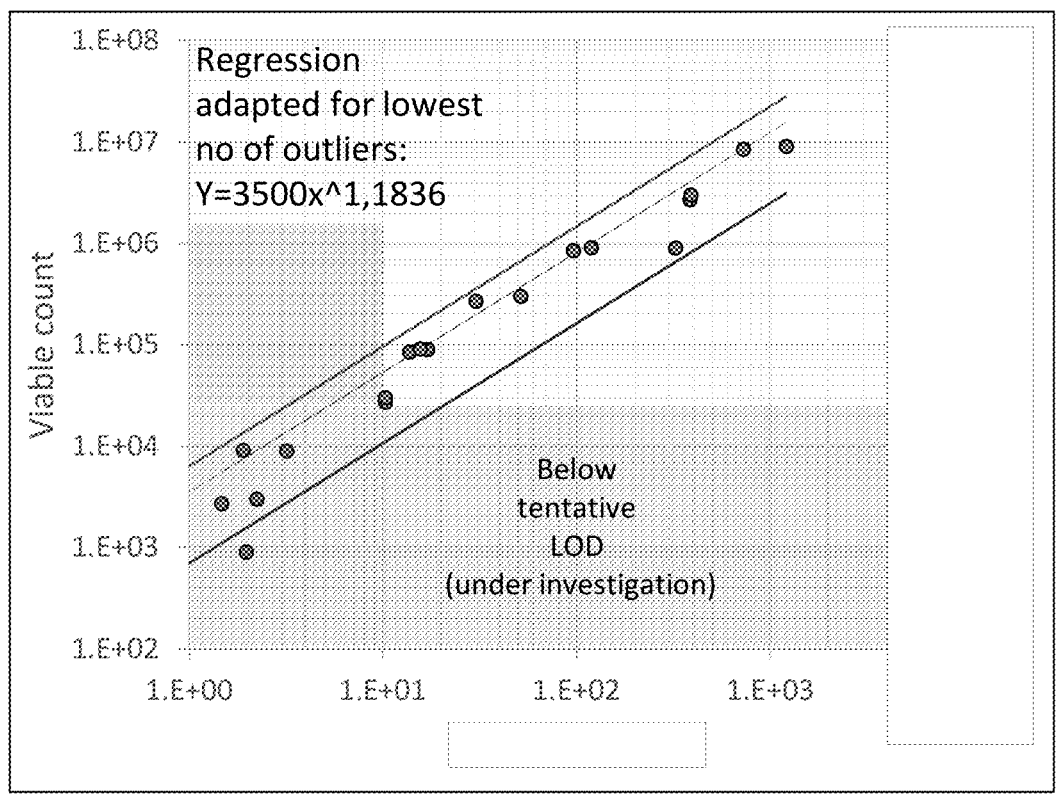

FIG. 8 shows the data and a calibration curve for *S. aureus* at the ±80% boundary.

Figure 9:
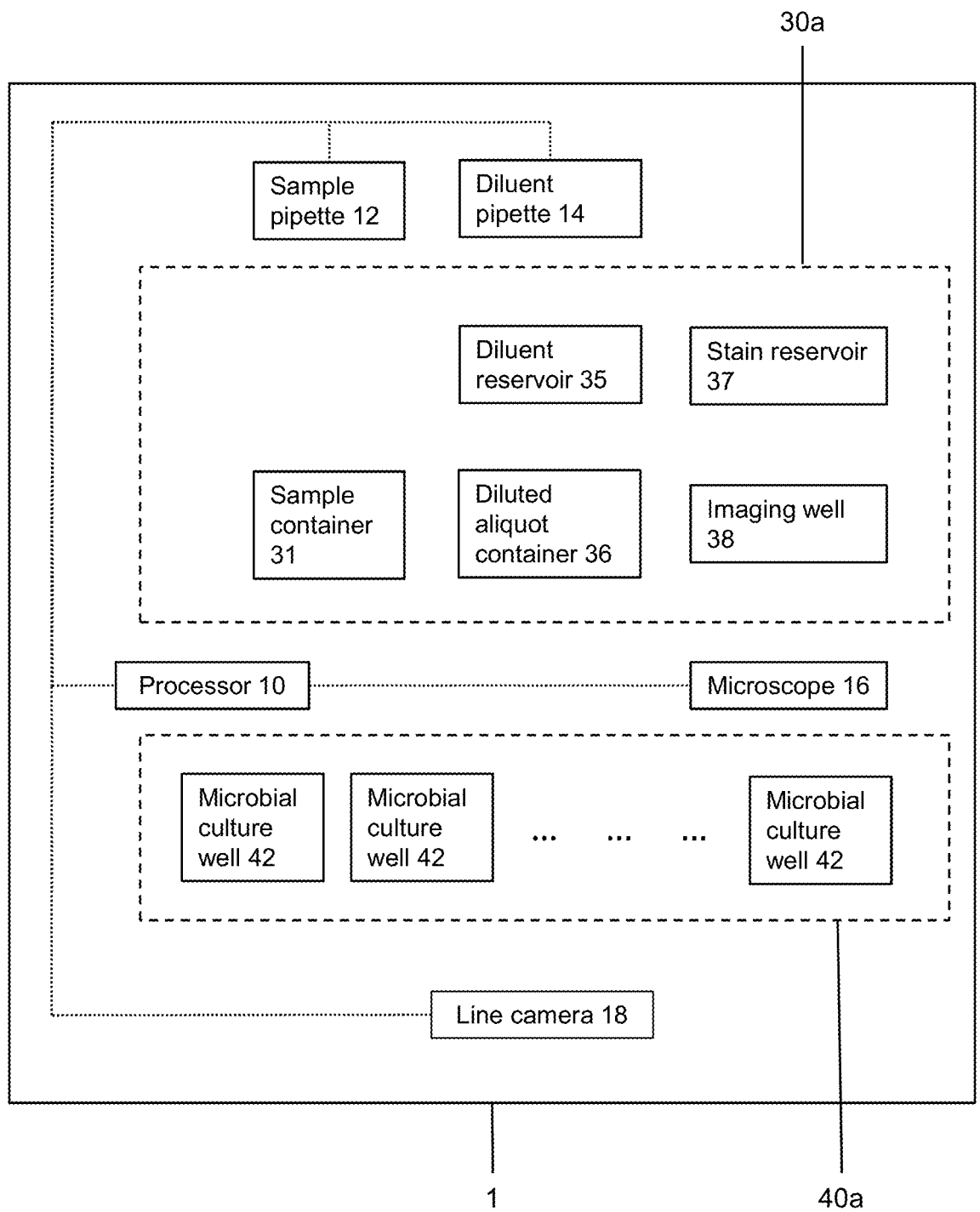

FIG. 9 shows a schematic and simplified diagram of a first AST apparatus that is suitable for receiving a cell culture according to an embodiment of the present invention.

Figure 10:
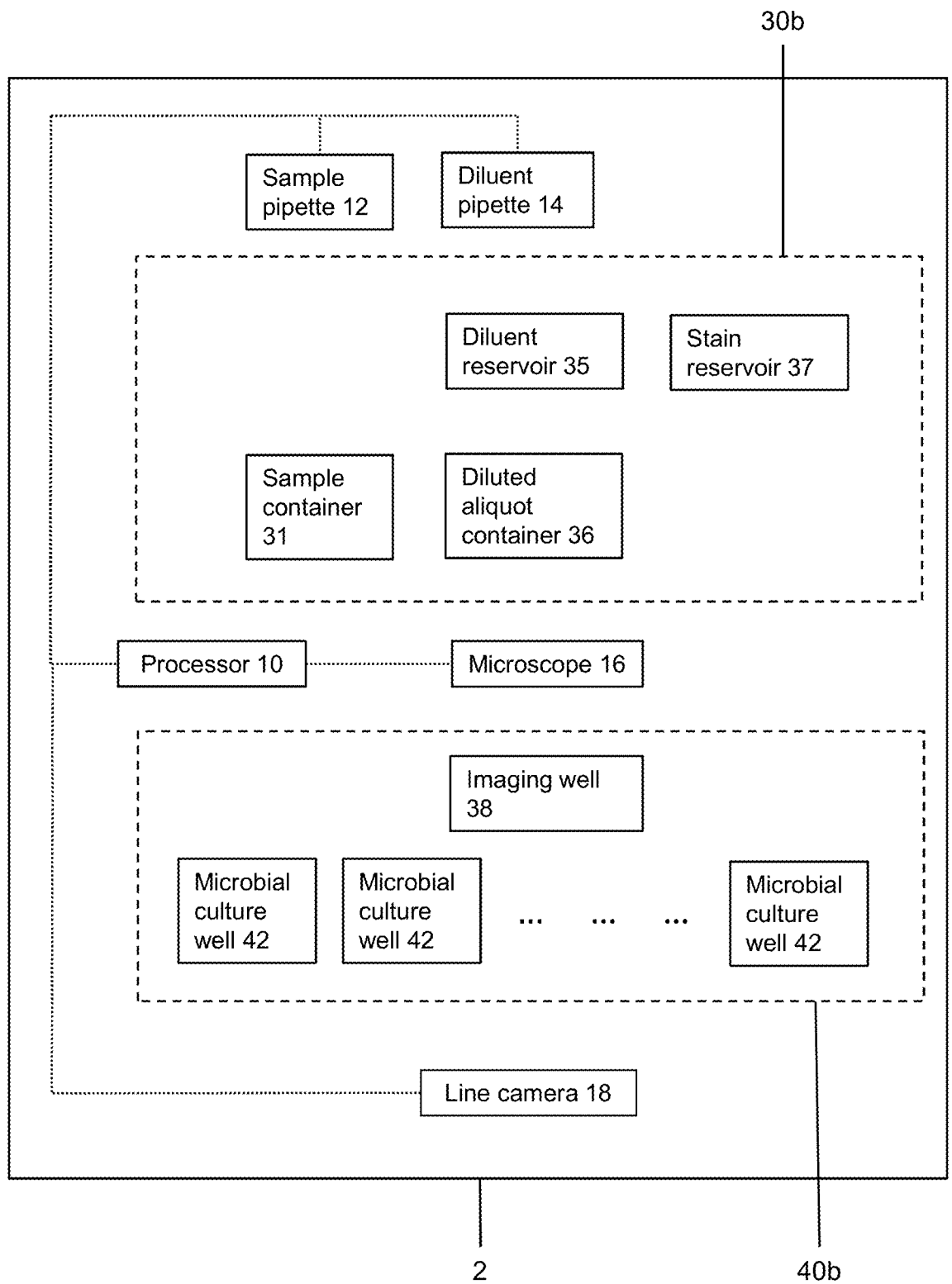

FIG. 10 shows a schematic and simplified diagram of a second AST apparatus that is suitable for receiving a cell culture according to an embodiment of the present invention.

Figure 11:
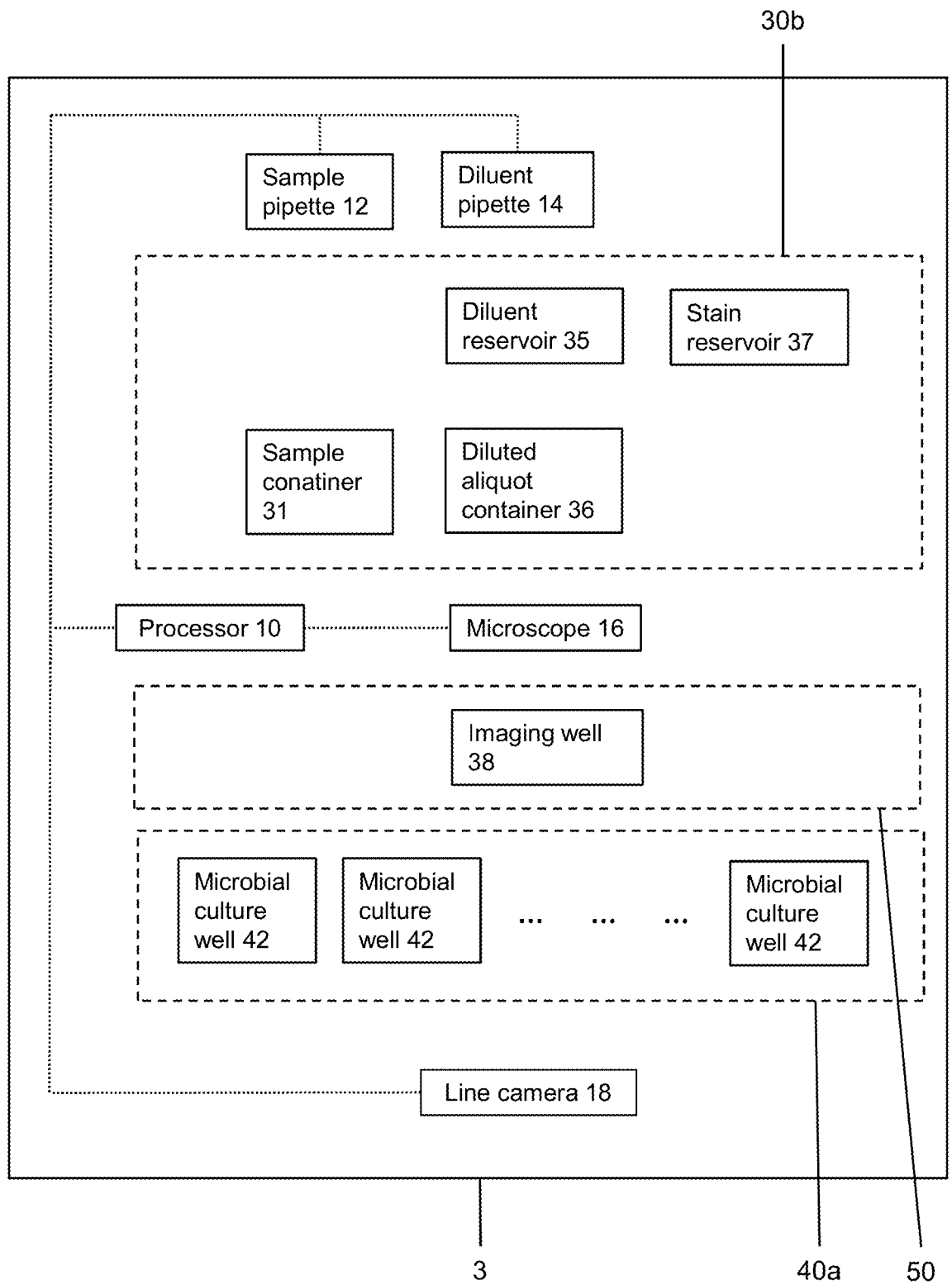

FIG. 11 shows a schematic and simplified diagram of a third AST apparatus that is suitable for receiving a cell culture according to an embodiment of the present invention.

Figure 12:
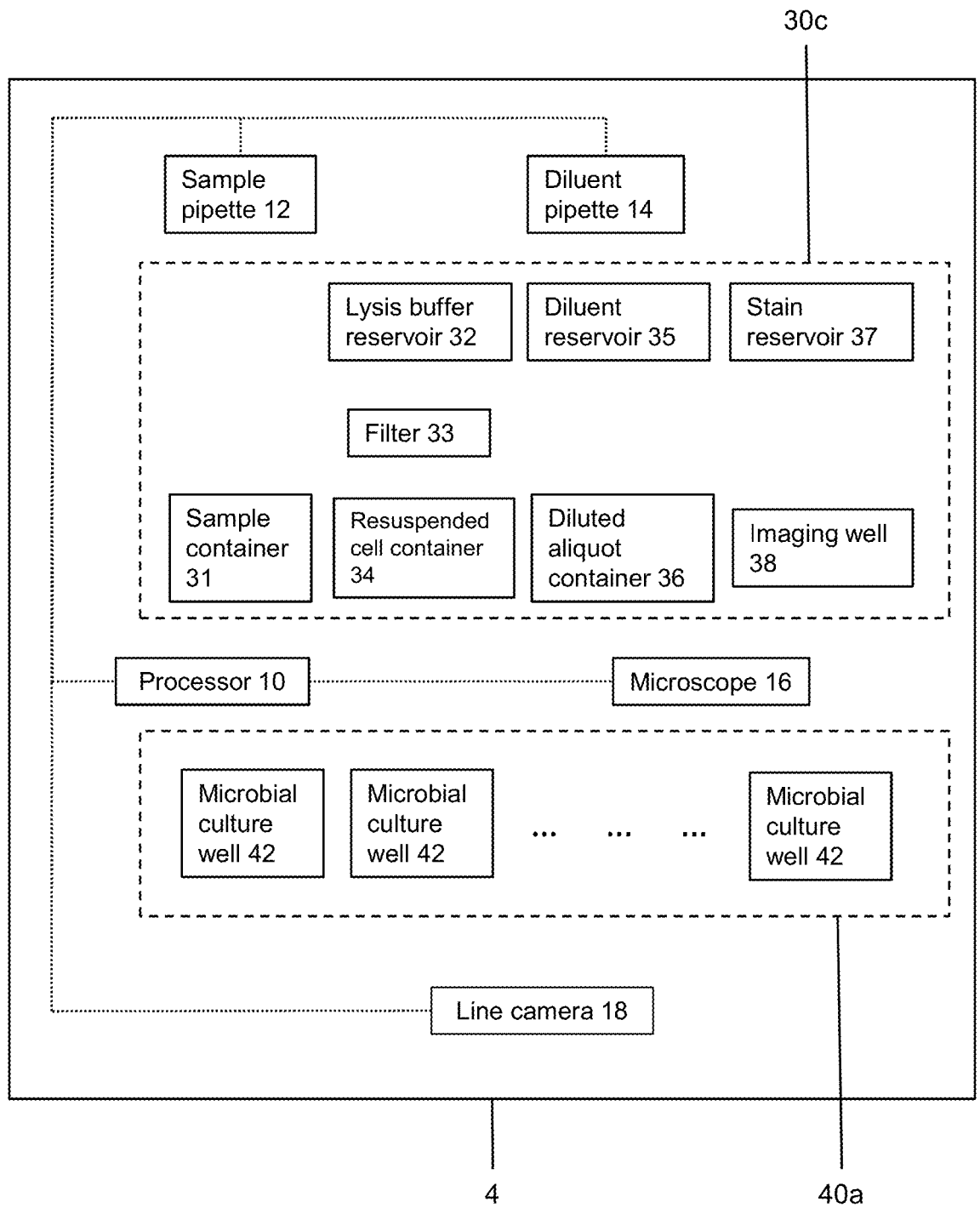

FIG. 12 shows a schematic and simplified diagram of a fourth AST apparatus that is suitable for receiving a patient sample according to an embodiment of the present invention.

Figure 13:
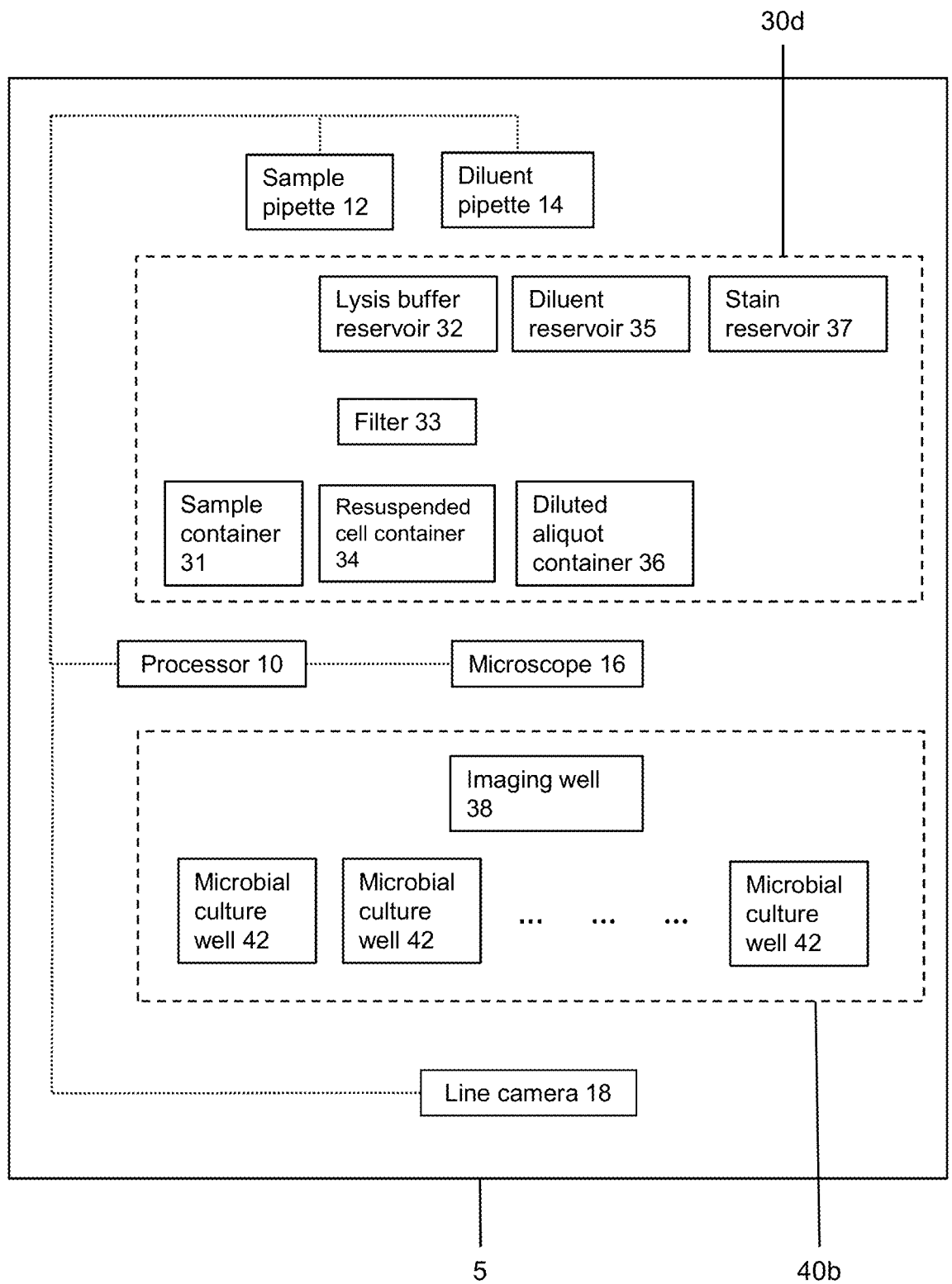

FIG. 13 shows a schematic and simplified diagram of a fifth AST apparatus that is suitable for receiving a patient sample according to an embodiment of the present invention.

Figure 14:
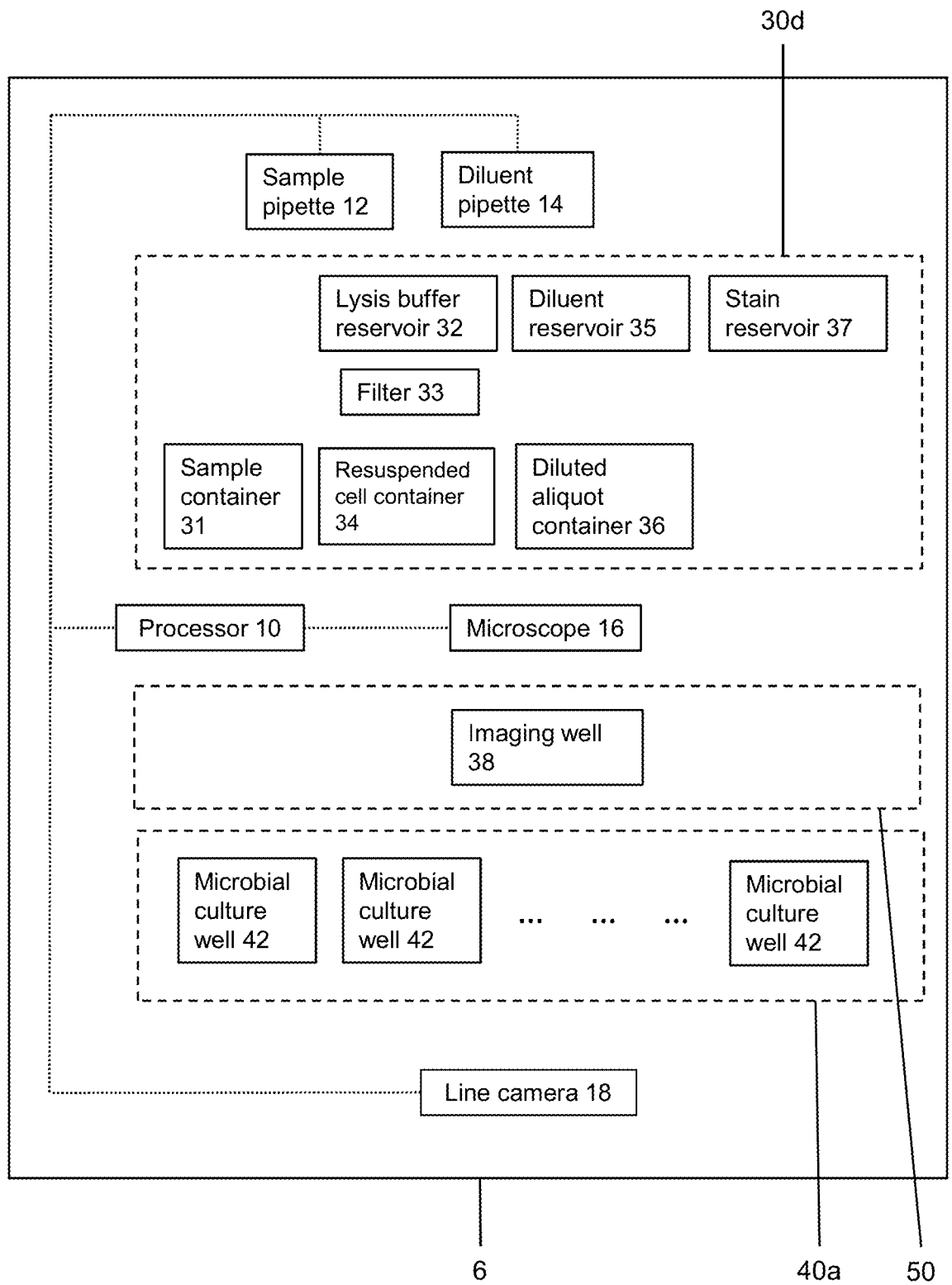

FIG. 14 shows a schematic and simplified diagram of a sixth AST apparatus that is suitable for receiving a patient sample according to an embodiment of the present invention.

Figure 15:
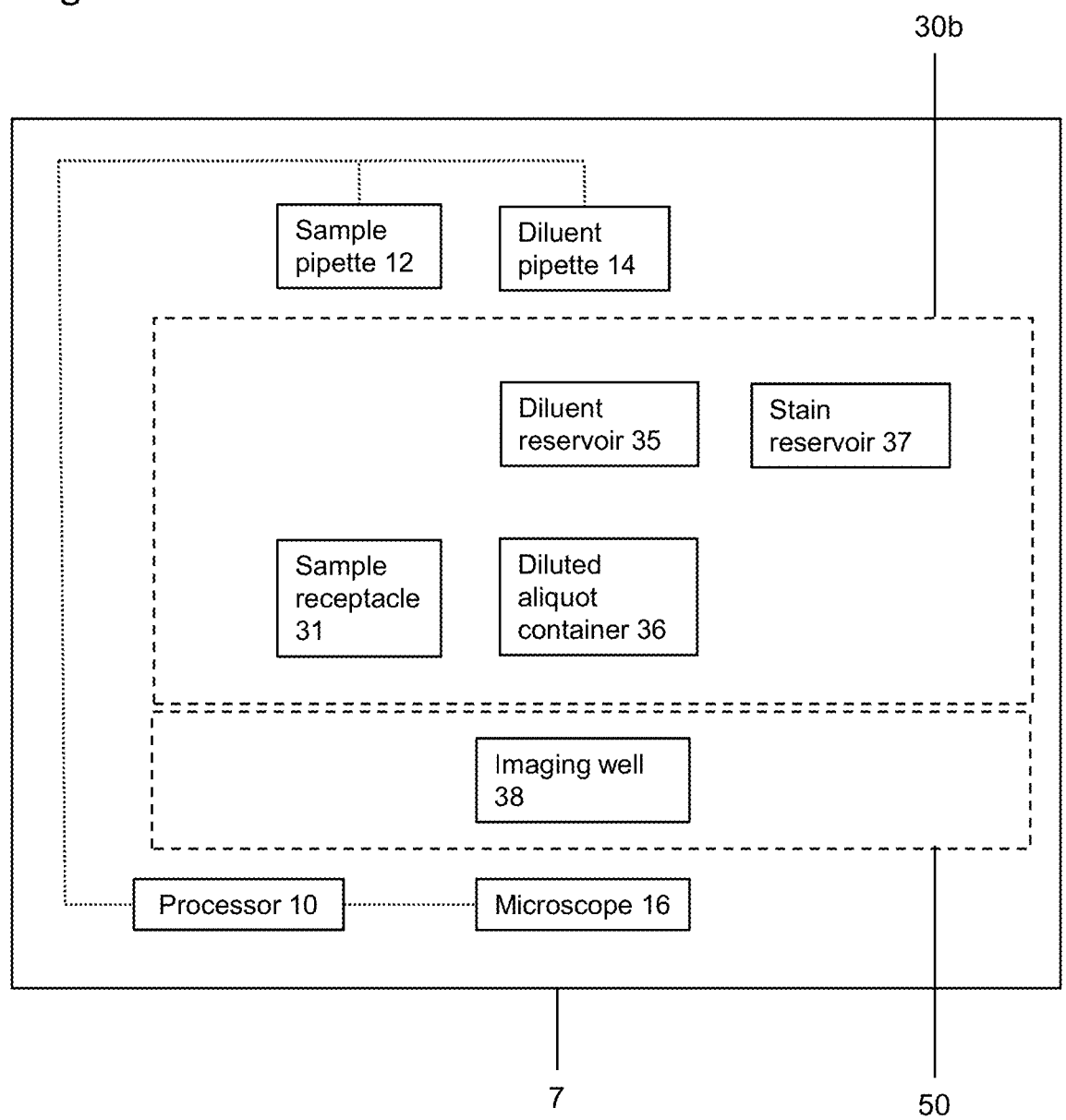

FIG. 15 shows a schematic and simplified diagram of a concentration determination apparatus that is suitable for receiving a cell culture according to an embodiment of the present invention.

Figure 16:
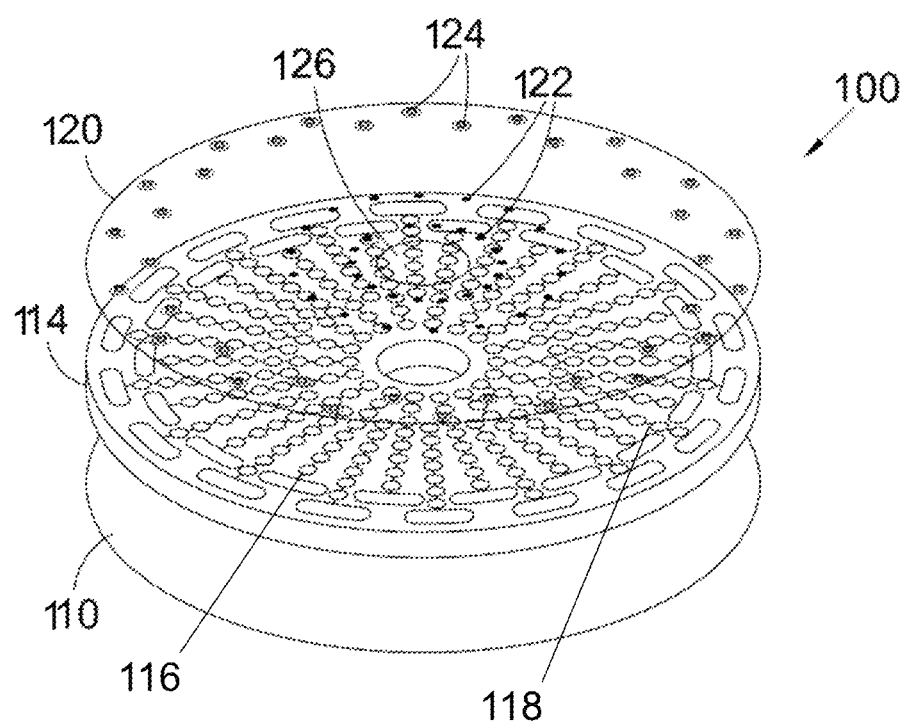

FIG. 16 shows a consumable suitable for use in the AST apparatus of FIGS. 9 to 14 or the concentration determination apparatus of FIG. 15.

EXAMPLE 1

Concentration Determination and Setting Up an AST Assay

A first aliquot of a sample (20 µl) is diluted in 80 µl PBS, and a 15 µl aliquot of the diluted mixture is added to 15 µl stain solution containing 10 µM SYTO BC and 3 µM propidium iodide to provide a first diluted aliquot/stain mixture. An aliquot of the sample/PBS mixture (20 µl) is diluted further in 180 µl PBS, and a 15 µl aliquot is diluted in 15 µl stain solution to provide a second diluted aliquot/stain mixture.

The first and second diluted aliquot/stain mixtures are transferred to separate imaging wells to a depth of approximately 2 mm. 50 images are obtained of microorganisms in suspension for each well, spaced 30 µm apart in the direction of the optical axis, using an emission filter at 502-561 nm to detect the SYTO BC emission peak at 509 nm. The images obtained are thresholded and subjected to analysis to determine the size, fluorescence intensity, and optionally morphology of each object corresponding to an intact microorganism to obtain an image analysis value for each diluted aliquot. Characteristics of the microorganisms in the sample are used to select a pre-determined calibration curve for use in the concentration determination step (e.g. to determine whether the sample is a clustering or a non-clustering microorganism). One of the diluted aliquots having an image analysis value within the range of a pre-determined calibration curve is identified. The concentration of intact microorganisms in the sample is determined by comparing the image analysis value for the selected diluted aliquot with the pre-determined calibration curve.

An inoculum for inoculating a series of test microbial cultures for an antimicrobial susceptibility test (AST) assay is prepared by adjusting the concentration of at least a portion of the sample by dilution using a suitable growth medium (e.g. cation adjusted Mueller Hinton broth (CAMHB), if necessary. Optionally, a further inoculum in fastidious medium is also prepared. The inoculum (or inocula) is prepared to a concentration of $5 \times 10^5$ CFU/ml and is added to a series of wells containing freeze-dried antimicrobial agents to prepare a series of test microbial cultures at at least two different growth conditions in an AST assay.

EXAMPLE 2

Effect of Stain Incubation Temperature on Concentration Determination 10 ml blood spiked with *H. influenza* or *P. aerurinosa* was added to a Bactec flask (BD) and incubated overnight until a positive culture result was obtained. Selective lysis of non-microbial cells present in the blood culture flask was performed using a lysis buffer and samples were filtered using a 0.2 µm nylon mesh filter. Following filtration, samples were washed with cation adjusted Mueller Hinton broth (CAMHB) and resuspended by back-flushing CAMHB through the filter membrane.

Diluted aliquots of the recovered microorganism samples were further diluted and contacted with stain solutions as outlined in Example 1. Diluted aliquot/stain mixtures were covered with foil, and incubated for 5 minutes at 4° C., room temperature, or 35° C. Each aliquot was imaged and the images analysed as outlined in Example 1 to determine an image analysis value for the number of objects corresponding to intact microorganisms. Repeats were performed for each diluted aliquot at each temperature. An image analysis value for a control sample was also determined. The image analysis values determined following preparation at each temperature was compared, and found to be similar for all temperatures for *H. influenzae*. Room temperature and 35° C. preparation were found to be similar for *P. aeruginosa*. Similar values were also determined for the control sample at all temperatures.

Aliquots of the recovered microbial sample were diluted by a factor of $1 \times 10^{-4}$, $1 \times 10^{-5}$ and $1 \times 10^{-6}$ in PBS and plated to confirm microbial viability.

EXAMPLE 3

Preparing Pre-Determined Calibration Curves

Figure 1:
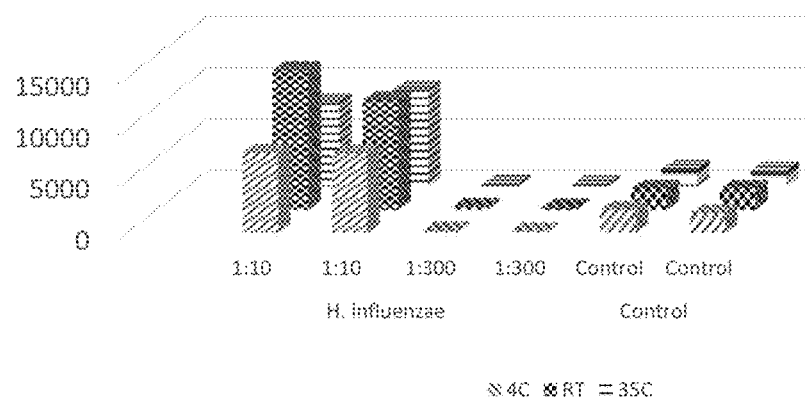
Figure 1:
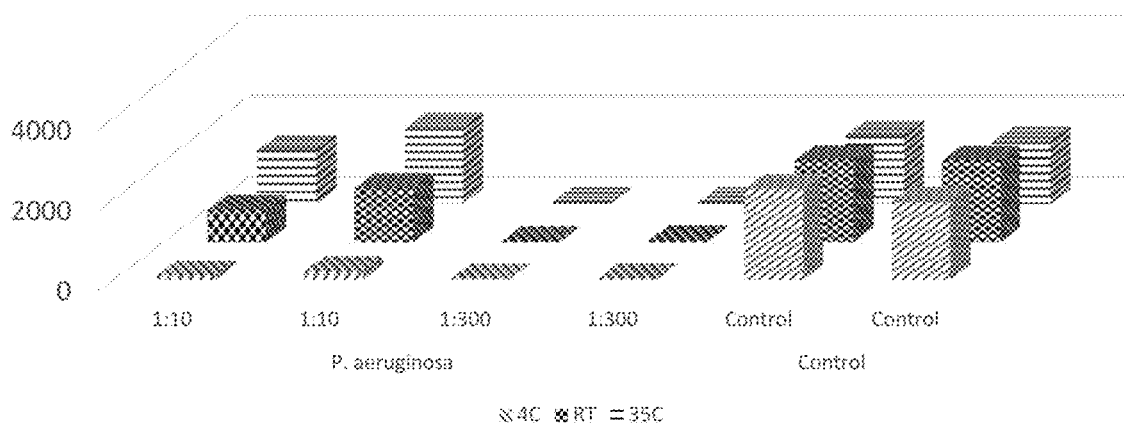
Figure 2:
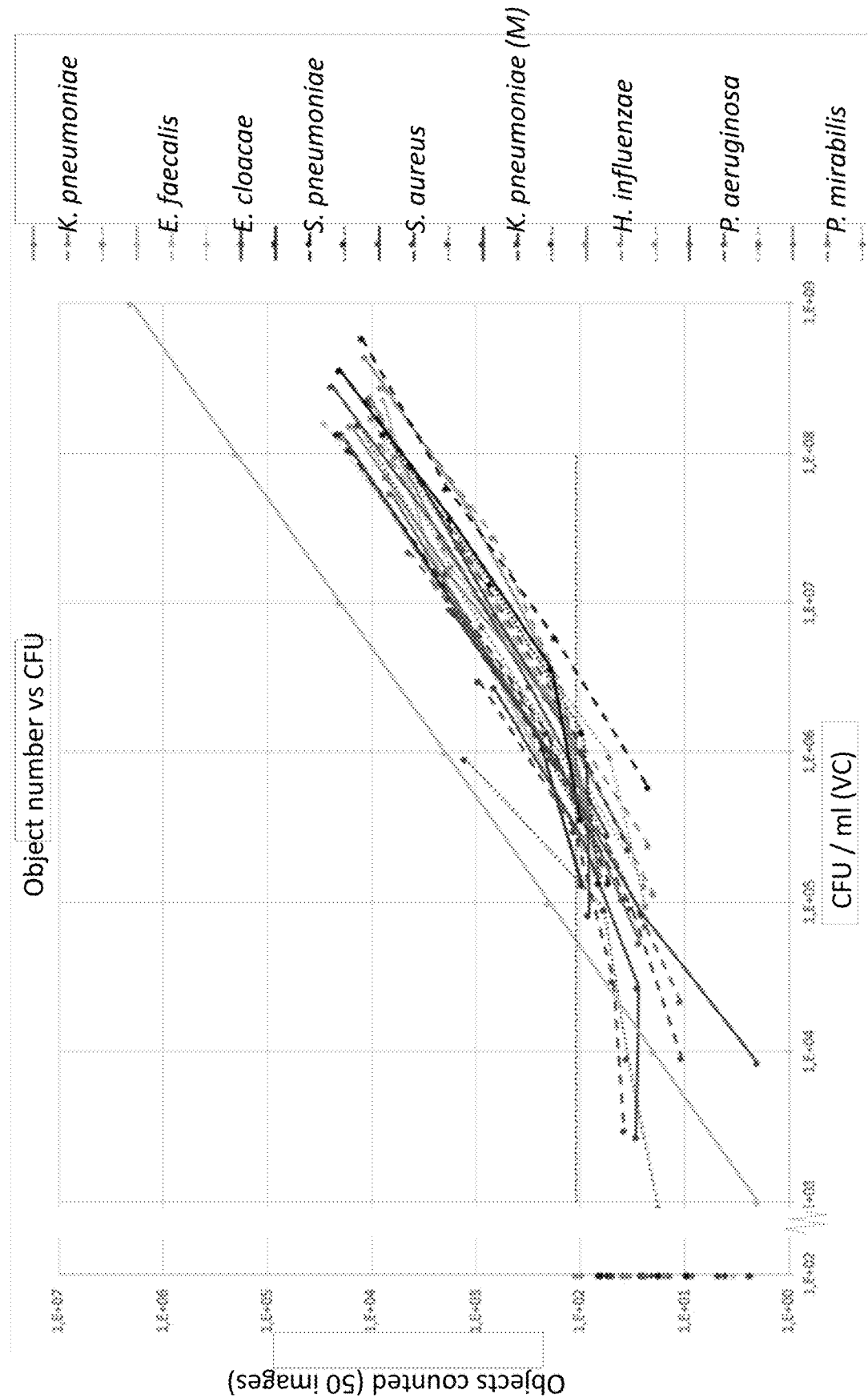

Data were collected for a number of different microorganisms at different concentrations, and the relationship between the number of objects counted and the concentration of intact microorganisms was plotted on a graph (FIG. 2). These data show that there is a linear relationship between the number of objects counted and the concentration of intact microorganisms for the majority of microbial species (albeit with a spread of approximately an order of magnitude for the number of objects counted for a given concentration between the different species measured).

Figure 3:
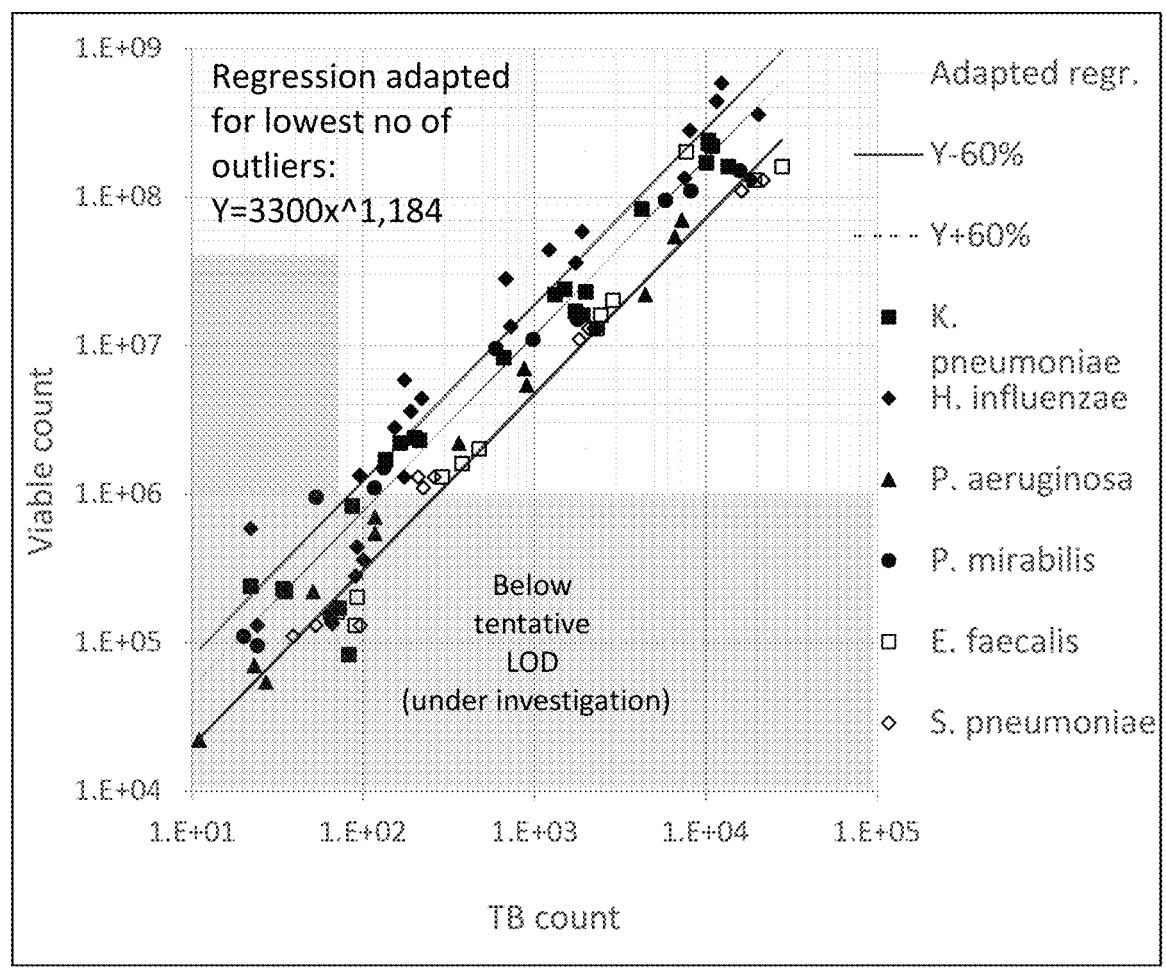
Figure 4:
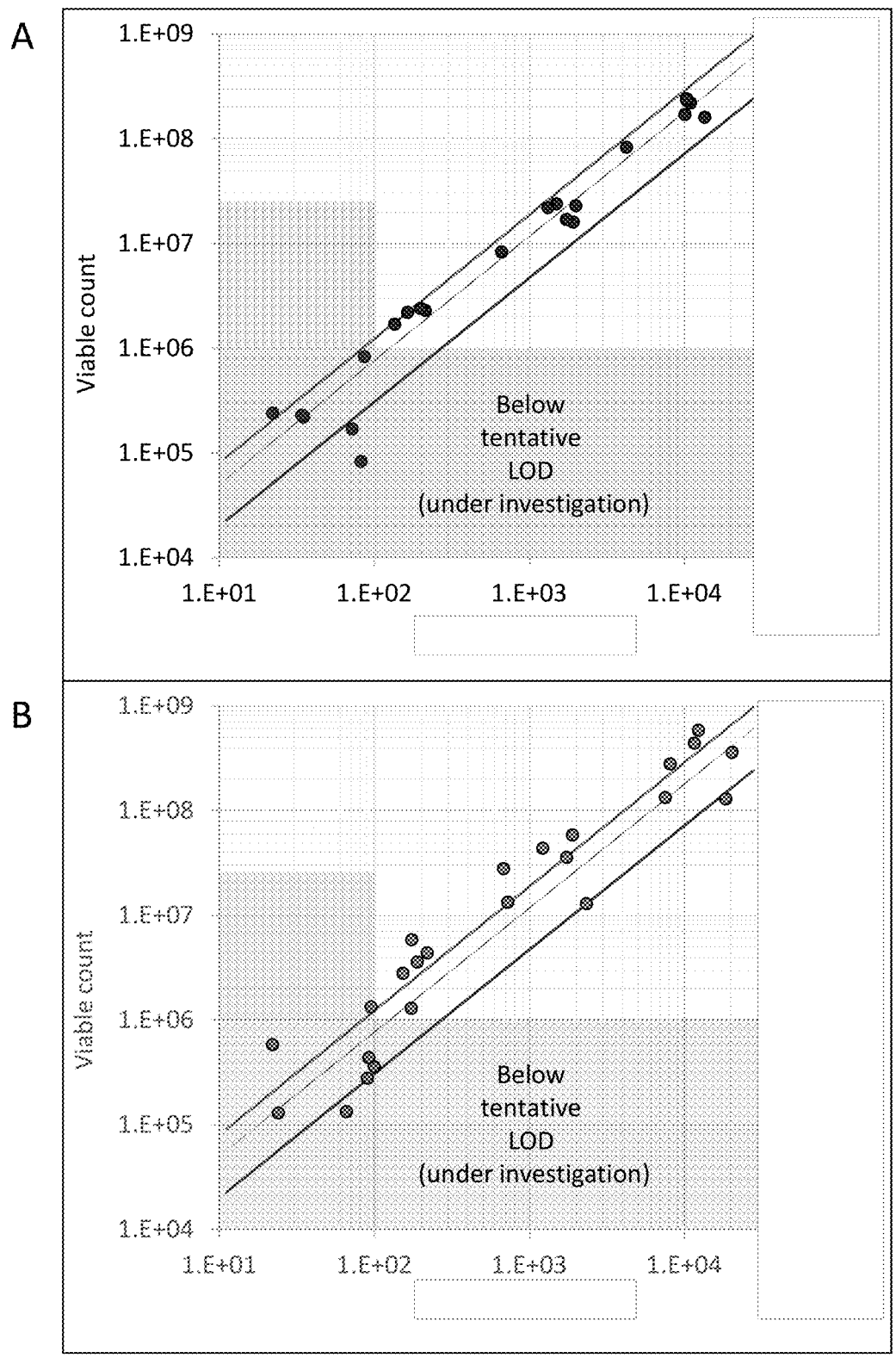
Figure 4:
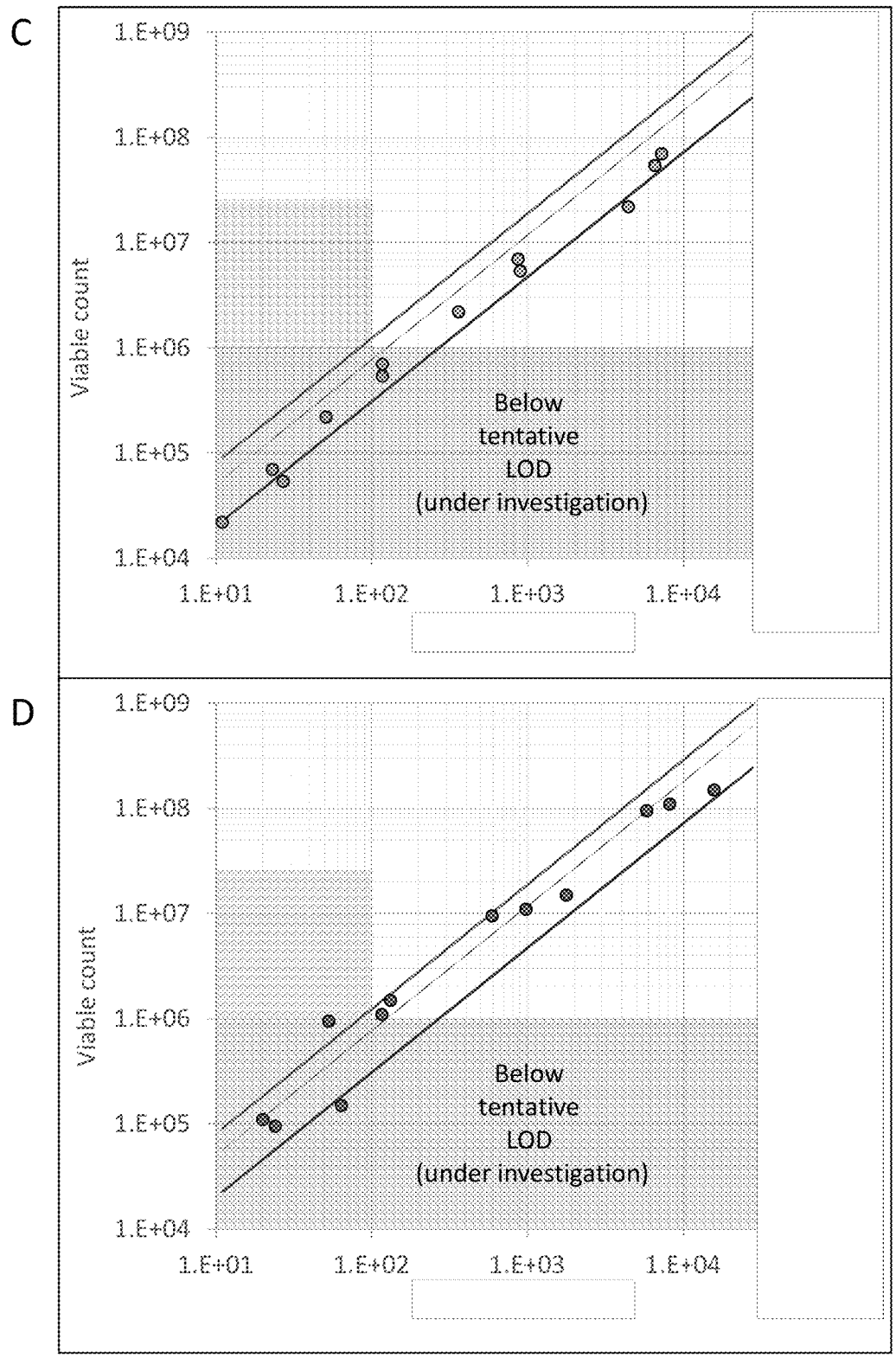
Figure 4:
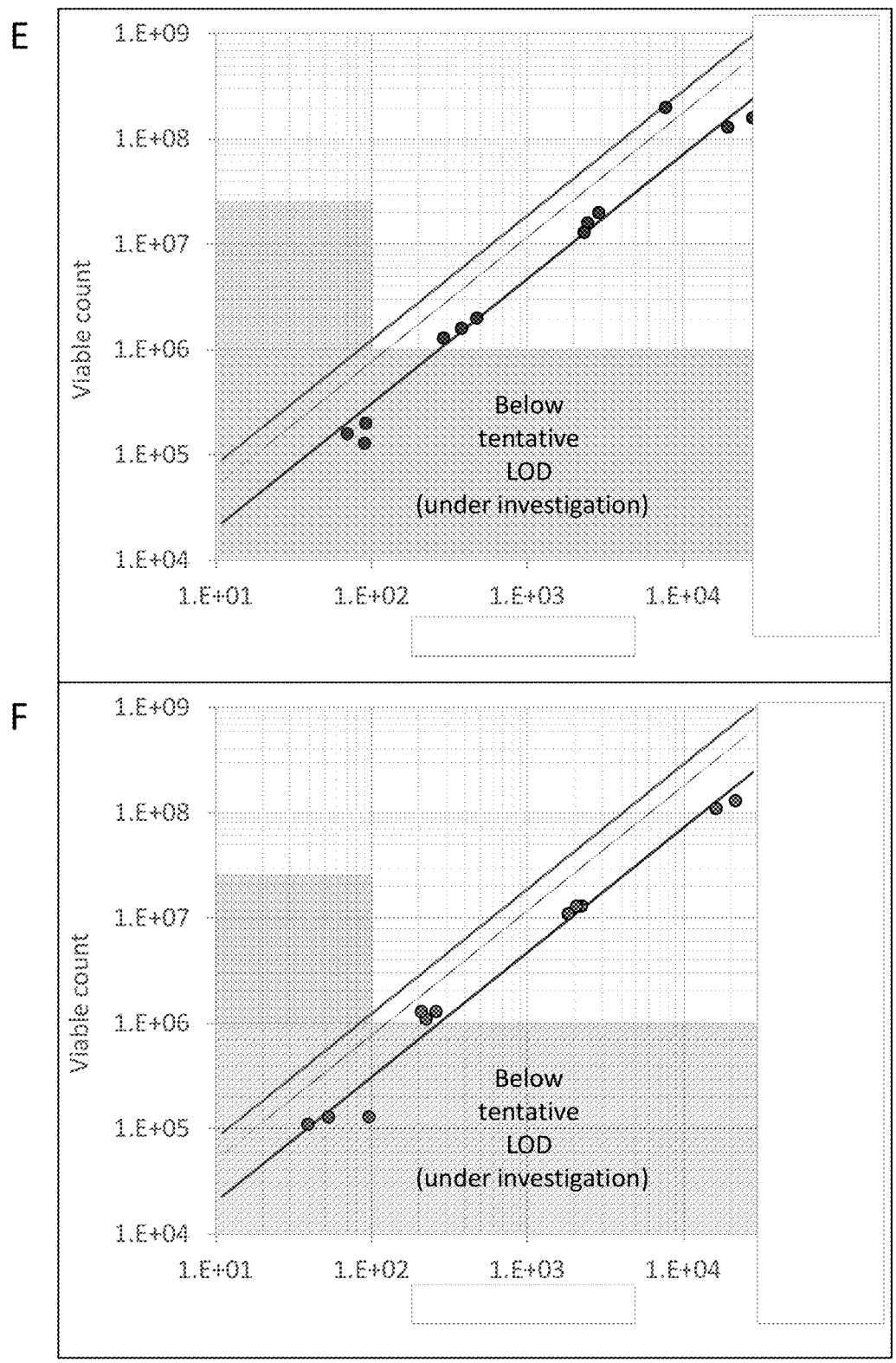

Data from the compiled runs for non-clustering microorganisms were combined to allow a best-fit line to be calculated (FIG. 3). The best-fit line was not generated to provide a mathematical best fit line, but rather was prepared to minimise the number of data points falling outside ±60% limits, as per EUCAST guidelines. Data for individual microorganisms was compared with the generated best-fit line. Counts below the limit of detection are shown in a shaded region. Thus, the same best-fit line can be used to determine the concentration of both Gram-negative and Gram-positive bacteria in a sample.

Figure 5:
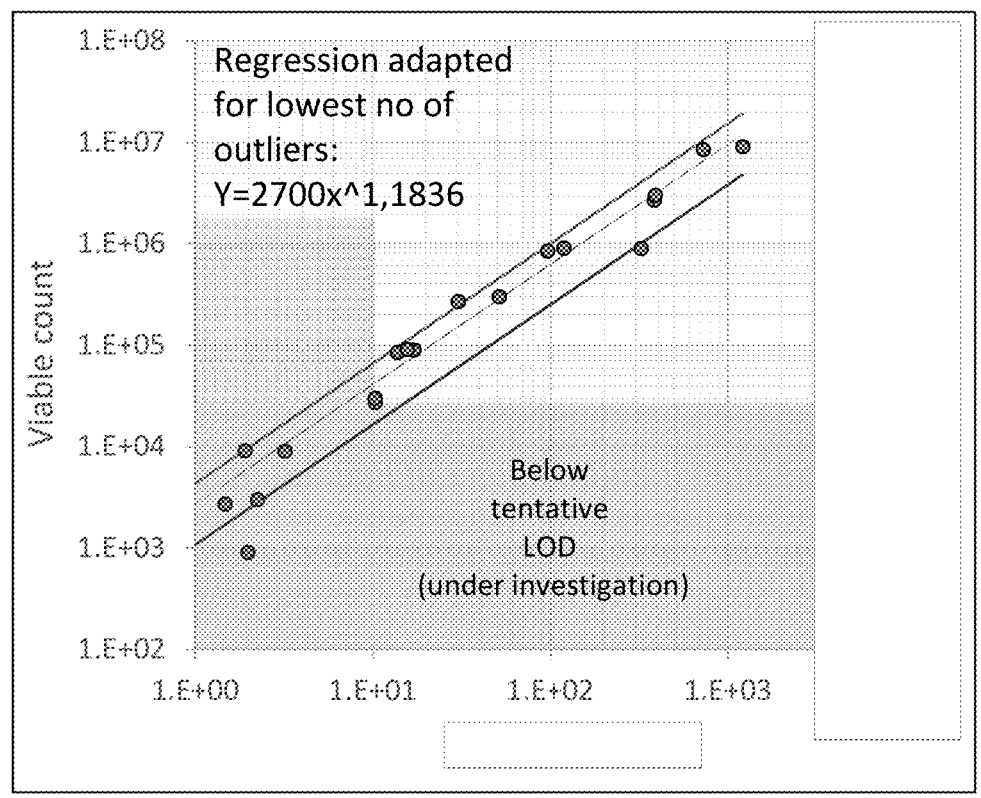
FIG. 5 shows the data and a calibration curve for *S. aureus*. A separate calibration curve was required for *S. aureus*, as this was the only clustering microorganism tested in these experiments.

A separate best-fit line was calculated for *S. aureus* (FIG. 5), a clustering microorganism.

A large proportion of the data points for *H. influenzae* fell outside the original ±60% boundaries for the best fit curves. New best-fit curves based on ±80% boundaries were generated for non-clustering (FIGS. 6 and 7) and clustering (FIG. 8) microorganisms. All data points above the limit of detection, with the exception of *H. influenzae*, fall within the new boundaries.

FIG. 9 shows a schematic and simplified diagram of a first AST apparatus 1 that is suitable for analysing a cell culture sample. The first AST apparatus 1 comprises a processor 10 operable to control subsystems within the first AST apparatus 1, including a sample pipette 12 (i.e. a sample aliquoting device), a diluent pipette 14 (i.e. a diluent aliquoting device), a microscope 16 (i.e. a first imaging device 16), and a line camera 18 (i.e. a second imaging device).

The first AST apparatus 1 receives a first consumable 30*a* in which is provided a sample container 31 (i.e. a container for receiving the sample), a diluent reservoir 35, a diluted aliquot container 36 (i.e. a container for receiving a diluted aliquot), a stain reservoir 37 comprising first and second stains, and an imaging well 38. The imaging well 38 has a viewable area of least 2 mm by 2 mm, and a depth (for example, 3 mm) which is sufficient to allow a liquid depth of at least 2 mm.

The apparatus 1 also receives a second consumable 40*a* which comprises a plurality of wells 42 for test microbial cultures, wherein the wells 42 comprise a plurality of different antimicrobial agents, and each antimicrobial agent is provided at a plurality of concentrations.

In use, a user loads a sample (not shown) into the sample container 31 in the first consumable 30*a*, and loads the first consumable 30*a* into the first AST apparatus 1.

In use the processor 10 is configured to:
dilute the cell culture sample in the diluted aliquot container 36 using diluent transferred by the diluent pipette from the diluent reservoir 35;
transfer the diluted aliquot from the diluted aliquot container 36 to the imaging well 38;
transfer the first and second stains from the stain reservoir 37 to the imaging well 38;
image the imaging well 38 using the microscope 16, to determine the concentration of cells;
transfer the diluted aliquot from the diluted aliquot container 36 to the wells 42;
control the line camera 18 to image the wells 42 for assessing the degree of microbial growth in each well; and
analyse the images in order to determine MIC values for the antimicrobial agents, in order to determine the antimicrobial susceptibility of the microorganism in the sample.

The first and second stains are capable of binding to DNA to provide a sample-stain mixture. The first stain is a fluorescent stain, is cell-permeable, and has a first emission wavelength, and the second stain is cell-impermeable, and is capable of acting as an acceptor molecule in a FRET pair with the first stain acting as a donor molecule. In this example, the first stain is SYTO 9 and the second stain is propidium iodide.

The processor 10 is operable to control the microscope 16 to image the imaging well 38 at the first emission wavelength. In use, the microscope 16 is focused on a plane inside the imaging well 38, for example parallel to the bottom, removed at a distance from the bottom (in this example, 0.2 mm from the bottom), and is configured to move the focal plane continuously through the liquid during the time of imaging, for example for a total of 1.5 mm during the image acquisition time (for example, 20-30 seconds).

The processor 10 is operable to analyse the images obtained by the microscope 16 to determine an image analysis value for the number of objects corresponding to intact microorganisms in the imaged mixture. The processor 10 is configured to compare the image analysis value to a pre-determined calibration curve, thereby to determine the concentration of intact microorganisms in the sample.

Two similar AST apparatuses are shown in FIGS. 10 and 11; both are also suitable for analysing a cell culture sample. The components of these apparatuses are broadly similar to those of the first AST apparatus 1, and discussion of the corresponding features is not repeated here. Instead, the discussion is focussed on the differences compared to the first AST apparatus 1 shown in FIG. 9. In particular, the differences relate to the location of the imaging well 38.

FIG. 10 shows a schematic and simplified diagram of a second AST apparatus 2. Whereas in the first AST apparatus 1 the imaging well 38 is in the first consumable 30*a*, the imaging well is omitted from the first consumable 30*b* of the second AST apparatus 2, and is instead provided in the second consumable 40*b*.

FIG. 11 shows a schematic and simplified diagram of a third AST apparatus 3. The third AST apparatus 3 receives the first consumable 30*b* (as described with reference to FIG. 10) and the second consumable 40*a* (as described with reference to FIG. 9), and also receives a third consumable 50. The imaging well 38 is provided in the third consumable 50.

FIGS. 12 to 14 show schematic and simplified diagrams of three further AST apparatuses 4, 5, 6, which are suitable for receiving a patient sample (for example, a blood sample from a blood culture flask). FIGS. 12 to 14 are broadly similar to FIGS. 9 to 11, respectively. The difference in each case is that the first consumable 30*c* (which includes an imaging well) and 30*d* (which does not include an imaging well) include additional components in order to prepare the patient sample for analysis. The first consumables 30*c* and 30*d* include a lysis buffer reservoir 32, a filter 33 (i.e. a recovery means) and a resuspended cell container 34 (i.e. a container for receiving the sample).

The processor 10 of the further AST apparatuses 4, 5, 6, shown in FIGS. 12 to 14 is further configured to:
cause the sample pipette 12 to transfer an aliquot of the sample from the sample container 31 to a syringe (not shown) to be mixed with lysis buffer from the lysis reservoir 32;
filter the lysed sample through the filter 33;
recover microbial cells from the filter 33 by resuspending them from the filter 33 using culture medium (from a culture medium reservoir, not shown);

FIG. 15 shows a concentration determination apparatus 7 which is similar to the third AST apparatus 3 shown in FIG. 11, except that the concentration determination apparatus 7 does not include the components which make the AST apparatus 3 of FIG. 11 suitable for performing AST analysis. The concentration determination apparatus 7 is adapted to perform a concentration determination analysis only. Compared to the third AST apparatus 3 shown in FIG. 11, the concentration determination apparatus 7 of FIG. 15 omits the second consumable 40*a* and the line camera 18. In this embodiment, the concentration determination apparatus 7 includes the first consumable 30*b* as described above with reference to FIG. 10, and the third consumable 50 as described above with reference to FIG. 11. That is, the imaging well 38 is provided in a separate consumable from the first consumable 30*b*. The concentration determination apparatus 7 is suitable for receiving a cell culture sample. In another embodiment (not shown), in which the concentration determination apparatus is suitable for receiving a patient sample (for example, a blood sample from a blood culture flask), the first consumable 30*b* is replaced by the first consumable 30*d*, such that the concentration determination apparatus includes a lysis buffer reservoir 32, a filter 33 (i.e. a recovery means) and a resuspended cell container 34 (i.e. a container for receiving the sample).

In a similar embodiment (not shown), the concentration determination apparatus 7 could instead use the first consumable 30*a* (as described above with reference to FIG. 9) or the first consumable 30*c* (as described above with reference to FIG. 12). Both of these include the imaging well 38, in which case the third consumable 50 could be omitted. In the case that the first consumable 30*a* is used, the concentration determination apparatus is suitable for receiving a cell culture sample. In the case that the first consumable 30*c* is used, the concentration determination apparatus is suitable for receiving a patient sample (for example, a blood sample from a blood culture flask), because the apparatus then includes a lysis buffer reservoir 32, a filter 33,and a resuspended cell container 34.

FIG. 16 shows a consumable 100 suitable for use as the second consumable 40*a* or 40*b*, or the third consumable 50. This consumable is described in detail in WO 2017/216314. As seen in FIG. 16, the consumable 100 has three layers. A first, optically flat, layer 110 forms a base layer. A second layer 114 is placed on top of the first layer 10 and is formed with volumes for holding fluids in wells 116 (corresponding to wells 42) that are connected via channels 118. The first layer 110 closes the bottoms of the wells 116. A third layer 120 covers the tops of the wells 116 and the channels 18. The third layer 120 includes openings 122 at one end of each of the channels 118 to allow for dispensing of fluid into each channel 118, and then along the channels 118 to fill all of the wells 116. The third layer 120 also includes vents 124 at the other ends of each of the channels 118 to allow for gas to leave the channels 118 as they are filled with the sample fluid(s). The vents 124 and optionally also the openings 122 may be covered by a gas permeable membrane.

All of the layers 10, 14, 20 have a central hole 126 that is used during loading of the sample holder 100 into the apparatus 2. In this example the sample holder 100 has a circular geometry and it can be held in a similar fashion to a CD, thus being supported on a spindle platter and held for rotation with imaging elements above and/or below the sample holder 100. The central hole 126 forms the mounting to couple the sample holder 100 to a spindle platter in the apparatus 1, 2, 3, 4, 5, 6. The first layer 110 and the third layer 120 are transparent to light in the wavelengths used for imaging the samples and typically are transparent to visible light.

The invention claimed is:
1. A method of determining the concentration of intact microorganisms in a sample derived from a sample containing microbial and non-microbial cells, said method comprising:
(a) providing a sample containing microorganisms, wherein non-microbial cells in a sample containing microbial and non-microbial cells have been selectively lysed, or wherein non-microbial cells in a sample containing microbial and non-microbial cells have been selectively lysed and microbial cells have been recovered therefrom;

(b) optionally diluting an aliquot of said sample to provide a diluted aliquot at a dilution value;

(c) contacting at least a portion of an aliquot of the sample of step (a), or of a diluted aliquot of the sample either during or after dilution step (b), with first and second stains capable of binding to DNA to provide a sample-stain mixture, wherein said first stain is a fluorescent stain, is cell-permeable, and has a first emission wavelength, said second stain is cell-impermeable, and is capable of acting as an acceptor molecule in a FRET pair with the first stain acting as a donor molecule and has a higher DNA binding affinity than the first stain, such that the second stain is able to displace the first stain from DNA;

(d) imaging the aliquot-stain mixture of step (c) at the first emission wavelength and determining an image analysis value for the number of objects corresponding to intact microorganisms in the imaged mixture, wherein said imaging is performed on a suspension of microorganisms; and (e) comparing the image analysis value for said aliquot to a pre-determined calibration curve, thereby to determine the concentration of intact microorganisms in said sample.

2. The method of claim 1, wherein:
(i) an aliquot of the sample is diluted to provide a diluted aliquot at a dilution value, wherein contacting step (c) takes place either during or after dilution step (b), and wherein steps (c)-(e) are performed on the diluted aliquot; and/or
(ii) wherein the method comprises diluting aliquots of said sample to provide two or more diluted aliquots at different dilution values, wherein said two or more aliquots are prepared simultaneously before or during step (c), or sequentially wherein a second or further diluted aliquot is prepared after steps (d) and/or (e); and/or
(iii) wherein steps (c) and (d) are performed on two or more aliquots at different dilution values, and wherein step (e) comprises identifying an aliquot which comprises an image analysis value within the range of a pre-determined calibration curve, and comparing the image analysis value for said aliquot to said pre-determined calibration curve, thereby to determine the concentration of viable microorganisms in said sample.

3. The method of claim 2, wherein steps (c) and (d) are performed on each aliquot simultaneously, or wherein steps (c) and (d) are performed on each aliquot sequentially.

4. The method of claim 1, wherein:
(i) when the non-microbial cells in the sample containing microbial and non-microbial cells have been selectively lysed in (a), said method does not comprise detecting the second stain; or
(ii) when the non-microbial cells in the sample containing microbial and non-microbial cells have been selectively lysed and microbial cells have been recovered therefrom in (a), said method comprises detecting the second stain.

5. The method of claim 4, wherein when the non-microbial cells in the sample containing microbial and non-microbial cells have been selectively lysed and microbial cells have been recovered therefrom, step (d) comprises simultaneously imaging each aliquot-stain mixture to detect the first and second stains.

6. The method of claim 1, wherein the sample comprises microorganisms contained in a growth medium.

7. The method of claim 1, wherein the first and second stains are pre-mixed to form a stain solution, prior to contacting the aliquot of the sample or diluted aliquot of the sample, or portion thereof, in step (c).

8. The method of claim 1, wherein:
(i) the fluorescence intensity of said first fluorescent stain at said first emission wavelength is enhanced when the stain is bound to nucleic acid; and/or
(ii) said first fluorescent stain has excitation and emission wavelengths in the wavelength range 350-700 nm; and/or
(iii) said first fluorescent stain is a green-fluorescent stain; and/or
(iv) said first fluorescent stain is an unsymmetrical cyanine dye; and/or
(v) the first fluorescent stain is a SYTO stain; and/or
(vi) the first fluorescent stain is SYTO BC; and/or
(vii) the second stain is a fluorescent stain; and/or
(viii) the second stain is a red-fluorescent stain; and/or
(ix) the red-fluorescent stain is propidium iodide.

9. The method of claim 1, wherein:
(i) an image is obtained at one or more focal planes through the suspension; or
(ii) said imaging comprises obtaining a series of 2-D images along an optical axis,
wherein each image is obtained at a different position along the optical axis through a volume of the suspension.

10. The method of claim 9, wherein:
(i) step (c) of contacting with the stains is performed at a temperature of greater than 4° C.; and/or
(ii) in the contacting of step (c) the aliquot or diluted aliquot, or portion thereof, is incubated with the first and second stains for a time period of 1 to 20 minutes; and/or
(iii) the imaging in step (d) is carried out at room temperature; and/or
(iv) in the imaging step (d) it is identified whether the microorganisms are clustering or non-clustering and a calibration curve is used which is predetermined for clustering or non-clustering microorganisms; and/or
(v) the images are analysed for fluorescence intensity and/or size of each enumerated object, and optionally morphology of each enumerated object; and/or
(vi) the images are analysed for maximum fluorescence intensity, median fluorescence intensity and/or area of each enumerated object; and/or
(vii) the images are analysed for maximum, median and/or mean fluorescence intensity and/or area of the population of objects; and/or
(viii) the concentration of viable microorganisms is determined.

11. A method for determining the antimicrobial susceptibility of a microorganism in a sample, said method comprising:
(i) providing a sample containing a viable microorganism wherein (i) non-microbial cells in a sample containing microbial and non-microbial cells have been selectively lysed, or wherein (ii) non-microbial cells in a sample containing microbial and non-microbial cells have been selectively lysed and microbial cells have been recovered therefrom;
(ii) performing steps (b)-(e) as defined in claim 1 on said sample to determine the concentration of intact microbial cells in said sample;
(iii) inoculating a series of test microbial cultures for an antibiotic susceptibility test (AST) using the sample in step (i), wherein the series of test microbial cultures comprises at least two different growth conditions, wherein the different growth conditions comprise one or more different antimicrobial agents, and each antimicrobial agent is tested at two or more different concentrations; and (iv) assessing the degree of microbial growth in each growth condition;

wherein the concentration of microbial cells in said sample or said test microbial cultures is adjusted if necessary to a desired or pre-determined concentration; and wherein the degree of microbial growth in each growth condition is used to determine at least one MIC value for at least one antimicrobial agent, thereby to determine the antimicrobial susceptibility of said microorganism in said sample.

12. The method of claim 11, wherein:
(i) based on the concentration determined in step (ii), the concentration of at least a portion of the sample of step (i) is adjusted to provide an inoculum for inoculating the test microbial cultures in step (iii); and/or
(ii) the step of adjusting the concentration comprises a dilution based on the concentration determined in step (ii); and/or
(iii) following step (ii), at least a portion of the sample of step (i) is diluted to provide an inoculum for step (iii); and/or
(iv) wherein the concentration of microorganisms in the inoculated microbial test cultures is in the range $4.5 \times 10^5 \pm 80\%$ or $5 \times 10^5 \pm 60\%$; and/or
(v) at least one of the test microbial cultures comprises fastidious medium; and/or
(vi) the concentration adjustment comprises culturing or further culturing the sample;
and/or
(vii) if the concentration of microorganisms in the sample is below $1 \times 10^6$ microorganisms, the AST assay is not performed with the sample.

* * * * *